US008198410B2

(12) United States Patent
Wild, Jr. et al.

(10) Patent No.: US 8,198,410 B2
(45) Date of Patent: *Jun. 12, 2012

(54) HUMAN ANTI-NGF NEUTRALIZING ANTIBODIES AS SELECTIVE NGF PATHWAY INHIBITORS

(75) Inventors: Kenneth D. Wild, Jr., Simi Valley, CA (US); James J. S. Treanor, Sherman Oaks, CA (US); Haichun Huang, Fremont, CA (US); Heather Inoue, Oak Park, CA (US); Tie J. Zhang, Thousand Oaks, CA (US); Frank Martin, Newburty park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/277,919

(22) Filed: Nov. 25, 2008

(65) Prior Publication Data

US 2009/0155274 A1 Jun. 18, 2009

Related U.S. Application Data

(63) Continuation of application No. 10/891,658, filed on Jul. 15, 2004, now Pat. No. 7,601,818.

(60) Provisional application No. 60/487,431, filed on Jul. 15, 2003.

(51) Int. Cl.
*C07K 16/18* (2006.01)
(52) U.S. Cl. ............. 530/387.1; 530/350; 530/387.3; 530/388.24
(58) Field of Classification Search ............. 530/350, 530/387.1, 387.3, 388.24
See application file for complete search history.

(56) References Cited

U.S. PATENT DOCUMENTS

| | | | |
|---|---|---|---|
| 4,230,691 A | 10/1980 | Young et al. | |
| 4,786,593 A | 11/1988 | Ross et al. | |
| 5,147,294 A | 9/1992 | Smith et al. | |
| 5,712,100 A | 1/1998 | Nakahama et al. | |
| 5,844,092 A | 12/1998 | Presta et al. | |
| 5,877,016 A | 3/1999 | Presta et al. | |
| 6,029,114 A | 2/2000 | Shamovsky et al. | |
| 6,153,189 A | 11/2000 | Presta et al. | |
| 6,548,062 B2 | 4/2003 | Buchkovich et al. | |
| 6,627,196 B1 | 9/2003 | Baughman et al. | |
| 6,919,426 B2 | 7/2005 | Boone et al. | |
| 7,067,131 B2 | 6/2006 | Gudas et al. | |
| 7,252,822 B2* | 8/2007 | Shelton et al. | |
| 2001/0046959 A1 | 11/2001 | Buchkovich et al. | |
| 2003/0039649 A1 | 2/2003 | Foote | |
| 2004/0219144 A1 | 11/2004 | Shelton | |
| 2004/0237124 A1 | 11/2004 | Pons et al. | |
| 2005/0074821 A1 | 4/2005 | Wild et al. | |
| 2007/0212357 A1 | 9/2007 | Pons et al. | |
| 2008/0033157 A1 | 2/2008 | Wild et al. | |

FOREIGN PATENT DOCUMENTS

| | | |
|---|---|---|
| EP | 00418590 | 3/1991 |
| EP | 1369431 | 4/2003 |
| JP | 02219593 | 9/1990 |
| JP | 03163095 | 7/1991 |
| JP | 05076384 | 3/1993 |
| JP | 05292995 | 11/1993 |
| JP | 06189787 | 7/1994 |
| JP | 06317587 | 11/1994 |
| WO | 90/10644 | 9/1990 |
| WO | 96/33735 | 10/1996 |
| WO | 01/09187 | 2/2001 |
| WO | 01/64247 | 9/2001 |
| WO | 01/78698 | 10/2001 |
| WO | 02/096458 | 12/2002 |
| WO | 03/033538 | 4/2003 |
| WO | 2004/032870 | 4/2004 |
| WO | 2006/077441 | 7/2006 |
| WO | 2006/110883 | 10/2006 |

OTHER PUBLICATIONS

Bird et al. Science, 242(4877):423-426, Oct. 21, 1988.*
Holt et al., Trends in Biotechnology, vol. 21, No. 11, Nov. 2003, pp. 484-490. "Domain antibodies: proteins for therapy".
Hongo et al, 2000. Hybridoma, 19:215-227. "Antibody Binding Regions on Human Nerve Growth Factor Identified by Homolog- and Alanine-Scanning Mutagenesis".
Ruberti et al., 1993, Cellular and Molecular Neurobiology, 13:559-668. "Cloning and Expression of an Anti-Nerve Growth Factor (NGF) Antibody for Studies Using the Neuroantibody Approach".
GenBank Accession No. U39608 [Mar. 25, 1999].
GenBank Accession No. U39609 [Jan. 28, 1999].
GenBank Accession No. L17077 [Feb. 7, 1995].
GenBank Accession No. L17078 [[Feb. 7, 1995].
Weismann, et al., Nature 401:184-188 (1999).
Schaeble, KF and Zachau, HG, Biol. Chem. Hoppe-Seyler, 374:1001-1022 (1993). "The Variable Genes of the Human Immunoglobulin chi Locus".
Heiter, PA et al., J. Biological Chem., 257(3):1516-1522 (1982). "Evolution of Human Immunoglobulin kappa Region Genes".
Klein, R. et al., Eur. J. Immunol. 23:3248-3271 (1993). "Expressed Human Immunoglobulin chi Genes and Their Hypermutation".
Bendig, M.M., Methods: A Companion to Methods in Enzymology, (1995) 8:83-93.
Businaro, R., et al., J. Neurosci. Res. (1981) 6:89-98. "Monoclonal Antibodies Against Mouse Nerve Growth Factor Produced by Somatic Cell Hybrids".
Ebendal, T., et al., J. Neurosci. Res. (1989) 22:223-240. "Characterization of Antibodies to Synthetic Nerve Growth Factor (NgGF) and ProNGF Peptides".
Korsching, S. & Thoenen, H., Proc. Natl. Acad. Sci. USA (Jun. 1983) 80:3513-3516). "Nerve Growth Factor in Sympathetic Ganglia and Corresponding Target Organs of the Rat: Correlation with Density of Sympathetic Innervation".

(Continued)

*Primary Examiner* — Stephen Rawlings
(74) *Attorney, Agent, or Firm* — McDonnell Boehnen Hulbert & Berghoff

(57) ABSTRACT

This invention provides antibodies that interact with or bind to human nerve growth factor (NGF) and neutralize the function of NGF thereby. The invention also provides pharmaceutical compositions of said antibodies and methods for neutralizing NGF function, and particularly for treating NGF-related disorders (e.g., chronic pain) by administering a pharmaceutically effective amount of anti-NGF antibodies. Methods of detecting the amount of NGF in a sample using anti-NGF antibodies are also provided.

12 Claims, 13 Drawing Sheets

OTHER PUBLICATIONS

Molnar, M., et al., Eur. J. Neurosci., (1998) 10:3127-3140. "The Effects of Anti-Nerve Growth Factor Monoclonal Antibodies on Developing Basal Forebrain Neurons are Transient and Reversible".

Nanduri, J. et al., (1994) 37:433-444. "Immunological Determinants of Nerve Growth Factor Involved in p140trk (Trk) Receptor Binding".

Paul, W.E., (ed.) Fundamental Immunology, 3rd ed, pp. 292-295 (1993).

Rudikoff, et al., Proc Natl Acad Sci USA, 79(6):1979-1983 (1994).

Coleman, P.M., Research in Immunology, 145:33-36 (1994).

MacCallum, et al., J Mol Biol, 262:732-745 (1996).

Casset, et al., Biochemical and Biophysical Research Communications, 307:198-205 (2003).

Ruberti, F., et al., Journal of Neuroscience, 20(7):2589-2601 (Apr. 1, 2000). "Phenotypic Knockout of Nerve Growth Factor in Adult Transgenic Mice Reveals Severe Deficits in Basal Forebrain Cholinergic Neurons, Cell Death in the Spleen, and Skeletal Muscle Dystrophy".

Tomizuka, K., et al., Bio Industry, vol. 20(7): 43-51 (Jul. 12, 2003). "Development of Human Antibody Therapeutic Using Trans-Chromo (TC) Mouse", English translation of Abstract provided.

* cited by examiner

FIGURE 2
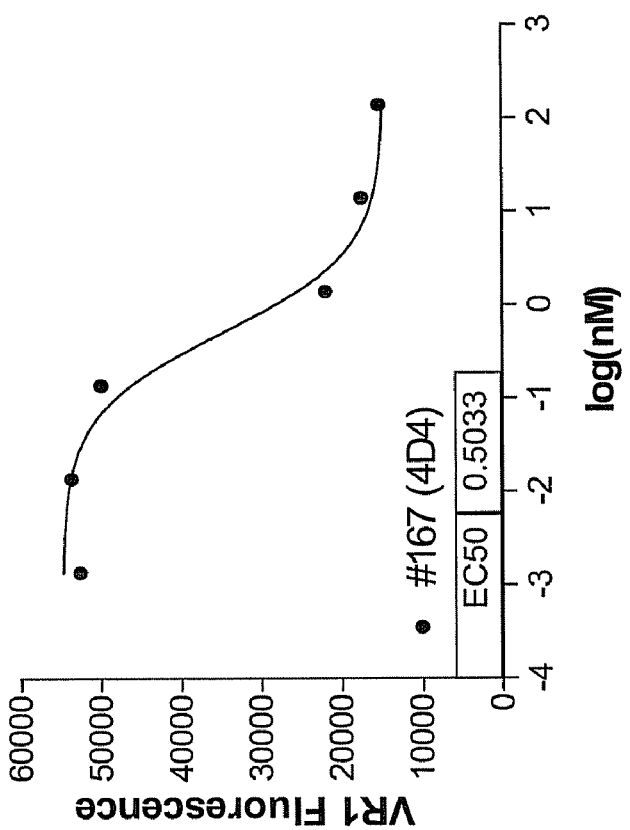
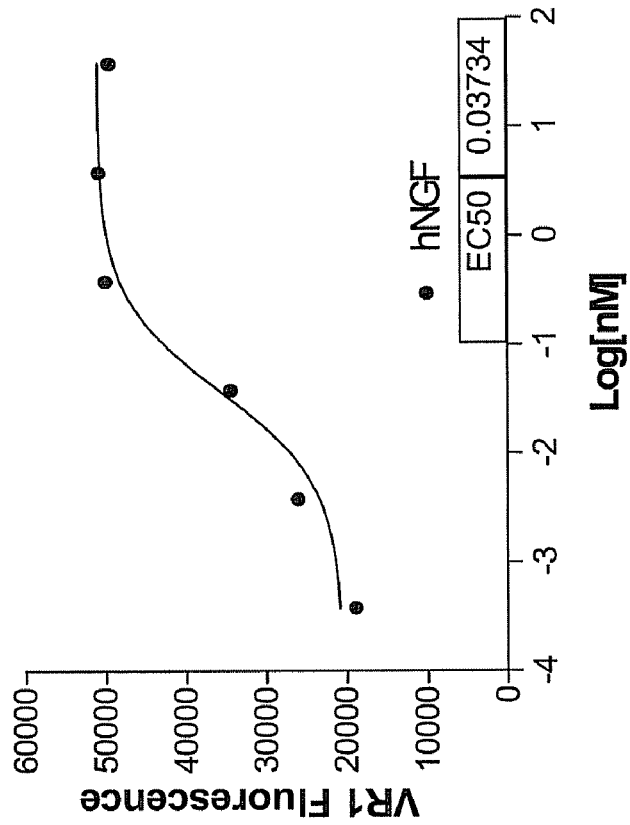

FIGURE 5

NGF CDR1 heavy chain alignments/ % identity

```
                    (1)     1     5
     14D10 HC CDR1  (1)   DYAMH
       6H9 HC CDR1  (1)   DYAMH
       7H2 HC CDR1  (1)   DYAMH
       4G6 HC CDR1  (1)   DYGMN
     14D11 HC CDR1  (1)   TYWIG
       4D4 HC CDR1  (1)   SYSMN
```

| | 14D10 HC CDR1 | 6H9 HC CDR1 | 7H2 HC CDR1 | 4G6 HC CDR1 | 14D11 HC CDR1 | 4D4 HC CDR1 |
|---|---|---|---|---|---|---|
| 14D10 HC CDR1 | 100 | 100 | 100 | 60 | 20 | 40 |
| 6H9 HC CDR1 | | 100 | 100 | 60 | 20 | 40 |
| 7H2 HC CDR1 | | | 100 | 60 | 20 | 40 |
| 4G6 HC CDR1 | | | | 100 | 20 | 60 |
| 14D11 HC CDR1 | | | | | 100 | 20 |
| 4D4 HC CDR1 | | | | | | 100 |

FIGURE 6

NGF CDR2 heavy chain alignments/% identity

```
                    (1) 1                        17
14D10 HC CDR2   (1) GISWNRGIIGYADSVKG
  6H9 HC CDR2   (1) GISWNRGIIGYAGSVKG
 7H2 HC CDR2    (1) GITWNSGIIGYADSVKG
 4G6 HC CDR2    (1) DINWNGGSTGYADSVKG
 4D4 HC CDR2    (1) YISRSSHTIFYADSVKG
14D11 HC CDR2   (1) IIYPGDSDTKYSPSFQG
```

| | 14D10 HC CDR2 | 6H9 HC CDR2 | 14D11 HC CDR2 | 4D4 HC CDR2 | 4G6 HC CDR2 | 7H2 HC CDR2 |
|---|---|---|---|---|---|---|
| 14D10 HC CDR2 | 100 | 94 | 24 | 59 | 70 | 82 |
| 6H9 HC CDR2 | | 100 | 24 | 53 | 65 | 76 |
| 14D11 HC CDR2 | | | 100 | 24 | 29 | 24 |
| 4D4 HC CDR2 | | | | 100 | 47 | 53 |
| 4G6 HC CDR2 | | | | | 100 | 70 |
| 7H2 HC CDR2 | | | | | | 100 |

FIGURE 7

NGF CDR3 heavy chain alignments/% identity

```
               (1) 1                17
14D10 HC CDR3  (1) GYYGSGRPGYFYYVMDV
  6H9 HC CDR3  (1) GYYGSGRPGYFYYVMDV
14D11 HC CDR3  (1) -NYYGSGTYYYYGMNV
  4G6 HC CDR3  (1) --EQWLDYYYYVGMDV
  4D4 HC CDR3  (1) -VYS-SGWHVSDY-FDY
  7H2 HC CDR3  (1) ---EGSGR---YYNFDY
```

|              | 14D10 HC CDR3 | 6H9 HC CDR3 | 14D11 HC CDR3 | 4G6 HC CDR3 | 4D4 HC CDR3 | 7H2 HC CDR3 |
|---|---|---|---|---|---|---|
| 14D10 HC CDR3 | 100 | 100 | 35 | 41 | 18 | 18 |
| 6H9 HC CDR3 |  | 100 | 35 | 41 | 18 | 18 |
| 14D11 HC CDR3 |  |  | 100 | 53 | 29 | 35 |
| 4G6 HC CDR3 |  |  |  | 100 | 18 | 29 |
| 4D4 HC CDR3 |  |  |  |  | 100 | 41 |
| 7H2 HC CDR3 |  |  |  |  |  | 100 |

FIGURE 8

NGF CDR1 light chain alignments/% identity

```
                                     (1)  1           12
              14D11 LC CDR1          (1)  RASQGISIWLA-
   4G6 LC CDR1 20031028340           (1)  RASQGISSWIA-
              4D4 LC CDR1            (1)  RASQGISSALA-
   4G6 LC CDR1 20031028351           (1)  RASQGVSSYLA-
              14D10 LC CDR1          (1)  RASQSVSSGFLA
   4G6 LC CDR1 20031000528           (1)  RASQSVSSYLA
   4G6 LC CDR1 20031071526           (1)  RASQSVSSYLA
              6H9 LC CDR1            (1)  RASQSVSSYLA
              7H2 LC CDR1            (1)  RASQSVSSYLA
   NGF 4G6 LC CDR1 20031028344       (1)  RASQSVSSYLA
```

| | 14D11 LC CDR1 | 4G6 LC CDR1 20031028340 | 4D4 LC CDR1 | 4G6 LC CDR1 20031028351 | 14D10 LC CDR1 | 4G6 LC CDR1 20031000528 | 4G6 LC CDR1 20031071526 | 6H9 LC CDR1 |
|---|---|---|---|---|---|---|---|---|
| 14D11 LC CDR1 | 100 | 92 | 83 | 75 | 42 | 67 | 42 | 42 |
| 4G6 LC CDR1 20031028340 | | 100 | 92 | 83 | 50 | 75 | 50 | 50 |
| 4D4 LC CDR1 | | | 100 | 83 | 50 | 75 | 50 | 50 |
| 4G6 LC CDR1 20031028351 | | | | 100 | 58 | 92 | 58 | 58 |
| 14D10 LC CDR1 | | | | | 100 | 67 | 83 | 83 |
| 4G6 LC CDR1 20031000528 | | | | | | 100 | 67 | 67 |
| 4G6 LC CDR1 20031071526 | | | | | | | 100 | 100 |
| 6H9 LC CDR1 | | | | | | | | 100 |
| 7H2 LC CDR1 | | | | | | | | |
| NGF 4G6 LC CDR1 20031028344 | | | | | | | | |

FIGURE 9

NGF CDR2 light chain alignments/% identity

```
                                    (1) 1       7
             14D11 LC CDR2     (1) KASSLQS
    4G6 LC CDR2 20031028340    (1) KASSLQS
              4D4 LC CDR2      (1) DASSLES
    4G6 LC CDR2 20031000528    (1) DASNRAT
    4G6 LC CDR2 20031028351    (1) DASNRAT
              6H9 LC CDR2      (1) VASSRAT
             14D10 LC CDR2     (1) GASSRAT
    4G6 LC CDR2 20031071526    (1) GASSRAT
              7H2 LC CDR2      (1) GASSRAT
NGF 4G6 LC CDR2 20031028344    (1) GASSRAT
```

| | 14D11 LC CDR2 | 4G6 LC CDR2 20031028340 | 4D4 LC CDR2 | 4G6 LC CDR2 20031000528 | 4G6 LC CDR2 20031028351 | 6H9 LC CDR2 | 14D10 LC CDR2 | 4G6 LC CDR2 20031071526 | 7H2 LC CDR2 | NGF 4G6 LC CDR2 20031028344 |
|---|---|---|---|---|---|---|---|---|---|---|
| 14D11 LC CDR2 | 100 | 100 | 71 | 28 | 28 | 43 | 43 | 43 | 43 | 43 |
| 4G6 LC CDR2 20031028340 | | 100 | 71 | 28 | 28 | 43 | 43 | 43 | 43 | 43 |
| 4D4 LC CDR2 | | | 100 | 43 | 43 | 43 | 43 | 43 | 43 | 43 |
| 4G6 LC CDR2 20031000528 | | | | 100 | 100 | 71 | 71 | 71 | 71 | 71 |
| 4G6 LC CDR2 20031028351 | | | | | 100 | 71 | 71 | 71 | 71 | 71 |
| 6H9 LC CDR2 | | | | | | 100 | 86 | 86 | 86 | 86 |
| 14D10 LC CDR2 | | | | | | | 100 | 100 | 100 | 100 |
| 4G6 LC CDR2 20031071526 | | | | | | | | 100 | 100 | 100 |
| 7H2 LC CDR2 | | | | | | | | | 100 | 100 |
| NGF 4G6 LC CDR2 20031028344 | | | | | | | | | | 100 |

FIGURE 10

NGF CDR3 light chain alignments/% identity

```
                              (1)           1           9
        14D10 LC CDR3         (1)   QQYGSSPYT
          7H2 LC CDR3         (1)   QQYGSS-YT
          6H9 LC CDR3         (1)   QQYGSSPYT
 4G6 LC CDR3 20031000528      (1)   QQRSNWPWT
 4G6 LC CDR3 20031028351      (1)   QQRSNWHRT
        14D11 LC CDR3         (1)   QQANSFPWT
          4D4 LC CDR3         (1)   QQFNSYPLT
 4G6 LC CDR3 20031028340      (1)   QQYNSYPWT
 4G6 LC CDR3 20031071526      (1)   QQYNSYPWT
 NGF 4G6 LC CDR3 20031028344  (1)   QQYGSSPYT
```

| | 14D10 LC CDR3 | 7H2 LC CDR3 | 6H9 LC CDR3 | 4G6 LC CDR3 20031000528 | 4G6 LC CDR3 20031028351 | 14D11 LC CDR3 | 4D4 LC CDR3 | 4G6 LC CDR3 20031028340 | 4G6 LC CDR3 20031071526 | NGF 4G6 LC CDR3 20031028344 |
|---|---|---|---|---|---|---|---|---|---|---|
| 14D10 LC CDR3 | 100 | 89 | 100 | 44 | 33 | 56 | 56 | 67 | 67 | 100 |
| 7H2 LC CDR3 | | 100 | 89 | 33 | 33 | 44 | 44 | 56 | 56 | 89 |
| 6H9 LC CDR3 | | | 100 | 44 | 33 | 56 | 56 | 67 | 67 | 100 |
| 4G6 LC CDR3 20031000528 | | | | 100 | 78 | 56 | 44 | 56 | 56 | 44 |
| 4G6 LC CDR3 20031028351 | | | | | 100 | 33 | 33 | 33 | 33 | 33 |
| 14D11 LC CDR3 | | | | | | 100 | 67 | 78 | 78 | 56 |
| 4D4 LC CDR3 | | | | | | | 100 | 78 | 78 | 56 |
| 4G6 LC CDR3 20031028340 | | | | | | | | 100 | 100 | 67 |
| 4G6 LC CDR3 20031071526 | | | | | | | | | 100 | 67 |
| NGF 4G6 LC CDR3 20031028344 | | | | | | | | | | 100 |

FIGURE 11

Alignment of light chain variable regions of mAbs 4G6, 7H2, 14D10, 14D11, 4G6, 4D4

FIGURE 12

Alignment of heavy chain variable regions of mAbs 4D4, 4G6, 14D10, 14D11, 7H2, 6H9

Section 1

|  | | CDR1 | CDR2 | |
|---|---|---|---|---|
| 4D4 VH | (1) | EVQLVESGGGLVQPGGSLRLSCAASGFTLHSYSMNWVRQAPGKGLEWVSYISRSSHTIFYADSVKG |
| NGF 14D10 HC 20031071581 v region | (1) | EVQLVESGGGLVQPGGSLRLSCAASGFTFEDYAMHWVRQAPGKGLEWVSGISMNRGIIGYADSVKG |
| NGF 6H9 HC Hu-Rat IgG2b.b 20021120864 final V region | (1) | EVQLVESGGGLVQPGRSLRLSCTASGFTFTDYAMHWVRQAPGKGLEWVSGISMNRGIIGYAGSVKG |
| NGF 7H2 Hu-Rat IgG2b.b 20021181 41 final V region | (1) | EVQLVESGGGLVQPGRSLRLSCAASGFTFTDYAMHWVRQAPGKGLEWVSGITMNSGIIGYADSVKG |
| NGF 14D11 HC race 20031028394rc V region | (1) | EVQLVQSGAEVKKPGESLKISCKGSGYNFTTYWIGWVRQMPGKGLEWMGIIYPGDSDTKYSPSFQG |
| NGF 4G6 HC pCR4TOPO 20031028328r V region | (1) | EVQLVESGGGVVRPGGSLRLSCAASGFTFTDYGMUWVRQAPGKGLEWVSDINWNGGSTGYADSVKG |

Section 2

|  | | CDR3 | |
|---|---|---|---|
| 4D4 VH | (67) | RFTISRDNAKNSLYLQMDSLRDEDTAMYYCAR---VYSSGMHVSDYFD-YMGQGILVTVSS |
| NGF 14D10 HC 20031071581 v region | (67) | RFTISRDNAKMSLYLQMNSLRAEDTALYYCAKEGYYGSGRPGYFYYVMDVMGQGTTVTVSS |
| NGF 6H9 HC Hu-Rat IgG2b.b 20021120864 final V region | (67) | RFTISRDNAKMSLYLQMNSLRAEDTALYYCVKEGYYGSGRPGYFYYVMDVMGQGTTVTVSS |
| NGF 7H2 Hu-Rat IgG2b.b 20021181 41 final V region | (67) | RFTISRDDAKNSLYLQMNSLRAEDTALYYCAKE------EGSGRYNFD-YMGQGTTVTVSS |
| NGF 14D11 HC race 20031028394rc V region | (67) | QVTISADKSISTAYLQWSSLKASDTAMYYCAR---NYYGSGTYYYYYGMNVMGQGTTVTVSS |
| NGF 4G6 HC pCR4TOPO 20031028328r V region | (67) | RFTISRDNAKNSLYLQMNSLRAEDTALYYCAR---EQWLDPYYYYYGMDVMGQGTTVTVSS |

SEQUENCE LISTING

<160> NUMBER OF SEQ ID NOS: 141

<210> SEQ ID NO 1
<211> LENGTH: 990
<212> TYPE: DNA
<213> ORGANISM: Homo sapiens

<400> SEQUENCE: 1

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggggga     360
ccgtcagtct tcctcttccc cccaaaaccc aaggacaccc tcatgatctc ccggaccccct    420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990
```

<210> SEQ ID NO 2
<211> LENGTH: 330
<212> TYPE: PRT
<213> ORGANISM: Homo sapiens

<400> SEQUENCE: 2

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 3
<211> LENGTH: 978
<212> TYPE: DNA
<213> ORGANISM: Homo sapiens

<400> SEQUENCE: 3
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggaccctga ggtcacgtgc      420 gtggtggtgg acgtgagcca cgaagacccc gaggtccagt tcaactggta cgtggacggc     480
```

-continued

```
gtggaggtgc ataatgccaa gacaaagcca cgggaggagc agttcaacag cacgttccgt    540
gtggtcagcg tcctcaccgt tgtgcaccag gactggctga acggcaagga gtacaagtgc    600
aaggtctcca acaaaggcct cccagccccc atcgagaaaa ccatctccaa aaccaaaggg    660
cagccccgag aaccacaggt gtacaccctg cccccatccc gggaggagat gaccaagaac    720
caggtcagcc tgacctgcct ggtcaaaggc ttctacccca gcgacatcgc cgtggagtgg    780
gagagcaatg ggcagccgga gaacaactac aagaccacac ctcccatgct ggactccgac    840
ggctccttct tcctctacag caagctcacc gtggacaaga gcaggtggca gcagggaac    900 gtcttctcat gctccgtgat gcatgaggct ctgcacaacc actacacgca gaagagcctc    960
tccctgtctc cgggtaaa                                                  978
```

<210> SEQ ID NO 4
<211> LENGTH: 326
<212> TYPE: PRT
<213> ORGANISM: Homo sapiens

<400> SEQUENCE: 4

```
Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 5
<211> LENGTH: 981
<212> TYPE: DNA
<213> ORGANISM: Homo sapiens

<400> SEQUENCE: 5
gccagcacca aggggccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc cccatgccc atcatgccca gcacctgagt tcctgggggg accatcagtc      360
ttcctgttcc cccaaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtgraca agagcaggtg gcaggagggg     900
aatgtcttct catgctccgt gakgcatgag gctctgcaca accactacac acagaagagc     960
ctctccctgt ctctgggtaa a                                               981

<210> SEQ ID NO 6
<211> LENGTH: 327
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110
```

```
Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 7
<211> LENGTH: 321
<212> TYPE: DNA
<213> ORGANISM: Homo sapiens

<400> SEQUENCE: 7
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 8
<211> LENGTH: 107
<212> TYPE: PRT
<213> ORGANISM: Homo sapiens

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 9
<211> LENGTH: 369
<212> TYPE: DNA
<213> ORGANISM: Homo sapiens

<400> SEQUENCE: 9
gaggtgcagc tggtggagtc tgggggaggc ttggtacagc ctggggggtc cctgagactc     60
tcctgtgcag cctctggctt caccttaaga agttatagca tgaactgggt tcgccaggct    120
ccagggaagg ggctggagtg ggtttcatac attagtcgta gtagtcatac catattctac    180
gcagactctg tgaagggccg attcaccatc tccagagaca tgccaagaa ttcactgtat    240 ctgcaaatgg acagcctgag agacgaggac acggctatgt attactgtgc gagagtatat    300
agcagtggct ggcacgtctc tgattatttt gactactggg gccagggaat cctggtcacc    360
gtttcctca                                                            369

<210> SEQ ID NO 10
<211> LENGTH: 123
<212> TYPE: PRT
<213> ORGANISM: Homo sapiens

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Ser Tyr
            20                  25                  30

Ser Met Asn Trp Val Arg Gln Ala Pro Gly Lys Gly Leu Glu Trp Val
        35                  40                  45

Ser Tyr Ile Ser Arg Ser Ser His Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Asp Glu Asp Thr Ala Met Tyr Tyr Cys
                85                  90                  95

Ala Arg Val Tyr Ser Ser Gly Trp His Val Ser Asp Tyr Phe Asp Tyr
            100                 105                 110

Trp Gly Gln Gly Ile Leu Val Thr Val Ser Ser
        115                 120

<210> SEQ ID NO 11
<211> LENGTH: 321
<212> TYPE: DNA
<213> ORGANISM: Homo sapiens

<400> SEQUENCE: 11
gccatccagt tgacccagtc tccatcctcc ctgtctgcat ctgtaggaga cagagtcacc     60
atcacttgcc gggcaagtca gggcattagc agtgctttag cctggtatca gcagaaacca    120
gggaaagctc ctaagctcct gatctatgat gcctccagtt tggaaagtgg ggtcccatca    180

```
aggttcagcg gcagtggatc tgggacagat ttcactctca ccatcagcag cctgcagcct      240
gaagattttg caacttatta ctgtcaacag tttaatagtt acccgctcac tttcggcgga      300
gggaccaagg tggagatcaa a                                                321
```

```
<210> SEQ ID NO 12
<211> LENGTH: 107
<212> TYPE: PRT
<213> ORGANISM: Homo sapiens

<400> SEQUENCE: 12
```

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

```
<210> SEQ ID NO 13
<211> LENGTH: 42
<212> TYPE: DNA
<213> ORGANISM: Homo sapiens

<400> SEQUENCE: 13
gtatatagca gtggctggca cgtctctgat tattttgact ac                         42
```

```
<210> SEQ ID NO 14
<211> LENGTH: 14
<212> TYPE: PRT
<213> ORGANISM: Homo sapiens

<400> SEQUENCE: 14
```

```
Val Tyr Ser Ser Gly Trp His Val Ser Asp Tyr Phe Asp Tyr
1               5                   10
```

```
<210> SEQ ID NO 15
<211> LENGTH: 27
<212> TYPE: DNA
<213> ORGANISM: Homo sapiens

<400> SEQUENCE: 15
caacagttta atagttaccc gctcact                                          27
```

```
<210> SEQ ID NO 16
<211> LENGTH: 9
<212> TYPE: PRT
<213> ORGANISM: Homo sapiens

<400> SEQUENCE: 16
```

```
Gln Gln Phe Asn Ser Tyr Pro Leu Thr
1               5
```

```
<210> SEQ ID NO 17
<211> LENGTH: 51
```

```
<212> TYPE: DNA
<213> ORGANISM: Homo sapiens

<400> SEQUENCE: 17
tacattagtc gtagtagtca taccatattc tacgcagact ctgtgaaggg c        51

<210> SEQ ID NO 18
<211> LENGTH: 17
<212> TYPE: PRT
<213> ORGANISM: Homo sapiens

<400> SEQUENCE: 18

Tyr Ile Ser Arg Ser Ser His Thr Ile Phe Tyr Ala Asp Ser Val Lys
1               5                   10                  15

Gly

<210> SEQ ID NO 19
<211> LENGTH: 21
<212> TYPE: DNA
<213> ORGANISM: Homo sapiens

<400> SEQUENCE: 19
gatgcctcca gtttggaaag t                                          21

<210> SEQ ID NO 20
<211> LENGTH: 7
<212> TYPE: PRT
<213> ORGANISM: Homo sapiens

<400> SEQUENCE: 20

Asp Ala Ser Ser Leu Glu Ser
1               5

<210> SEQ ID NO 21
<211> LENGTH: 15
<212> TYPE: DNA
<213> ORGANISM: Homo sapiens

<400> SEQUENCE: 21
agttatagca tgaac                                                 15

<210> SEQ ID NO 22
<211> LENGTH: 5
<212> TYPE: PRT
<213> ORGANISM: Homo sapiens

<400> SEQUENCE: 22

Ser Tyr Ser Met Asn
1               5

<210> SEQ ID NO 23
<211> LENGTH: 33
<212> TYPE: DNA
<213> ORGANISM: Homo sapiens

<400> SEQUENCE: 23
cgggcaagtc agggcattag cagtgcttta gcc                             33

<210> SEQ ID NO 24
<211> LENGTH: 11
<212> TYPE: PRT
<213> ORGANISM: Homo sapiens

<400> SEQUENCE: 24
```

Arg Ala Ser Gln Gly Ile Ser Ser Ala Leu Ala
1               5                   10

<210> SEQ ID NO 25
<211> LENGTH: 1131
<212> TYPE: DNA
<213> ORGANISM: Homo sapiens

<400> SEQUENCE: 25

| | | | | | |
|---|---|---|---|---|---|
| gcctccacca | agggcccatc | ggtcttcccc | ctggcgccct | gctccaggag | cacctctggg | 60 |
| ggcacagcgg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacccagacc | 240 |
| tacacctgca | acgtgaatca | caagcccagc | aacaccaagg | tggacaagag | agttgagctc | 300 |
| aaaaccccac | ttggtgacac | aactcacaca | tgcccacggt | gcccagagcc | caaatcttgt | 360 |
| gacacacctc | ccccgtgccc | acggtgccca | gagcccaaat | cttgtgacac | acctcccccg | 420 |
| tgcccacggt | gcccagagcc | caaatcttgt | gacacacctc | ccccatgccc | acggtgccca | 480 |
| gcacctgaac | tcctgggagg | accgtcagtc | ttcctcttcc | ccccaaaacc | caaggatacc | 540 |
| cttatgattt | cccggacccc | tgaggtcacg | tgcgtggtgg | tggacgtgag | ccacgaagac | 600 |
| cccgaggtcc | agttcaagtg | gtacgtggac | ggcgtggagg | tgcataatgc | caagacaaag | 660 |
| ccgcgggagg | agcagttcaa | cagcacgttc | cgtgtggtca | gcgtcctcac | cgtcctgcac | 720 |
| caggactggc | tgaacggcaa | ggagtacaag | tgcaaggtct | ccaacaaagc | cctcccagcc | 780 |
| cccatcgaga | aaaccatctc | caaaaccaaa | ggacagcccc | gagaaccaca | ggtgtacacc | 840 |
| ctgcccccat | cccgggagga | gatgaccaag | aaccaggtca | gcctgacctg | cctggtcaaa | 900 |
| ggcttctacc | ccagcgacat | cgccgtggag | tgggagagca | gcgggcagcc | ggagaacaac | 960 |
| tacaacacca | cgcctcccat | gctggactcc | gacggctcct | tcttcctcta | cagcaagctc | 1020 |
| accgtggaca | agagcaggtg | gcagcagggg | aacatcttct | catgctccgt | gatgcatgag | 1080 |
| gctctgcaca | accgcttcac | gcagaagagc | ctctccctgt | ctccgggtaa | a | 1131 |

<210> SEQ ID NO 26
<211> LENGTH: 376
<212> TYPE: PRT
<213> ORGANISM: Homo sapiens

<400> SEQUENCE: 26

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Phe Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly
    370                 375

<210> SEQ ID NO 27
<211> LENGTH: 29
<212> TYPE: DNA
<213> ORGANISM: Artificial
<220> FEATURE:
<223> OTHER INFORMATION: PCR primer for human NGF

<400> SEQUENCE: 27
acaccacata tgtcatcatc ccatcccat                                    29

<210> SEQ ID NO 28
<211> LENGTH: 40
<212> TYPE: DNA
<213> ORGANISM: Artificial
<220> FEATURE:
<223> OTHER INFORMATION: PCR Primer for human NGF

<400> SEQUENCE: 28
accacaggat cctccttatg cacgacgcac agctttacgg                        40

<210> SEQ ID NO 29
<211> LENGTH: 375
<212> TYPE: DNA
<213> ORGANISM: Artificial
<220> FEATURE:
<223> OTHER INFORMATION: Nucleotide sequence encoding recombinant human met-NGF

<400> SEQUENCE: 29

```
catatgtcat catcccatcc catcttccac aggggcgaat tctcggtgtg tgacagtgtc    60
agcgtgtggg ttggggataa gaccaccgcc acagacatca aggcaagga ggtgatggtg   120 ttgggagagg tgaacattaa caacagtgta ttcaaacagt acttttttga gaccaagtgc   180
cgggacccaa atcccgttga cagcgggtgc cggggcattg actcaaagca ctggaactca   240
tattgtacca cgactcacac ctttgtcaag gcgctgacca tggatggcaa gcaggctgcc   300
tggcggttta tccggataga tacggcctgt gtgtgtgtgc tcagccgtaa agctgtgcgt   360
cgtgcataag gatcc                                                    375
```

<210> SEQ ID NO 30
<211> LENGTH: 121
<212> TYPE: PRT
<213> ORGANISM: Artificial
<220> FEATURE:
<223> OTHER INFORMATION: amino acid sequence of recombinant human met-NGF (1-120)

<400> SEQUENCE: 30

```
Met Ser Ser Ser His Pro Ile Phe His Arg Gly Glu Phe Ser Val Cys
1               5                   10                  15

Asp Ser Val Ser Val Trp Val Gly Asp Lys Thr Thr Ala Thr Asp Ile
            20                  25                  30

Lys Gly Lys Glu Val Met Val Leu Gly Glu Val Asn Ile Asn Asn Ser
        35                  40                  45

Val Phe Lys Gln Tyr Phe Phe Glu Thr Lys Cys Arg Asp Pro Asn Pro
    50                  55                  60

Val Asp Ser Gly Cys Arg Gly Ile Asp Ser Lys His Trp Asn Ser Tyr
65                  70                  75                  80

Cys Thr Thr Thr His Thr Phe Val Lys Ala Leu Thr Met Asp Gly Lys
                85                  90                  95

Gln Ala Ala Trp Arg Phe Ile Arg Ile Asp Thr Ala Cys Val Cys Val
            100                 105                 110

Leu Ser Arg Lys Ala Val Arg Arg Ala
        115                 120
```

<210> SEQ ID NO 31
<211> LENGTH: 55
<212> TYPE: DNA
<213> ORGANISM: Artificial
<220> FEATURE:
<223> OTHER INFORMATION: 5' primer sequence to generate expression vector pCFM1656 (ATCC #69576

<400> SEQUENCE: 31

```
cgatttgatt ctagaaggag gaataacata tggttaacgc gttggaattc ggtac         55
```

<210> SEQ ID NO 32
<211> LENGTH: 49
<212> TYPE: DNA
<213> ORGANISM: Artificial
<220> FEATURE:
<223> OTHER INFORMATION: 3' primer sequence to generate expression vector pCFM1656 (ATCC #69576

<400> SEQUENCE: 32

```
taaactaaga tcttcctcct tattgtatac caattgcgca accttaagc                49
```

```
<210> SEQ ID NO 33
<211> LENGTH: 24
<212> TYPE: DNA
<213> ORGANISM: Artificial
<220> FEATURE:
<223> OTHER INFORMATION: PCR primer
<220> FEATURE:
<221> NAME/KEY: Unsure
<222> LOCATION: (18)..(23)
<223> OTHER INFORMATION: n is a, c, t, or g

<400> SEQUENCE: 33
ggccggatag gcctccannn nnnt                                          24

<210> SEQ ID NO 34
<211> LENGTH: 21
<212> TYPE: DNA
<213> ORGANISM: Artificial
<220> FEATURE:
<223> OTHER INFORMATION: PCR primer

<400> SEQUENCE: 34
ggggtcaggc tggaactgag g                                             21

<210> SEQ ID NO 35
<211> LENGTH: 19
<212> TYPE: DNA
<213> ORGANISM: Artificial
<220> FEATURE:
<223> OTHER INFORMATION: PCR primer

<400> SEQUENCE: 35
tgaggacgct gaccacacg                                                19

<210> SEQ ID NO 36
<211> LENGTH: 54
<212> TYPE: DNA
<213> ORGANISM: Artificial
<220> FEATURE:
<223> OTHER INFORMATION: PCR primer

<400> SEQUENCE: 36
cagcagaagc ttctagacca ccatggacat gagggtgccc gctcagctcc tggg         54

<210> SEQ ID NO 37
<211> LENGTH: 34
<212> TYPE: DNA
<213> ORGANISM: Artificial
<220> FEATURE:
<223> OTHER INFORMATION: PCR primer

<400> SEQUENCE: 37
cttgtcgact caacactctc ccctgttgaa gctc                               34

<210> SEQ ID NO 38
<211> LENGTH: 55
<212> TYPE: DNA
<213> ORGANISM: Artificial
<220> FEATURE:
<223> OTHER INFORMATION: PCR primer

<400> SEQUENCE: 38
cagcagaagc ttctagacca ccatggagtt ggggctgtgc tgggttttcc ttgtt        55

<210> SEQ ID NO 39
<211> LENGTH: 34
<212> TYPE: DNA
<213> ORGANISM: Artificial
```

```
<220> FEATURE:
<223> OTHER INFORMATION: PCR primer

<400> SEQUENCE: 39
gcatgtcgac tcatttaccc ggagacaggg agag                               34

<210> SEQ ID NO 40
<211> LENGTH: 449
<212> TYPE: PRT
<213> ORGANISM: Homo sapiens

<400> SEQUENCE: 40
```

| Glu | Val | Gln | Leu | Val | Glu | Ser | Gly | Gly | Leu | Val | Gln | Pro | Gly | Gly |
|---|---|---|---|---|---|---|---|---|---|---|---|---|---|---|
| 1 | | | | 5 | | | | | 10 | | | | | 15 |

Ser Leu Arg Leu Ser Cys Ala Ala Ser Gly Phe Thr Leu Arg Ser Tyr
            20                  25                  30

Ser Met Asn Trp Val Arg Gln Ala Pro Gly Lys Gly Leu Glu Trp Val
        35                  40                  45

Ser Tyr Ile Ser Arg Ser Ser His Thr Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Asp Glu Asp Thr Ala Met Tyr Tyr Cys
                85                  90                  95

Ala Arg Val Tyr Ser Ser Gly Trp His Val Ser Asp Tyr Phe Asp Tyr
            100                 105                 110

Trp Gly Gln Gly Ile Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 41
<211> LENGTH: 453
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Ser Tyr
            20                  25                  30

Ser Met Asn Trp Val Arg Gln Ala Pro Gly Lys Gly Leu Glu Trp Val
        35                  40                  45

Ser Tyr Ile Ser Arg Ser Ser His Thr Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Asp Glu Asp Thr Ala Met Tyr Tyr Cys
                85                  90                  95

Ala Arg Val Tyr Ser Ser Gly Trp His Val Ser Asp Tyr Phe Asp Tyr
            100                 105                 110

Trp Gly Gln Gly Ile Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

```
Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 42
<211> LENGTH: 450
<212> TYPE: PRT
<213> ORGANISM: Homo sapiens

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Ser Tyr
            20                  25                  30

Ser Met Asn Trp Val Arg Gln Ala Pro Gly Lys Gly Leu Glu Trp Val
        35                  40                  45

Ser Tyr Ile Ser Arg Ser Ser His Thr Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Asp Glu Asp Thr Ala Met Tyr Tyr Cys
                85                  90                  95

Ala Arg Val Tyr Ser Ser Gly Trp His Val Ser Asp Tyr Phe Asp Tyr
            100                 105                 110

Trp Gly Gln Gly Ile Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Ser Leu Gly Thr Lys Thr Tyr Thr Cys Asn Val
    195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 43
<211> LENGTH: 499
<212> TYPE: PRT
<213> ORGANISM: Homo sapiens

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Ser Tyr
            20                  25                  30

Ser Met Asn Trp Val Arg Gln Ala Pro Gly Lys Gly Leu Glu Trp Val
        35                  40                  45

Ser Tyr Ile Ser Arg Ser Ser His Thr Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Asp Glu Asp Thr Ala Met Tyr Tyr Cys
                85                  90                  95

Ala Arg Val Tyr Ser Ser Gly Trp His Val Ser Asp Tyr Phe Asp Tyr
            100                 105                 110
```

```
Trp Gly Gln Gly Ile Leu Val Thr Val Ser Ser Ala Ser Thr Lys Gly
            115                 120                 125

Pro Ser Val Phe Pro Leu Ala Pro Cys Ser Arg Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Leu Gly Thr Gln Thr Tyr Thr Cys Asn Val
            195                 200                 205

Asn His Lys Pro Ser Asn Thr Lys Val Asp Lys Arg Val Glu Leu Lys
        210                 215                 220

Thr Pro Leu Gly Asp Thr Thr His Thr Cys Pro Arg Cys Pro Glu Pro
225                 230                 235                 240

Lys Ser Cys Asp Thr Pro Pro Pro Cys Pro Arg Cys Pro Glu Pro Lys
                245                 250                 255

Ser Cys Asp Thr Pro Pro Pro Cys Pro Arg Cys Pro Glu Pro Lys Ser
            260                 265                 270

Cys Asp Thr Pro Pro Pro Cys Pro Arg Cys Pro Ala Pro Glu Leu Leu
        275                 280                 285

Gly Gly Pro Ser Val Phe Leu Phe Pro Pro Lys Pro Lys Asp Thr Leu
        290                 295                 300

Met Ile Ser Arg Thr Pro Glu Val Thr Cys Val Val Val Asp Val Ser
305                 310                 315                 320

His Glu Asp Pro Glu Val Gln Phe Lys Trp Tyr Val Asp Gly Val Glu
                325                 330                 335

Val His Asn Ala Lys Thr Lys Pro Arg Glu Glu Gln Phe Asn Ser Thr
            340                 345                 350

Phe Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
        370                 375                 380

Ile Glu Lys Thr Ile Ser Lys Thr Lys Gly Gln Pro Arg Glu Pro Gln
385                 390                 395                 400

Val Tyr Thr Leu Pro Pro Ser Arg Glu Glu Met Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Ser Gly Gln Pro Glu Asn Asn Tyr Asn Thr Thr Pro
        435                 440                 445

Pro Met Leu Asp Ser Asp Gly Ser Phe Phe Leu Tyr Ser Lys Leu Thr
450                 455                 460

Val Asp Lys Ser Arg Trp Gln Gln Gly Asn Ile Phe Ser Cys Ser Val
465                 470                 475                 480

Met His Glu Ala Leu His Asn Arg Phe Thr Gln Lys Ser Leu Ser Leu
                485                 490                 495

Ser Pro Gly

<210> SEQ ID NO 44
<211> LENGTH: 214
<212> TYPE: PRT
<213> ORGANISM: Homo sapiens
```

<400> SEQUENCE: 44

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 45
<211> LENGTH: 5
<212> TYPE: PRT
<213> ORGANISM: Homo sapiens

<400> SEQUENCE: 45

```
Phe Phe Glu Thr Lys
1               5
```

<210> SEQ ID NO 46
<211> LENGTH: 9
<212> TYPE: PRT
<213> ORGANISM: Homo sapiens

<400> SEQUENCE: 46

```
Ser Ser Ser His Pro Ile Phe His Arg
1               5
```

<210> SEQ ID NO 47
<211> LENGTH: 5
<212> TYPE: PRT
<213> ORGANISM: Homo sapiens

<400> SEQUENCE: 47

```
His Trp Asn Ser Tyr
1               5
```

<210> SEQ ID NO 48
<211> LENGTH: 12

```
<212> TYPE: PRT
<213> ORGANISM: Homo sapiens

<400> SEQUENCE: 48

Asn Ser Val Glu Lys Gln Tyr Phe Phe Glu Thr Lys
1               5                   10

<210> SEQ ID NO 49
<211> LENGTH: 7
<212> TYPE: PRT
<213> ORGANISM: Homo sapiens

<400> SEQUENCE: 49

Ser Arg Lys Ala Val Arg Arg
1               5

<210> SEQ ID NO 50
<211> LENGTH: 5
<212> TYPE: PRT
<213> ORGANISM: Homo sapiens

<400> SEQUENCE: 50

Glu Val Met Val Leu
1               5

<210> SEQ ID NO 51
<211> LENGTH: 25
<212> TYPE: PRT
<213> ORGANISM: Homo sapiens

<400> SEQUENCE: 51

Ser Ser Ser His Pro Ile Phe His Arg Gly Glu Phe Ser Val Cys Asp
1               5                   10                  15

Ser Val Ser Val Trp Val Gly Asp Lys
            20                  25

<210> SEQ ID NO 52
<211> LENGTH: 20
<212> TYPE: PRT
<213> ORGANISM: Homo sapiens

<400> SEQUENCE: 52

Gln Ala Ala Trp Arg Phe Ile Arg Ile Asp Thr Ala Cys Val Cys Val
1               5                   10                  15

Leu Ser Arg Lys
            20

<210> SEQ ID NO 53
<211> LENGTH: 14
<212> TYPE: PRT
<213> ORGANISM: Homo sapiens

<400> SEQUENCE: 53

Ser Ser His Pro Ile Phe His Arg Gly Glu Phe Ser Val Cys
1               5                   10

<210> SEQ ID NO 54
<211> LENGTH: 8
<212> TYPE: PRT
<213> ORGANISM: Homo sapiens

<400> SEQUENCE: 54

Ser Ser His Pro Ile Phe His Arg
1               5
```

<210> SEQ ID NO 55
<211> LENGTH: 6
<212> TYPE: PRT
<213> ORGANISM: Homo sapiens

<400> SEQUENCE: 55

Gly Glu Phe Ser Val Cys
1               5

<210> SEQ ID NO 56
<211> LENGTH: 15
<212> TYPE: PRT
<213> ORGANISM: Homo sapiens

<400> SEQUENCE: 56

Ser Ser Ser His Pro Ile Phe His Arg Gly Glu Phe Ser Val Cys
1               5                   10                  15

<210> SEQ ID NO 57
<211> LENGTH: 16
<212> TYPE: PRT
<213> ORGANISM: Homo sapiens

<400> SEQUENCE: 57

Ile Phe His Arg Gly Glu Phe Ser Val Ala Asp Ser Val Ser Val Cys
1               5                   10                  15

<210> SEQ ID NO 58
<211> LENGTH: 16
<212> TYPE: PRT
<213> ORGANISM: Homo sapiens

<400> SEQUENCE: 58

Glu Phe Ser Val Ala Asp Ser Val Ser Val Trp Val Gly Asp Lys Cys
1               5                   10                  15

<210> SEQ ID NO 59
<211> LENGTH: 16
<212> TYPE: PRT
<213> ORGANISM: Homo sapiens

<400> SEQUENCE: 59

Asp Ser Val Ser Val Trp Val Gly Asp Lys Thr Thr Ala Thr Asp Cys
1               5                   10                  15

<210> SEQ ID NO 60
<211> LENGTH: 16
<212> TYPE: PRT
<213> ORGANISM: Homo sapiens

<400> SEQUENCE: 60

Trp Val Gly Asp Lys Thr Thr Ala Thr Asp Ile Lys Gly Lys Glu Cys
1               5                   10                  15

<210> SEQ ID NO 61
<211> LENGTH: 16
<212> TYPE: PRT
<213> ORGANISM: Homo sapiens

<400> SEQUENCE: 61

Thr Thr Ala Thr Asp Ile Lys Gly Lys Glu Val Met Val Leu Gly Cys
1               5                   10                  15

<210> SEQ ID NO 62
<211> LENGTH: 15

```
<212> TYPE: PRT
<213> ORGANISM: Homo sapiens

<400> SEQUENCE: 62

Ile Lys Gly Lys Glu Val Met Val Leu Gly Glu Val Asn Ile Asn
1               5                   10                  15

<210> SEQ ID NO 63
<211> LENGTH: 16
<212> TYPE: PRT
<213> ORGANISM: Homo sapiens

<400> SEQUENCE: 63

Val Met Val Leu Gly Glu Val Asn Ile Asn Asn Ser Val Phe Lys Cys
1               5                   10                  15

<210> SEQ ID NO 64
<211> LENGTH: 16
<212> TYPE: PRT
<213> ORGANISM: Homo sapiens

<400> SEQUENCE: 64

Glu Val Asn Ile Asn Asn Ser Val Phe Lys Gln Tyr Phe Phe Glu Cys
1               5                   10                  15

<210> SEQ ID NO 65
<211> LENGTH: 16
<212> TYPE: PRT
<213> ORGANISM: Homo sapiens

<400> SEQUENCE: 65

Asn Ser Val Phe Lys Gln Tyr Phe Phe Glu Thr Lys Ala Arg Asp Cys
1               5                   10                  15

<210> SEQ ID NO 66
<211> LENGTH: 16
<212> TYPE: PRT
<213> ORGANISM: Homo sapiens

<400> SEQUENCE: 66

Gln Tyr Phe Phe Glu Thr Lys Ala Arg Asp Pro Asn Pro Val Asp Cys
1               5                   10                  15

<210> SEQ ID NO 67
<211> LENGTH: 16
<212> TYPE: PRT
<213> ORGANISM: Homo sapiens

<400> SEQUENCE: 67

Thr Lys Ala Arg Asp Pro Asn Pro Val Asp Ser Gly Ala Arg Asp Cys
1               5                   10                  15

<210> SEQ ID NO 68
<211> LENGTH: 16
<212> TYPE: PRT
<213> ORGANISM: Homo sapiens

<400> SEQUENCE: 68

Pro Asn Pro Val Asp Ser Gly Ala Arg Asp Ile Asp Ser Lys His Cys
1               5                   10                  15

<210> SEQ ID NO 69
<211> LENGTH: 15
<212> TYPE: PRT
<213> ORGANISM: Homo sapiens
```

```
<400> SEQUENCE: 69

Ser Gly Ala Arg Asp Ile Asp Ser Lys His Trp Asn Ser Tyr Cys
1               5                   10                  15

<210> SEQ ID NO 70
<211> LENGTH: 16
<212> TYPE: PRT
<213> ORGANISM: Homo sapiens

<400> SEQUENCE: 70

Ile Asp Ser Lys His Trp Asn Ser Tyr Ala Thr Thr Thr His Thr Cys
1               5                   10                  15

<210> SEQ ID NO 71
<211> LENGTH: 16
<212> TYPE: PRT
<213> ORGANISM: Homo sapiens

<400> SEQUENCE: 71

Trp Asn Ser Tyr Ala Thr Thr Thr His Thr Phe Val Lys Ala Leu Cys
1               5                   10                  15

<210> SEQ ID NO 72
<211> LENGTH: 16
<212> TYPE: PRT
<213> ORGANISM: Homo sapiens

<400> SEQUENCE: 72

Thr Thr Thr His Thr Phe Val Lys Ala Leu Thr Met Asp Gly Lys Cys
1               5                   10                  15

<210> SEQ ID NO 73
<211> LENGTH: 16
<212> TYPE: PRT
<213> ORGANISM: Homo sapiens

<400> SEQUENCE: 73

Phe Val Lys Ala Leu Thr Met Asp Gly Lys Gln Ala Ala Trp Arg Cys
1               5                   10                  15

<210> SEQ ID NO 74
<211> LENGTH: 16
<212> TYPE: PRT
<213> ORGANISM: Homo sapiens

<400> SEQUENCE: 74

Thr Met Asp Gly Lys Gln Ala Ala Trp Arg Phe Ile Arg Ile Asp Cys
1               5                   10                  15

<210> SEQ ID NO 75
<211> LENGTH: 15
<212> TYPE: PRT
<213> ORGANISM: Homo sapiens

<400> SEQUENCE: 75

Gln Ala Ala Trp Arg Phe Ile Arg Ile Asp Thr Ala Ala Val Cys
1               5                   10                  15

<210> SEQ ID NO 76
<211> LENGTH: 16
<212> TYPE: PRT
<213> ORGANISM: Homo sapiens

<400> SEQUENCE: 76

Phe Ile Arg Ile Asp Thr Ala Ala Val Ala Val Leu Ser Arg Lys Cys
```

-continued

<210> SEQ ID NO 77
<211> LENGTH: 16
<212> TYPE: PRT
<213> ORGANISM: Homo sapiens

<400> SEQUENCE: 77

Thr Ala Ala Val Ala Val Leu Ser Arg Lys Ala Val Arg Arg Ala Cys
1               5                   10                  15

<210> SEQ ID NO 78
<211> LENGTH: 15
<212> TYPE: PRT
<213> ORGANISM: Homo sapiens

<400> SEQUENCE: 78

Cys Ala Ala Val Ala Val Leu Ser Arg Lys Ala Val Arg Arg Ala
1               5                   10                  15

<210> SEQ ID NO 79
<211> LENGTH: 125
<212> TYPE: PRT
<213> ORGANISM: homo sapien

<400> SEQUENCE: 79

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Lys Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Tyr Tyr Gly Ser Gly Thr Tyr Tyr Tyr Tyr Gly Met
            100                 105                 110

Asn Val Trp Gly Gln Gly Thr Thr Val Thr Val Ser Ser
        115                 120                 125

<210> SEQ ID NO 80
<211> LENGTH: 107
<212> TYPE: PRT
<213> ORGANISM: homo sapien

<400> SEQUENCE: 80

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ile Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp

```
                85                  90                  95

Thr Phe Gly Gln Gly Thr Lys Val Glu Ile Lys
            100                 105

<210> SEQ ID NO 81
<211> LENGTH: 127
<212> TYPE: PRT
<213> ORGANISM: homo sapien

<400> SEQUENCE: 81

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Glu Asp Tyr
            20                  25                  30

Ala Met His Trp Val Arg Gln Ala Pro Gly Lys Gly Leu Glu Trp Val
        35                  40                  45

Ser Gly Ile Ser Trp Asn Arg Gly Ile Ile Gly Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Tyr Tyr Gly Ser Gly Arg Pro Gly Tyr Phe Tyr Tyr
            100                 105                 110

Val Met Asp Val Trp Gly Gln Gly Thr Thr Val Thr Val Ser Ser
        115                 120                 125

<210> SEQ ID NO 82
<211> LENGTH: 108
<212> TYPE: PRT
<213> ORGANISM: homo sapien

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
            20                  25                  30

Phe Leu Ala Trp Phe Gln Gln Lys Pro Gly Gln Ala Pro Arg Leu Leu
        35                  40                  45

Ile Tyr Gly Ala Ser Ser Arg Ala Thr Ala Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 83
<211> LENGTH: 127
<212> TYPE: PRT
<213> ORGANISM: homo sapien

<400> SEQUENCE: 83

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
            20                  25                  30
```

```
Ala Met His Trp Val Arg Gln Ala Pro Gly Lys Gly Leu Glu Trp Val
            35                  40                  45

Ser Gly Ile Ser Trp Asn Arg Gly Ile Ile Gly Tyr Ala Gly Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Val Lys Glu Gly Tyr Tyr Gly Ser Gly Arg Pro Gly Tyr Phe Tyr Tyr
                100                 105                 110

Val Met Asp Val Trp Gly Gln Gly Thr Thr Val Thr Val Ser Ser
            115                 120                 125

<210> SEQ ID NO 84
<211> LENGTH: 108
<212> TYPE: PRT
<213> ORGANISM: homo sapien

<400> SEQUENCE: 84

Glu Ile Val Leu Thr Gln Ser Pro Gly Thr Leu Ser Leu Ser Pro Gly
 1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Val Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
                100                 105

<210> SEQ ID NO 85
<211> LENGTH: 121
<212> TYPE: PRT
<213> ORGANISM: homo sapien

<400> SEQUENCE: 85

Glu Val Gln Leu Val Glu Ser Gly Gly Gly Leu Val Gln Pro Gly Arg
 1               5                   10                  15

Ser Leu Arg Leu Ser Cys Ala Ala Ser Gly Phe Ile Phe Asp Asp Tyr
                20                  25                  30

Ala Met His Trp Val Arg Gln Ala Pro Gly Lys Gly Leu Glu Trp Val
            35                  40                  45

Ser Gly Ile Thr Trp Asn Ser Gly Ile Leu Gly Tyr Ala Asp Ser Val
 50                  55                  60

Lys Gly Arg Phe Thr Ile Ser Arg Asp Asp Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Lys Glu Glu Gly Ser Gly Arg Tyr Tyr Asn Phe Asp Tyr Trp Gly
                100                 105                 110

Gln Gly Thr Leu Val Thr Val Ser Ser
            115                 120
```

```
<210> SEQ ID NO 86
<211> LENGTH: 107
<212> TYPE: PRT
<213> ORGANISM: homo sapien

<400> SEQUENCE: 86

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105

<210> SEQ ID NO 87
<211> LENGTH: 124
<212> TYPE: PRT
<213> ORGANISM: homo sapien

<400> SEQUENCE: 87

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Asp Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Glu Gln Trp Leu Asp Pro Tyr Tyr Tyr Tyr Gly Met Asp
            100                 105                 110

Val Trp Gly Gln Gly Thr Thr Val Thr Val Ser Ser
        115                 120

<210> SEQ ID NO 88
<211> LENGTH: 107
<212> TYPE: PRT
<213> ORGANISM: homo sapien

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
                100                 105

<210> SEQ ID NO 89
<211> LENGTH: 107
<212> TYPE: PRT
<213> ORGANISM: homo sapien

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His Arg
                85                  90                  95

Thr Phe Gly Gln Gly Thr Lys Val Glu Ile Lys
                100                 105

<210> SEQ ID NO 90
<211> LENGTH: 108
<212> TYPE: PRT
<213> ORGANISM: homo sapien

<400> SEQUENCE: 90

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Gly Phe Thr Leu Thr Ile Ser Ser Leu Glu
65                  70                  75                  80

Pro Glu Asp Phe Ala Val Tyr Tyr Cys Gln Gln Tyr Asn Ser Tyr Pro
                85                  90                  95

Trp Thr Phe Gly Gln Gly Thr Lys Val Glu Ile Lys
                100                 105

<210> SEQ ID NO 91
<211> LENGTH: 107
<212> TYPE: PRT
<213> ORGANISM: homo sapien

<400> SEQUENCE: 91

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Trp
                 85                  90                  95

Thr Phe Gly Gln Gly Thr Lys Val Glu Ile Lys
            100                 105

<210> SEQ ID NO 92
<211> LENGTH: 5
<212> TYPE: PRT
<213> ORGANISM: homo sapien

<400> SEQUENCE: 92

Thr Tyr Trp Ile Gly
1               5

<210> SEQ ID NO 93
<211> LENGTH: 17
<212> TYPE: PRT
<213> ORGANISM: homo sapien

<400> SEQUENCE: 93

Ile Ile Tyr Pro Gly Asp Ser Asp Thr Lys Tyr Ser Pro Ser Phe Gln
1               5                   10                  15

Gly

<210> SEQ ID NO 94
<211> LENGTH: 16
<212> TYPE: PRT
<213> ORGANISM: homo sapien

<400> SEQUENCE: 94

Asn Tyr Tyr Gly Ser Gly Thr Tyr Tyr Tyr Tyr Gly Met Asn Val
1               5                   10                  15

<210> SEQ ID NO 95
<211> LENGTH: 11
<212> TYPE: PRT
<213> ORGANISM: homo sapien

<400> SEQUENCE: 95

Arg Ala Ser Gln Gly Ile Ser Ile Trp Leu Ala
1               5                   10

<210> SEQ ID NO 96
<211> LENGTH: 7
<212> TYPE: PRT
<213> ORGANISM: homo sapien

<400> SEQUENCE: 96

Ala Ala Ser Ser Leu Gln Ser
1               5

<210> SEQ ID NO 97
<211> LENGTH: 9
<212> TYPE: PRT
<213> ORGANISM: homo sapien

<400> SEQUENCE: 97
```

```
Gln Gln Ala Asn Ser Phe Pro Trp Thr
1               5
```

<210> SEQ ID NO 98
<211> LENGTH: 5
<212> TYPE: PRT
<213> ORGANISM: homo sapien

<400> SEQUENCE: 98

```
Asp Tyr Ala Met His
1               5
```

<210> SEQ ID NO 99
<211> LENGTH: 17
<212> TYPE: PRT
<213> ORGANISM: homo sapien

<400> SEQUENCE: 99

```
Gly Ile Ser Trp Asn Arg Gly Ile Ile Gly Tyr Ala Asp Ser Val Lys
1               5                   10                  15

Gly
```

<210> SEQ ID NO 100
<211> LENGTH: 17
<212> TYPE: PRT
<213> ORGANISM: homo sapien

<400> SEQUENCE: 100

```
Gly Tyr Tyr Gly Ser Gly Arg Pro Gly Tyr Phe Tyr Tyr Val Met Asp
1               5                   10                  15

Val
```

<210> SEQ ID NO 101
<211> LENGTH: 12
<212> TYPE: PRT
<213> ORGANISM: homo sapien

<400> SEQUENCE: 101

```
Arg Ala Ser Gln Ser Val Ser Ser Gly Phe Leu Ala
1               5                   10
```

<210> SEQ ID NO 102
<211> LENGTH: 7
<212> TYPE: PRT
<213> ORGANISM: homo sapien

<400> SEQUENCE: 102

```
Gly Ala Ser Ser Arg Ala Thr
1               5
```

<210> SEQ ID NO 103
<211> LENGTH: 9
<212> TYPE: PRT
<213> ORGANISM: homo sapien

<400> SEQUENCE: 103

```
Gln Gln Tyr Gly Ser Ser Pro Tyr Thr
1               5
```

<210> SEQ ID NO 104
<211> LENGTH: 5
<212> TYPE: PRT
<213> ORGANISM: homo sapien

```
<400> SEQUENCE: 104

Asp Tyr Ala Met His
1               5

<210> SEQ ID NO 105
<211> LENGTH: 17
<212> TYPE: PRT
<213> ORGANISM: homo sapien

<400> SEQUENCE: 105

Gly Ile Ser Trp Asn Arg Gly Ile Ile Gly Tyr Ala Gly Ser Val Lys
1               5                   10                  15

Gly

<210> SEQ ID NO 106
<211> LENGTH: 17
<212> TYPE: PRT
<213> ORGANISM: homo sapien

<400> SEQUENCE: 106

Gly Tyr Tyr Gly Ser Gly Arg Pro Gly Tyr Phe Tyr Tyr Val Met Asp
1               5                   10                  15

Val

<210> SEQ ID NO 107
<211> LENGTH: 12
<212> TYPE: PRT
<213> ORGANISM: homo sapien

<400> SEQUENCE: 107

Arg Ala Ser Gln Ser Val Ser Ser Ser Tyr Leu Ala
1               5                   10

<210> SEQ ID NO 108
<211> LENGTH: 7
<212> TYPE: PRT
<213> ORGANISM: homo sapien

<400> SEQUENCE: 108

Val Ala Ser Ser Arg Ala Thr
1               5

<210> SEQ ID NO 109
<211> LENGTH: 9
<212> TYPE: PRT
<213> ORGANISM: homo sapien

<400> SEQUENCE: 109

Gln Gln Tyr Gly Ser Ser Pro Tyr Thr
1               5

<210> SEQ ID NO 110
<211> LENGTH: 5
<212> TYPE: PRT
<213> ORGANISM: homo sapien

<400> SEQUENCE: 110

Asp Tyr Ala Met His
1               5

<210> SEQ ID NO 111
<211> LENGTH: 17
<212> TYPE: PRT
<213> ORGANISM: homo sapien
```

```
<400> SEQUENCE: 111

Gly Ile Thr Trp Asn Ser Gly Ile Leu Gly Tyr Ala Asp Ser Val Lys
1               5                   10                  15
Gly

<210> SEQ ID NO 112
<211> LENGTH: 11
<212> TYPE: PRT
<213> ORGANISM: homo sapien

<400> SEQUENCE: 112

Glu Gly Ser Gly Arg Tyr Tyr Asn Phe Asp Tyr
1               5                   10

<210> SEQ ID NO 113
<211> LENGTH: 12
<212> TYPE: PRT
<213> ORGANISM: homo sapien

<400> SEQUENCE: 113

Arg Ala Ser Gln Ser Val Ser Ser Tyr Leu Ala
1               5                   10

<210> SEQ ID NO 114
<211> LENGTH: 7
<212> TYPE: PRT
<213> ORGANISM: homo sapien

<400> SEQUENCE: 114

Gly Ala Ser Ser Arg Ala Thr
1               5

<210> SEQ ID NO 115
<211> LENGTH: 8
<212> TYPE: PRT
<213> ORGANISM: homo sapien

<400> SEQUENCE: 115

Gln Gln Tyr Gly Ser Ser Tyr Thr
1               5

<210> SEQ ID NO 116
<211> LENGTH: 5
<212> TYPE: PRT
<213> ORGANISM: homo sapien

<400> SEQUENCE: 116

Asp Tyr Gly Met Asn
1               5

<210> SEQ ID NO 117
<211> LENGTH: 17
<212> TYPE: PRT
<213> ORGANISM: homo sapien

<400> SEQUENCE: 117

Asp Ile Asn Trp Asn Gly Gly Ser Thr Gly Tyr Ala Asp Ser Val Lys
1               5                   10                  15
Gly

<210> SEQ ID NO 118
<211> LENGTH: 15
<212> TYPE: PRT
```

<213> ORGANISM: homo sapien

<400> SEQUENCE: 118

Glu Gln Trp Leu Asp Pro Tyr Tyr Tyr Tyr Gly Met Asp Val
1               5                   10                  15

<210> SEQ ID NO 119
<211> LENGTH: 11
<212> TYPE: PRT
<213> ORGANISM: homo sapien

<400> SEQUENCE: 119

Arg Ala Ser Gln Gly Ile Ser Ser Trp Leu Ala
1               5                   10

<210> SEQ ID NO 120
<211> LENGTH: 7
<212> TYPE: PRT
<213> ORGANISM: homo sapien

<400> SEQUENCE: 120

Ala Ala Ser Ser Leu Gln Ser
1               5

<210> SEQ ID NO 121
<211> LENGTH: 9
<212> TYPE: PRT
<213> ORGANISM: homo sapien

<400> SEQUENCE: 121

Gln Gln Tyr Asn Ser Tyr Pro Trp Thr
1               5

<210> SEQ ID NO 122
<211> LENGTH: 11
<212> TYPE: PRT
<213> ORGANISM: homo sapien

<400> SEQUENCE: 122

Arg Ala Ser Gln Gly Val Ser Ser Tyr Leu Ala
1               5                   10

<210> SEQ ID NO 123
<211> LENGTH: 7
<212> TYPE: PRT
<213> ORGANISM: homo sapien

<400> SEQUENCE: 123

Asp Ala Ser Asn Arg Ala Thr
1               5

<210> SEQ ID NO 124
<211> LENGTH: 9
<212> TYPE: PRT
<213> ORGANISM: homo sapien

<400> SEQUENCE: 124

Gln Gln Arg Ser Asn Trp His Arg Thr
1               5

<210> SEQ ID NO 125
<211> LENGTH: 12
<212> TYPE: PRT
<213> ORGANISM: homo sapien

<400> SEQUENCE: 125

```
Arg Ala Ser Gln Ser Val Ser Ser Tyr Leu Ala
1               5                   10

<210> SEQ ID NO 126
<211> LENGTH: 7
<212> TYPE: PRT
<213> ORGANISM: homo sapien

<400> SEQUENCE: 126

Gly Ala Ser Ser Arg Ala Thr
1               5

<210> SEQ ID NO 127
<211> LENGTH: 9
<212> TYPE: PRT
<213> ORGANISM: homo sapien

<400> SEQUENCE: 127

Gln Gln Tyr Asn Ser Tyr Pro Trp Thr
1               5

<210> SEQ ID NO 128
<211> LENGTH: 11
<212> TYPE: PRT
<213> ORGANISM: homo sapien

<400> SEQUENCE: 128

Arg Ala Ser Gln Ser Val Ser Ser Tyr Leu Ala
1               5                   10

<210> SEQ ID NO 129
<211> LENGTH: 7
<212> TYPE: PRT
<213> ORGANISM: homo sapien

<400> SEQUENCE: 129

Asp Ala Ser Asn Arg Ala Thr
1               5

<210> SEQ ID NO 130
<211> LENGTH: 9
<212> TYPE: PRT
<213> ORGANISM: homo sapien

<400> SEQUENCE: 130

Gln Gln Arg Ser Asn Trp Pro Trp Thr
1               5

<210> SEQ ID NO 131
<211> LENGTH: 108
<212> TYPE: PRT
<213> ORGANISM: homo sapien

<400> SEQUENCE: 131

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
```

```
                65                  70                  75                  80
Pro Glu Asp Phe Ala Val Tyr Tyr Cys Gln Gln Tyr Gly Ser Ser Pro
                    85                  90                  95
Tyr Thr Phe Gly Gln Gly Thr Lys Leu Glu Ile Lys
                100                 105
```

<210> SEQ ID NO 132
<211> LENGTH: 11
<212> TYPE: PRT
<213> ORGANISM: homo sapien

<400> SEQUENCE: 132

```
Arg Ala Ser Gln Gly Val Ser Ser Tyr Leu Ala
1               5                   10
```

<210> SEQ ID NO 133
<211> LENGTH: 7
<212> TYPE: PRT
<213> ORGANISM: homo sapien

<400> SEQUENCE: 133

```
Gly Ala Ser Ser Arg Ala Thr
1               5
```

<210> SEQ ID NO 134
<211> LENGTH: 9
<212> TYPE: PRT
<213> ORGANISM: homo sapien

<400> SEQUENCE: 134

```
Gln Gln Tyr Gly Ser Ser Pro Tyr Thr
1               5
```

<210> SEQ ID NO 135
<211> LENGTH: 120
<212> TYPE: PRT
<213> ORGANISM: homo sapien

<400> SEQUENCE: 135

```
Ser Ser Ser His Pro Ile Phe His Arg Gly Glu Phe Ser Val Cys Asp
1               5                   10                  15
Ser Val Ser Val Trp Val Gly Asp Lys Thr Thr Ala Thr Asp Ile Lys
                20                  25                  30
Gly Lys Glu Val Met Val Leu Gly Glu Val Asn Ile Asn Asn Ser Val
                35                  40                  45
Phe Lys Gln Tyr Phe Phe Glu Thr Lys Cys Arg Asp Pro Asn Pro Val
        50                  55                  60
Asp Ser Gly Cys Arg Gly Ile Asp Ser Lys His Trp Asn Ser Tyr Cys
65                  70                  75                  80
Thr Thr Thr His Thr Phe Val Lys Ala Leu Thr Met Asp Gly Lys Gln
                85                  90                  95
Ala Ala Trp Arg Phe Ile Arg Ile Asp Thr Ala Cys Val Cys Val Leu
                100                 105                 110
Ser Arg Lys Ala Val Arg Arg Ala
                115                 120
```

<210> SEQ ID NO 136
<211> LENGTH: 120
<212> TYPE: PRT
<213> ORGANISM: mus musculus

<400> SEQUENCE: 136

```
Ser Ser Thr His Pro Val Phe His Met Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Thr Val Leu Ala Glu Val Asn Ile Asn Asn Ser Val
        35                  40                  45

Phe Arg Gln Tyr Phe Glu Thr Lys Cys Arg Ala Ser Asn Pro Val
    50                  55                  60

Glu Ser Gly Cys Arg Gly Ile Asp Ser Lys His Trp Asn Ser Tyr Cys
65                  70                  75                  80

Thr Thr Thr His Thr Phe Val Lys Ala Leu Thr Thr Asp Glu Lys Gln
                85                  90                  95

Ala Ala Trp Arg Phe Ile Arg Ile Asp Thr Ala Cys Val Cys Val Leu
            100                 105                 110

Ser Arg Lys Ala Thr Arg Ala
        115                 120
```

<210> SEQ ID NO 137
<211> LENGTH: 126
<212> TYPE: PRT
<213> ORGANISM: homo sapien

<400> SEQUENCE: 137

```
His Ser Asp Pro Ala Arg Arg His Ser Asp Pro Ala Arg Arg Gly Glu
1               5                   10                  15

Leu Ser Val Cys Asp Ser Ile Ser Glu Trp Val Thr Ala Ala Asp Lys
            20                  25                  30

Lys Thr Ala Val Asp Met Ser Gly Gly Thr Val Thr Val Leu Glu Lys
        35                  40                  45

Val Pro Val Ser Lys Gly Gln Leu Lys Gln Tyr Phe Tyr Glu Thr Lys
    50                  55                  60

Cys Asn Pro Met Gly Tyr Thr Lys Glu Gly Cys Arg Gly Ile Asp Lys
65                  70                  75                  80

Arg His Trp Asn Ser Gln Cys Arg Thr Thr Gln Ser Tyr Val Arg Ala
                85                  90                  95

Leu Thr Met Asp Ser Lys Lys Arg Ile Gly Trp Arg Phe Ile Arg Ile
            100                 105                 110

Asp Thr Ser Cys Val Cys Thr Leu Thr Ile Lys Arg Gly Arg
        115                 120                 125
```

<210> SEQ ID NO 138
<211> LENGTH: 119
<212> TYPE: PRT
<213> ORGANISM: homo sapien

<400> SEQUENCE: 138

```
Tyr Ala Glu His Lys Ser His Arg Gly Glu Tyr Ser Val Cys Asp Ser
1               5                   10                  15

Glu Ser Leu Trp Val Thr Asp Lys Ser Ser Ala Ile Asp Ile Arg Gly
            20                  25                  30

His Gln Val Thr Val Leu Gly Glu Ile Lys Thr Gly Asn Ser Pro Val
        35                  40                  45

Lys Gln Tyr Phe Tyr Glu Thr Arg Cys Lys Glu Ala Arg Pro Val Lys
    50                  55                  60

Asn Gly Cys Arg Gly Ile Asp Asp Lys His Trp Asn Ser Gln Cys Lys
65                  70                  75                  80
```

```
Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
            100                 105                 110

Ser Arg Lys Ile Gly Arg Thr
        115

<210> SEQ ID NO 139
<211> LENGTH: 104
<212> TYPE: PRT
<213> ORGANISM: Homo sapiens

<400> SEQUENCE: 139

Val Asn Val Ser Phe Pro Ala Ser Val Gln Leu His Thr Ala Val Glu
1               5                   10                  15

Met His His Trp Cys Ile Pro Phe Ser Val Asp Gly Gln Pro Ala Pro
            20                  25                  30

Ser Leu Arg Trp Leu Phe Asn Gly Ser Val Leu Asn Glu Thr Ser Phe
        35                  40                  45

Ile Phe Thr Glu Phe Leu Glu Pro Ala Ala Asn Glu Thr Val Arg His
    50                  55                  60

Gly Cys Leu Arg Leu Asn Gln Pro Thr His Val Asn Asn Gly Asn Tyr
65                  70                  75                  80

Thr Leu Leu Ala Ala Asn Pro Phe Gly Gln Ala Ser Ala Ser Ile Met
                85                  90                  95

Ala Ala Phe Met Asp Asn Pro Phe
            100

<210> SEQ ID NO 140
<211> LENGTH: 103
<212> TYPE: PRT
<213> ORGANISM: Homo sapiens

<400> SEQUENCE: 140

Leu Thr Val His Phe Ala Pro Thr Ile Thr Phe Leu Glu Ser Pro Thr
1               5                   10                  15

Ser Asp His His Trp Cys Ile Pro Phe Thr Val Lys Gly Asn Pro Lys
            20                  25                  30

Pro Ala Leu Gln Trp Phe Tyr Asn Gly Ala Ile Leu Asn Glu Ser Lys
        35                  40                  45

Tyr Ile Cys Thr Lys Ile His Val Thr Asn His Thr Glu Tyr His Gly
    50                  55                  60

Cys Leu Gln Leu Asp Asn Pro Thr His Met Asn Asn Gly Asp Tyr Thr
65                  70                  75                  80

Leu Ile Ala Lys Asn Glu Tyr Gly Lys Asp Glu Lys Gln Ile Ser Ala
                85                  90                  95

His Phe Met Gly Trp Pro Gly
            100

<210> SEQ ID NO 141
<211> LENGTH: 102
<212> TYPE: PRT
<213> ORGANISM: Homo sapiens

<400> SEQUENCE: 141

Leu Thr Val Tyr Tyr Pro Pro Arg Val Val Ser Leu Glu Glu Pro Glu
1               5                   10                  15

Leu Arg Leu Glu His Cys Ile Glu Phe Val Val Arg Gly Asn Pro Pro
            20                  25                  30
```

```
Pro Thr Leu His Trp Leu His Asn Gly Gln Pro Leu Arg Glu Ser Lys
        35              40                  45

Ile Ile His Val Glu Tyr Tyr Gln Glu Gly Glu Ile Ser Glu Gly Cys
    50              55                  60

Leu Leu Phe Asn Lys Pro Thr His Tyr Asn Asn Gly Asn Tyr Thr Leu
65              70                  75                      80

Ile Ala Lys Asn Pro Leu Gly Thr Ala Asn Gln Thr Ile Asn Gly His
                85                  90                  95

Phe Leu Lys Trp Pro Phe
            100
```

HUMAN ANTI-NGF NEUTRALIZING ANTIBODIES AS SELECTIVE NGF PATHWAY INHIBITORS

This application is a continuation application of U.S. patent application Ser. No. 10/891,658, filed Jul. 15, 2004, now U.S. Pat. No. 7,601,818, issued Oct. 13, 2009, which claims the benefit of priority to U.S. provisional application Ser. No. 60/487,431, filed Jul. 15, 2003. The disclosures of all these applications are incorporated by reference herein.

This application is also related to U.S. Ser. No. 11/767,326, filed Jun. 22, 2007, now U.S. Pat. No. 7,795,413, issued Sep. 14, 2010, which is a divisional application of U.S. Ser. No. 10/891,658. The disclosure of this application is incorporated by reference herein.

The sequence listing is filed with the application in electronic format only and is incorporated by reference herein. The sequence listing text file "02-1240-F-CON.SeqList.txt" was created on Nov. 25, 2008, and is 79,116 bytes in size.

FIELD OF THE INVENTION

The invention relates to human monoclonal antibodies that bind nerve growth factor (NGF). Compositions and methods for treating pain and pain-related disorders are also described.

BACKGROUND OF THE INVENTION

Every day, more than two million people in the United States are incapacitated by chronic pain (Jessell and Kelly, 1991, "Pain and Analgesia" in PRINCIPLES OF NEURAL SCIENCE, $3^{rd}$ Ed., (Kandel, Schwartz, and Jessell, ed.), Elsevier, N.Y.). Unfortunately, current treatments for pain are only partially effective, and many of these treatments themselves cause debilitating or dangerous side effects. For example, although non-steroidal anti-inflammatory drugs ("NSAIDs") such as aspirin, ibuprofen, and indomethacin are moderately effective against inflammatory pain, they are also renal toxins, and high doses tend to cause gastrointestinal irritation, ulceration, bleeding, and mental confusion. Patients treated with opioids also frequently experience confusion, and long-term opioid use is associated with tolerance and dependence. Local anesthetics such as lidocaine and mexiletine simultaneously inhibit pain and cause loss of normal sensation.

Pain is a perception based on signals received from the environment and transmitted and interpreted by the nervous system (for review, see Millan, 1999, *Prog. Neurobiol.* 57:1-164). Noxious stimuli such as heat and touch cause specialized sensory receptors in the skin to send signals to the central nervous system ("CNS"). This process is called nociception, and the peripheral sensory neurons that mediate it are nociceptors. Depending on the strength of the signal from the nociceptor(s) and the abstraction and elaboration of that signal by the CNS, a person may or may not experience a noxious stimulus as painful. When one's perception of pain is properly calibrated to the intensity of the stimulus, pain serves its intended protective function. However, certain types of tissue damage cause a phenomenon, known as hyperalgesia or pronociception, in which relatively innocuous stimuli are perceived as intensely painful because the person's pain thresholds have been lowered. Both inflammation and nerve damage can induce hyperalgesia. Persons afflicted with inflammatory conditions, such as sunburn, osteoarthritis, colitis, carditis, dermatitis, myositis, neuritis, collagen vascular diseases (which include rheumatoid arthritis and lupus) and the like, often experience enhanced sensations of pain. Similarly, trauma, surgery, amputation, abscess, causalgia, collagen vascular diseases, demyelinating diseases, trigeminal neuralgia, cancer, chronic alcoholism, stroke, thalamic pain syndrome, diabetes, herpes infections, acquired immune deficiency syndrome ("AIDS"), toxins and chemotherapy cause nerve injuries that result in excessive pain.

As the mechanisms by which nociceptors transduce external signals under normal and hyperalgesic conditions become better understood, processes implicated in hyperalgesia can be targeted to inhibit the lowering of the pain threshold and thereby lessen the amount of pain experienced.

Neurotrophic factors have been shown to play significant roles in the transmission of physiologic and pathologic pain. Nerve growth factor (NGF) appears to be particularly important (for review, see McMahon, 1996, *Phil. Trans. R. Soc. Lond.* 351:431-40; and Apfel, 2000, *The Clinical Journal of Pain* 16:S7-S11). Both local and systemic administration of NGF have been shown to elicit hyperalgesia and allodynia (Lewin et al., 1994, *Eur. J. Neurosci.* 6:1903-1912). Intravenous infusion of NGF in humans produces a whole body myalgia while local administration evokes injection site hyperalgesia and allodynia in addition to the systemic effects (Apfel et al., 1998, *Neurology* 51:695-702). There is also a considerable body of evidence implicating endogenous NGF in conditions in which pain is a prominent feature. For example, NGF is upregulated in dorsal root ganglion (DRG) Schwann cells for at least 2 months following peripheral nerve injury and increased levels have been reported in the joints of animals suffering from a variety of arthritis models (e.g., Aloe et al., 1993, *Growth Factors* 9:149-155). In humans, NGF levels are elevated in synovial fluid from patients with rheumatoid or other types of arthritis (e.g., Aloe et al., 1992, *Arthritis and Rheumatism* 35:351-355). Furthermore, it has been demonstrated that antagonism of NGF function prevents hyperalgesia and allodynia in models of neuropathic and chronic inflammatory pain. For example, in animal models of neuropathic pain (e.g. nerve trunk or spinal nerve ligation) systemic injection of neutralizing antibodies to NGF prevents both allodynia and hyperalgesia (Ramer et al., 1999, *Eur. J. Neurosci.* 11:837-846; and Ro et al., 1999, *Pain* 79:265-274). Examples of anti-NGF antibodies known in the art include, for example, PCT Publication Nos. WO 01/78698, WO 01/64247, WO 02/096458, and WO 2004/032870; U.S. Pat. Nos. 5,844,092, 5,877,016, and 6,153,189; Hongo et al., 2000, *Hybridoma* 19:215-227; Hongo et al., 1993, *Cell. Mol. Biol.* 13:559-568; and GenBank Accession Nos. U39608, U39609, L17078, or L17077.

Clearly, there is a need for new safe and effective treatments for pain, particularly by targeting small molecule mediators or exacerbators of pain such as NGF.

SUMMARY OF THE INVENTION

This invention provides novel human monoclonal antibodies that are therapeutically useful for managing pain. Specifically, the invention provides monoclonal antibodies that bind to nerve growth factor (NGF). Preferably, the monoclonal antibodies are human monoclonal antibodies and neutralize biological activities of NGF and are useful for ameliorating the effects of NGF-mediated pain responses. Also provided by the invention are cells that produce, and most preferably, secrete into cell culture media the monoclonal antibodies of the invention. In addition to their use for treating and managing pain, the antibodies of the invention are useful for treating neuropathic and inflammatory pain-related responses.

The invention further provides fusion proteins comprising the sequence of an antibody Fc region and one or more sequences identified as SEQ ID NO: 10, SEQ ID NO: 12, SEQ ID NO: 14, SEQ ID NO: 16, SEQ ID NO: 18, SEQ ID NO: 20, SEQ ID NO: 22, and SEQ ID NOs: 79-130. Such molecules can be prepared using methods as described, for example, in International Patent Application, Publication No. WO 00/24782, which is incorporated by reference. Such molecules can be expressed, for example, in mammalian cells (e.g. Chinese Hamster Ovary cells) or bacterial cells (e.g. *E. coli* cells).

In certain aspects, the invention provides antibodies, preferably monoclonal antibodies, most preferably human antibodies and human monoclonal antibodies, comprising a heavy chain and a light chain, wherein the heavy chain comprises an amino acid sequence as set forth in SEQ ID NO: 2, SEQ ID NO: 4, or SEQ ID NO: 6, or an antigen-binding or an immunologically functional immunoglobulin fragment thereof and the variable region of the heavy chain comprises an amino acid sequence as set forth in SEQ ID NO: 10, or an antigen-binding or an immunologically functional immunoglobulin fragment thereof. Preferably, the heavy chain comprises an amino acid sequence as set forth in SEQ ID NO: 4.

In certain aspects, the invention provides antibodies, preferably human antibodies, and more preferably monoclonal antibodies, most preferably human monoclonal antibodies, comprising a heavy chain and a light chain, wherein the heavy chain comprises an heavy chain constant region selected from the group consisting of IgG1, IgG2, IgG3, IgG4, IgM, IgA and IgE heavy chain constant regions or any allelic variation thereof (as discussed in Kabat et al., 1991, Sequences of Proteins of Immunological Interest, Fifth Edition, U.S. Department of Health and Human Services, NIH Publication No. 91-3242), included herein by reference, and the variable region of the heavy chain comprises an amino acid sequence as set forth in SEQ ID NO: 10, or an antigen-binding or an immunologically functional immunoglobulin fragment thereof. Preferably, an antibody of the invention comprises an amino acid sequence of the IgG2 heavy chain constant region as set forth in SEQ ID NO: 4 or an antigen-binding or an immunologically functional immunoglobulin fragment thereof.

In certain aspects, the invention provides antibodies, preferably human antibodies, and more preferably monoclonal antibodies, most preferably human monoclonal antibodies, comprising a heavy chain and a light chain, wherein the light chain comprises an amino acid sequence as set forth in SEQ ID NO: 8 or an antigen-binding or an immunologically functional immunoglobulin fragment thereof and the light chain variable region comprises an amino acid sequence as set forth in SEQ ID NO: 12, or an antigen-binding or an immunologically functional immunoglobulin fragment thereof.

In certain aspects, antibodies of the invention comprise a heavy chain and a light chain, wherein the variable region of the heavy chain comprises an amino acid sequence as set forth in SEQ ID NO: 10, or an antigen-binding or an immunologically functional immunoglobulin fragment thereof. In other aspects, the light chain variable region comprises an amino acid sequence as set forth in SEQ ID NO: 12, or an antigen-binding or an immunologically functional immunoglobulin fragment thereof. In additional aspects, the heavy chain comprises an amino acid sequence as set forth in any of SEQ ID NO: 14, SEQ ID NO: 18, or SEQ ID NO: 20, or an antigen-binding or an immunologically functional immunoglobulin fragment thereof. In still further aspects, the light chain comprises an amino acid sequence as set forth in any of SEQ ID NO: 16, 20, 24, or an antigen-binding or an immunologically functional immunoglobulin fragment thereof.

The invention also provides antibodies that bind specifically to NGF, wherein the heavy chain comprises a variable region comprising an amino acid sequence as set forth in SEQ ID NO: 10, or an antigen-binding or an immunologically functional immunoglobulin fragment thereof, and the light chain comprises a variable region comprising an amino acid sequence as set forth in SEQ ID NO: 12, or an antigen-binding or an immunologically functional immunoglobulin fragment thereof.

The invention further provides isolated human antibodies that bind specifically to NGF, wherein the antibodies comprise:

(a) a heavy chain having a heavy chain variable region comprising an amino acid sequence as set forth in SEQ ID NO: 79, or an antigen-binding or an immunologically functional immunoglobulin fragment thereof, and a light chain having a light chain variable region comprising an amino acid sequence as set forth in SEQ ID NO: 80, or an antigen-binding or an immunologically functional immunoglobulin fragment thereof;

(b) a heavy chain having a heavy chain variable region comprising an amino acid sequence as set forth in SEQ ID NO: 81, or an antigen-binding or an immunologically functional immunoglobulin fragment thereof, and a light chain having a light chain variable region comprising an amino acid sequence as set forth in SEQ ID NO: 82, or an antigen-binding or an immunologically functional immunoglobulin fragment thereof;

(c) a heavy chain having a heavy chain variable region comprising an amino acid sequence as set forth in SEQ ID NO: 83, or an antigen-binding or an immunologically functional immunoglobulin fragment thereof, and a light chain having a light chain variable region comprising an amino acid sequence as set forth in SEQ ID NO: 84, or an antigen-binding or an immunologically functional immunoglobulin fragment thereof, or (d) a heavy chain having a heavy chain variable region comprising an amino acid sequence as set forth in SEQ ID NO: 86, or an antigen-binding or an immunologically functional immunoglobulin fragment thereof, and a light chain having a light chain variable region comprising an amino acid sequence as set forth in SEQ ID NO: 87, or an antigen-binding or an immunologically functional immunoglobulin fragment thereof.

In certain aspects, the invention also provides antibodies, comprising a heavy chain and a light chain, wherein the heavy chain comprises a heavy chain variable region, and wherein the heavy chain variable region comprises a sequence that has at least 75%, preferably 80%, more preferably at least 85%, even more preferably at least 90%, 91%, 92%, 93%, 94%, 95%, 96%, 97%, 98%, and most preferably about 99%, identity to the amino acid sequence as set forth in SEQ ID NO: 10, and wherein the light chain comprises a light chain variable region, and wherein the light chain variable region comprises a sequence that has at least 80%, preferably at least 85%, more preferably at least 90%, 91%, 92%, 93%, 94%, 95%, 96%, 97%, 98%, and most preferably about 99%, identity to the amino acid sequence as set forth in SEQ ID NO: 12, wherein the antibody binds specifically to NGF.

The invention also provides antibodies that bind specifically to NGF, wherein the heavy chain comprises an amino acid sequence as set forth in SEQ ID NO: 14 or an antigen-binding or an immunologically functional immunoglobulin fragment thereof, and the light chain comprises an amino acid sequence as set forth in SEQ ID NO: 16, or an antigen-binding or an immunologically functional immunoglobulin fragment thereof.

In certain aspects, the invention provides antibodies, comprising a heavy chain and a light chain, wherein the heavy chain comprises a heavy chain variable region, and wherein the heavy chain variable region comprises a sequence that has at least 75%, preferably 80%, more preferably at least 85%, even more preferably at least 90%, 91%, 92%, 93%, 94%, 95%, 96%, 97%, 98%, and most preferably about 99%, identity to the amino acid sequence as set forth in any of SEQ ID NO: 14, SEQ ID NO: 18, or SEQ ID NO: 22, and wherein the light chain comprises a light chain variable region, and wherein the light chain variable region comprises an amino acid sequence that has as least 80%, preferably at least 85%, more preferably at least 90%, 91%, 92%, 93%, 94%, 95%, 96%, 97%, 98%, and most preferably about 99%, identity to the amino acid sequence as set forth in SEQ ID NO: 16, wherein the antibody binds specifically to NGF.

The invention also provides single chain antibodies, single chain Fv antibodies, F(ab) antibodies, F(ab)' antibodies and (Fab')$_2$ antibodies.

In particular aspects, the invention provides a light chain comprising an amino acid sequence as set forth in SEQ ID NO: 16, or an antigen-binding or an immunologically functional immunoglobulin fragment thereof.

In addition, the invention provides a heavy chain comprising an amino acid sequence as set forth in any of SEQ ID NO: 14, SEQ ID NO: 18, or SEQ ID NO: 22, or an antigen-binding or an immunologically functional immunoglobulin fragment thereof.

The invention also relates to isolated human antibodies that specifically bind NGF, wherein the antibody comprises: (a) human heavy chain framework regions, a human heavy chain CDR1 region, a human heavy chain CDR2 region, and a human heavy chain CDR3 region; and (b) human light chain framework regions, a human light chain CDR1 region, a human light chain CDR2 region, and a human light chain CDR3 region. In certain aspects, the human heavy chain CDR1 region can be the heavy chain CDR1 region of the monoclonal antibody (mAb) designated 4D4 as shown in SEQ ID NO:22 and the human light chain CDR1 region can be the light chain CDR1 region of mAb 4D4 as shown in SEQ ID NO:24. In other aspects, the human heavy chain CDR2 region can be the heavy chain CDR2 region of mAb 4D4 as shown in SEQ ID NO: 18 and the human light chain CDR2 region can be the light chain CDR2 region of mAb 4D4 as shown in SEQ ID NO:20. In still other aspects, the human heavy chain CDR3 region is the heavy chain CDR3 region of mAb 4D4 as shown in SEQ ID NO: 14, and the human light chain CDR3 region is the light chain CDR3 region of mAb 4D4 as shown in SEQ ID NO:16.

The invention also provides isolated human antibodies that specifically bind nerve growth factor, comprising a heavy chain and a light chain, wherein the heavy chain comprises a heavy chain variable region comprising an amino acid sequence as set forth in SEQ ID NO: 10, SEQ ID NO: 79, SEQ ID NO: 81, SEQ ID NO: 83, SEQ ID NO: 85, or SEQ ID NO: 87, or an antigen-binding or immunologically functional immunoglobulin fragments thereof.

The invention further provides isolated human antibodies that specifically bind NGF, comprising a heavy chain and a light chain, wherein the light chain comprises a light chain variable region comprising an amino acid sequence as set forth in SEQ ID NO: 12, SEQ ID NO: 80, SEQ ID NO: 82, SEQ ID NO: 84, SEQ ID NO: 86, SEQ ID NO: 88, SEQ ID NO: 89, SEQ ID NO: 90, SEQ ID NO: 91, or SEQ ID NO: 131, or antigen-binding or an immunologically functional immunoglobulin fragments thereof.

The antibodies of the invention are characterized by the capacity to antagonize at least one in vitro and/or in vivo activity associated with NGF polypeptides. Preferably, the invention provides isolated anti-human NGF human antibodies with high affinity binding to NGF polypeptides, wherein the antibodies bind to a human NGF polypeptide and dissociates from the human NGF polypeptide with a dissociation constant $(K_D)$ of about $50\times10^{-12}$ M or less, as determined using KinExA, or which inhibit NGF induced survival in an in vitro neutralization assay with an $IC_{50}$ of about $1\times10^{-8}$ M or less.

In a preferred embodiment, the invention provides an isolated anti-human NGF human antibody that has the following characteristics:

a) inhibits NGF induced survival in an in vitro neutralization assay with an $IC_{50}$ of about $1\times10^{-9}$ M or less;

b) has a heavy chain CDR3 comprising the amino acid sequence of SEQ ID NO:14; and c) has a light chain CDR3 comprising the amino acid sequence of SEQ ID NO:16.

The invention also provides isolated human antibodies or an antigen-binding or immunologically functional immunoglobulin fragments thereof that bind specifically to NGF with high affinity, wherein said antibodies or fragments dissociate from a human NGF polypeptide with a $K_D$ of about $1\times10^{-9}$ or less and neutralizes human NGF bioactivity in a standard in vitro assay with an $IC_{50}$ of about $1\times10^{-8}$ M or less, and wherein the antibodies or fragments comprise a heavy chain variable region comprising:

a) a CDR1 region comprising an amino acid sequence of the formula:

$$a^1a^2a^3a^4a^5$$

wherein:

$a^1$ is a polar hydrophilic amino acid residue; $a^2$ is an aromatic amino acid residue; $a^3$ is a aliphatic, polar hydrophobic, aromatic amino acid residue; $a^4$ is a neutral hydrophobic or aliphatic amino acid residue; and $a^5$ is a aliphatic or polar hydrophilic amino acid residue;

b) a CDR2 region comprising an amino acid sequence of the formula:

$$b^1b^2b^3b^4b^5b^6b^7b^8b^9b^{10}b^{11}b^{12}b^{13}b^{14}b^{15}b^{16}b^{17}$$

wherein:

$b^1$ is a aliphatic, polar hydrophobic, or aromatic amino acid residue; $b^2$ is an aliphatic hydrophobic amino acid residue; $b^3$ is a polar hydrophilic or aromatic amino acid residue; $b^4$ is a polar hydrophilic, hydrophobic, or aromatic amino acid residue; $b^5$-$b^9$ are independently polar hydrophilic or aliphatic amino acid residues; $b^{10}$ is a polar hydrophilic, aromatic, or aliphatic amino acid residue; $b^{11}$ is an aromatic or hydrophobic amino acid residue; $b^{12}$ is an aliphatic hydrophobic or polar hydrophilic amino acid residue; $b^{13}$ is an aliphatic, hydrophobic or polar hydrophilic amino acid residue; $b^{14}$ and $b^{16}$ are independently polar hydrophilic amino acid residues; $b^{15}$ is an aliphatic or aromatic hydrophobic amino acid residue; and $b^{17}$ is an aliphatic acidic amino acid residue; and c) a CDR3 region comprising an amino acid sequence of the formula:

$$c^1c^2c^3c^4c^5c^6c^7c^8c^9c^{10}c^{11}c^{12}c^{13}c^{14}c^{15}c^{16}c^{17}$$

wherein:

$c^1$ is absent or an aliphatic amino acid residue; $c^2$ is absent or a polar hydrophilic or an aromatic hydrophobic amino acid residue; $c^3$ and $c^4$ are independently absent or a polar hydrophilic, aromatic hydrophobic, or aliphatic amino acid residues; $c^5$ is absent or a polar hydrophilic, aliphatic or an aromatic amino acid residue; $c^6$ is absent or a polar hydrophilic or aliphatic amino acid residue; $c^7$ is a polar hydrophilic or an aliphatic amino acid residue; $c^8$ is a polar hydrophilic, hydrophobic or an aromatic amino acid residue; $c^9$ is a polar hydrophilic, aliphatic or an aromatic hydrophobic amino acid residue; $c^{10}$ polar hydrophilic, aromatic or an a liphatic hydrophobic amino acid residue; $c^{11}$-$c^{13}$ are independently polar hydrophilic or aromatic hydrophobic amino acid residues; $c^{14}$ is an aliphatic or aromatic hydrophobic amino acid residue; $c^{15}$ is a polar hydrophilic or neutral hydrophobic amino acid residue; $c^{16}$ is absent or a polar hydrophilic amino acid residue; and $c^{17}$ is an aromatic hydrophobic or aliphatic hydrophobic amino acid residue.

In one aspect, $a^1$ is a polar hydrophilic amino acid residue; $a^2$ is an aromatic hydrophobic amino acid residue; $a^3$ is an aliphatic hydrophobic amino acid residue; $a^4$ is a neutral hydrophobic; $a^5$ is a polar hydrophilic amino acid residue; $b^1$ is a aliphatic or aromatic amino acid residue; $b^2$ is Ile; $b^3$ is a polar hydrophilic amino acid residue; $b^4$ is a polar hydrophilic or aromatic amino acid residue; $b^5$-$b^9$ are independently polar hydrophilic or aliphatic amino acid residues; $b^{10}$ is an aliphatic amino acid residue; $b^{11}$ is Tyr; $b^{12}$ is an aliphatic hydrophobic amino acid residue; $b^{13}$ is an aliphatic or polar hydrophilic amino acid residue; $b^{14}$ and $b^{16}$ are independently polar hydrophilic amino acid residues; and $b^{15}$ is an aliphatic hydrophobic amino acid residue; $b^{17}$ is an aliphatic acidic amino acid residue; $c^1$ is absent or an aliphatic amino acid residue; $c^2$ is absent or a polar hydrophilic or an aromatic hydrophobic amino acid residue; $c^3$ and $c^4$ are independently absent or a polar hydrophilic, aromatic hydrophobic, or aliphatic amino acid residues; $c^5$ is absent or a polar hydrophilic amino acid residue; $C^6$ is absent or a polar hydrophilic or aliphatic amino acid residue; $c^7$ is a polar hydrophilic or an aliphatic amino acid residue; $c^8$ is a polar hydrophilic, hydrophobic or an aromatic amino acid residue; $c^9$ is a polar hydrophilic, aliphatic or an aromatic hydrophobic amino acid residue; $c^{10}$ is a polar hydrophilic, aromatic or an a liphatic hydrophobic amino acid residue; $c^{11}$-$c^{13}$ are independently polar hydrophilic or aromatic hydrophobic amino acid residues; $c^{14}$ is an aliphatic or aromatic hydrophobic amino acid residue; $c^{15}$ is a polar hydrophilic or neutral hydrophobic amino acid residue; $c^{16}$ is absent or a polar hydrophilic amino acid residue; and $c^{17}$ is an aromatic hydrophobic or aliphatic hydrophobic amino acid residue.

In a particular aspect, $a^1$ is Ser, Asp, or Thr; $a^2$ is Tyr; $a^3$ is Ala, Ser, Trp, or Gly; $a^4$ is Met or Ile; $a^5$ is His, Gly, or Asn; $b^1$ is Tyr, Gly, Ile, or Asp; $b^2$ is Ile; $b^3$ is Ser, Thr, Tyr, or Asn; $b^4$ is Trp, Arg, or Pro; $b^5$ is Ser, Asn, or Gly; $b^6$ is Ser, Arg, Asp, or Gly; $b^7$ is Ser, His, or Gly; $b^8$ is Ser, Ile, Asp, or Thr; $b^9$ is Leu, Ile, or Thr; $b^{10}$ is Gly, Lys, or Phe; $b^{11}$ is Tyr; $b^{12}$ is Ala or Ser; $b^{13}$ is Asp, Gly, or Pro; $b^{14}$ is Ser; $b^{15}$ is Val or Phe; $b^{16}$ is Lys or Gln; $b^{17}$ is Gly; $c^1$ is absent or an aliphatic amino acid residue; $c^2$ is absent or Tyr; $c^3$ and $c^4$ are independently absent, Tyr, Asn, Val, or Glu; $c^5$ is absent, Ser, Gly, or Trp; $c^6$ is absent, Ser, Gly, Glu, or Leu; $c^7$ is Gly, Arg, or Asp; $c^8$ is Trp, Pro, Ser, or Thr; $c^9$ is His, Gly, or Tyr; $c^{10}$ is Val, Tyr, or Arg; $c^{11}$-$c^{13}$ are independently Ser, Phe, Tyr, Asp, or Asn; $c^{14}$ is Phe, Val, or Gly; $c^{15}$ is Met or Asp; $c^{16}$ is absent, Asp, or Asn; and $c^{17}$ is Tyr or Val.

In another particular aspect, $a^1$ is Ser or Asp; $a^2$ is Tyr; $a^3$ is Ala or Ser; $a^4$ is Met or Ile; $a^5$ is His or Asn; $b^1$ is Tyr or Gly; $b^2$ is Ile; $b^3$ is Ser, Thr, Tyr, or Asn; $b^4$ is Trp, Arg, or Pro; $b^5$ is Ser or Asn; $b^6$ is Ser or Arg; $b^7$ is His or Gly; $b^8$ is Ile or Thr; $b^9$ is Leu, Ile, or Thr; $b^{10}$ is Gly or Phe; $b^{11}$ is Tyr; $b^{12}$ is Ala or Ser; $b^{13}$ is Asp or Gly; $b^{14}$ is Ser; $b^{15}$ is Val or Phe; $b^{16}$ is Lys or Gln; $b^{17}$ is Gly; $c^1$ is absent or Gly; $c^2$ is absent or Tyr; $c^3$ and $c^4$ are independently absent, Tyr, Gly, or Val; $c^5$ is absent or Ser; $c^6$ is Ser or Gly; $c^7$ is Gly or Arg; $c^8$ is Trp or Pro; $c^9$ is His, Gly, or Tyr; $c^{10}$ is Val or Tyr; $c^{11}$-$c^{13}$ are independently Ser, Tyr, Phe, or Asp; $c^{14}$ is Phe or Val; $c^{15}$ is Met or Asp; $c^{16}$ is absent or Asp; and $c^{17}$ is Tyr or Val.

In other particular aspects:
a) the heavy chain CDR1 has an amino acid sequence as set forth in SEQ ID NO: 22, the heavy chain CDR2 has an amino acid sequence as set forth in SEQ ID NO: 18, and the heavy chain CDR 3 has an amino acid sequence as set forth in SEQ ID NO: 14;
b) the heavy chain CDR1 has an amino acid sequence as set forth in SEQ ID NO: 92, the heavy chain CDR2 has an amino acid sequence as set forth in SEQ ID NO: 93, and the heavy chain CDR 3 has an amino acid sequence as set forth in SEQ ID NO: 94;
c) the heavy chain CDR1 has an amino acid sequence as set forth in SEQ ID NO: 98, the heavy chain CDR2 has an amino acid sequence as set forth in SEQ ID NO: 99, and the heavy chain CDR 3 has an amino acid sequence as set forth in SEQ ID NO: 100;
d) the heavy chain CDR1 has an amino acid sequence as set forth in SEQ ID NO: 104, the heavy chain CDR2 has an amino acid sequence as set forth in SEQ ID NO: 105, and the heavy chain CDR 3 has an amino acid sequence as set forth in SEQ ID NO: 106;
e) the heavy chain CDR1 has an amino acid sequence as set forth in SEQ ID NO: 110, the heavy chain CDR2 has an amino acid sequence as set forth in SEQ ID NO: 111, and the heavy chain CDR 3 has an amino acid sequence as set forth in SEQ ID NO: 112; and
f) the heavy chain CDR1 has an amino acid sequence as set forth in SEQ ID NO: 116, the heavy chain CDR2 has an amino acid sequence as set forth in SEQ ID NO: 117, and the heavy chain CDR 3 has an amino acid sequence as set forth in SEQ ID NO: 118.

The invention also provides an isolated human antibody or an antigen-binding or an immunologically functional immunoglobulin fragment thereof that binds specifically to NGF, wherein the antibody or fragment comprises a light chain variable region comprising:
a) a CDR1 region comprising an amino acid sequence of the formula:

$$a^1a^2a^3a^4a^5a^6a^7a^8a^9a^{10}a^{11}a^{12}$$

wherein:
$a^1$ is a polar hydrophilic amino acid residue; $a^2$, $a^{11}$ and $a^{12}$ are independently aliphatic or hydrophobic amino acid residues; $a^3$, $a^5$, $a^7$ and $a^8$ are independently aliphatic, polar hydrophilic, or hydrophobic amino acid residues; $a^4$ is a polar hydrophilic amino acid residue; $a^6$ is an aliphatic or hydrophobic amino acid residue; $a^9$ is absent, or an aliphatic or polar hydrophilic amino acid residue; and $a^{10}$ is an aliphatic, aromatic, or hydrophobic amino acid residue;

b) a CDR2 region comprising an amino acid sequence of the formula:

$$b^1b^2b^3b^4b^5b^6b^7$$

wherein:
$b^1$ is a aliphatic, polar hydrophobic, or hydrophobic amino acid residue; $b^2$ is an aliphatic or hydrophobic amino acid residue; $b^3$ and $b^4$ are independently polar hydrophilic, aliphatic or hydrophobic amino acid residues; $b^5$ is a polar hydrophilic or aliphatic hydrophobic amino acid residues; $b^6$ is a polar hydrophilic or aliphatic hydrophobic amino acid residue; and $b^7$ is a polar hydrophilic amino acid residue; and c) a CDR3 region comprising an amino acid sequence of the formula:

$$c^1c^2c^3c^4c^5c^6c^7c^8c^9c^{10}c^{11}c^{12}c^{13}c^{14}c^{15}c^{16}c^{17}$$

wherein:

$c^1$ and $c^2$ are independently polar hydrophilic amino acid residues; $c^3$ is a polar hydrophilic, aliphatic or hydrophobic amino acid residue; $c^4$, $c^5$ and $c^6$ are independently aliphatic, polar hydrophilic, or hydrophobic amino acid residues; $c^7$ is absent or a polar hydrophilic or an aliphatic hydrophobic amino acid residue; $c^8$ is a polar hydrophilic or hydrophobic amino acid residue; and $c^9$ is a polar hydrophilic amino acid residue, and wherein said antibody or fragment dissociates from a human NGF polypeptide with a $K_D$ of about $1 \times 10^{-9}$ or less and neutralizes human NGF bioactivity in a standard in vitro assay with an $IC_{50}$ of about $1 \times 10^{-8}$ M or less.

In one aspect, $a^1$, $a^3$, $a^4$, $a^7$ and $a^8$ are independently polar hydrophilic amino acid residues; $a^2$, $a^6$, $a^{11}$ and $a^{12}$ are independently aliphatic hydrophobic amino acid residues; $a^5$ is a polar hydrophilic or aliphatic amino acid residue; $a^9$ is absent, or an aliphatic or polar hydrophilic amino acid residue; $a^{10}$ is an aliphatic or aromatic amino acid residue; $b^1$ is a aliphatic, polar hydrophobic, or hydrophobic amino acid residue; $b^2$ is an aliphatic hydrophobic amino acid residue; $b^3$, $b^4$ and $b^7$ are independently polar hydrophilic amino acid residues; $b^5$ and $b^6$ are independently polar hydrophilic or aliphatic hydrophobic amino acid residues; $c^1$ and $c^2$ are independently polar hydrophilic amino acid residues; $c^3$ is a polar hydrophilic, aliphatic or hydrophobic amino acid residue; $c^4$, $c^5$, and $c^6$ are independently aliphatic, polar hydrophilic, or hydrophobic amino acid residues; $c^7$ is absent or an aliphatic hydrophobic amino acid residue; $c^8$ is a hydrophobic amino acid residue; and $c^9$ is a polar hydrophilic amino acid residue.

In a particular aspect, $a^1$, $a^3$, $a^4$, and $a^7$ are Arg, Ser, Gln, and Ser, respectively; $a^2$ is Ala; $a^5$ is Gly or Ser; $a^8$ is Ser or Ile; $a^9$ is absent, Ser, or Gly; $a^{10}$ is Ala, Tyr, Trp or Phe; $b^1$ is Asp, Gly, Ala, or Val; $b^2$ and $b^3$ are Ala and Ser, respectively; $b^4$ is Ser or Asn; $b^5$ is Leu or Arg; $b^6$ is Glu, Ala, or Gln; $b^7$ is Ser or Thr; $c^1$ and $c^2$ are Gln; $c^3$ is Phe, Tyr, Arg, or Ala; $c^4$ is Asn, Gly, or Ser; $c^5$ is Ser or Asn; $c^6$ is Tyr, Ser, Trp, or Phe; $c^7$ is absent, Pro, or His; $c^8$ is Leu, Trp, Tyr, or Arg; and $c^9$ is Thr.

In another particular aspect, $a^1$, $a^2$, $a^3$, $a^4$, and $a^7$ are Arg, Ala, Ser, Gln, and Ser, respectively; $a^5$ is Gly or Ser; $a^8$ is Ser or Ile; $a^9$ is absent, Ser, or Gly; $a^{10}$ is Ala or Tyr; $b^1$ is Asp or Gly; $b^2$ and $b^3$ are Ala and Ser, respectively; $b^4$ is Ser or Asn; $b^5$ is Leu or Arg; $b^6$ is Glu, Ala, or Gln; $b^7$ is Ser or Thr; $c^1$ and $c^2$ are Gln; $c^3$ is Phe, Tyr, Arg, or Ala; $c^4$ is Asn, Gly, or Ser; $c^5$ is Ser or Asn; $c^6$ is Tyr, Ser, Trp, or Phe; $c^7$ is absent, Pro, or His; $c^8$ is Leu, Trp, Tyr, or Arg; and $c^9$ is Thr.

In other particular aspects:
a) the light chain CDR1 has an amino acid sequence as set forth in SEQ ID NO: 24, the light chain CDR2 has an amino acid sequence as set forth in SEQ ID NO: 20, and the light chain CDR 3 has an amino acid sequence as set forth in SEQ ID NO: 16;
b) the light chain CDR1 has an amino acid sequence as set forth in SEQ ID NO: 95, the light chain CDR2 has an amino acid sequence as set forth in SEQ ID NO: 96, and the light chain CDR 3 has an amino acid sequence as set forth in SEQ ID NO: 97;
c) the light chain CDR1 has an amino acid sequence as set forth in SEQ ID NO: 101, the light chain CDR2 has an amino acid sequence as set forth in SEQ ID NO: 102, and the light chain CDR 3 has an amino acid sequence as set forth in SEQ ID NO: 103;
d) the light chain CDR1 has an amino acid sequence as set forth in SEQ ID NO: 107, the light chain CDR2 has an amino acid sequence as set forth in SEQ ID NO: 108, and the light chain CDR 3 has an amino acid sequence as set forth in SEQ ID NO: 109;
e) the light chain CDR1 has an amino acid sequence as set forth in SEQ ID NO: 113, the light chain CDR2 has an amino acid sequence as set forth in SEQ ID NO: 114, and the light chain CDR 3 has an amino acid sequence as set forth in SEQ ID NO: 115;
f) the light chain CDR1 has an amino acid sequence as set forth in SEQ ID NO: 119, the light chain CDR2 has an amino acid sequence as set forth in SEQ ID NO: 120, and the light chain CDR 3 has an amino acid sequence as set forth in SEQ ID NO: 121;
g) the light chain CDR1 has an amino acid sequence as set forth in SEQ ID NO: 122, the light chain CDR2 has an amino acid sequence as set forth in SEQ ID NO: 123, and the light chain CDR 3 has an amino acid sequence as set forth in SEQ ID NO: 124;
h) the light chain CDR1 has an amino acid sequence as set forth in SEQ ID NO: 125, the light chain CDR2 has an amino acid sequence as set forth in SEQ ID NO: 126, and the light chain CDR 3 has an amino acid sequence as set forth in SEQ ID NO: 127;
i) the light chain CDR1 has an amino acid sequence as set forth in SEQ ID NO: 128, the light chain CDR2 has an amino acid sequence as set forth in SEQ ID NO: 129, and the light chain CDR 3 has an amino acid sequence as set forth in SEQ ID NO: 130; and
j) the light chain CDR1 has an amino acid sequence as set forth in SEQ ID NO: 132, the light chain CDR2 has an amino acid sequence as set forth in SEQ ID NO: 133, and the light chain CDR 3 has an amino acid sequence as set forth in SEQ ID NO: 134.

Also part of the invention are polynucleotide sequences that encode the novel anti-human NGF human antibodies, vectors comprising the polynucleotide sequences encoding anti-human NGF human antibodies, host cells transformed with vectors incorporating polynucleotides that encode the anti-human NGF human antibodies, formulations comprising anti-human NGF human antibodies and methods of making and using the same.

The invention also provides methods for detecting the level of NGF in a biological sample, comprising the step of contacting the sample with an antibody of the invention or antigen-binding fragment thereof. An anti-NGF antibody of the invention may be employed in any known assay method, such as competitive binding assays, direct and indirect sandwich assays, immunoprecipitation assays and enzyme-linked immunosorbent assays (ELISA) (See, Sola, 1987, *Monoclonal Antibodies: A Manual of Techniques*, pp. 147-158, CRC Press, Inc.) for the detection and quantitation of NGF. The antibodies can bind NGF with an affinity that is appropriate for the assay method being employed.

In addition, the invention provides methods for treating a disease associated with increased production of NGF, or increased sensitivity to NGF comprising the step of administering a pharmaceutically effective amount of a pharmaceutical composition comprising at least one antibody of the invention or an antigen-binding or an immunologically functional immunoglobulin fragment thereof to an individual in need thereof.

Specific preferred embodiments of the invention will become evident from the following more detailed description of certain preferred embodiments and the claims.

BRIEF DESCRIPTION OF THE DRAWINGS

FIG. 2 depicts graphs that demonstrate VR1 expression stimulated by human NGF activity and neutralization of NGF activity in DRG neuron based neutralization bioassays by an anti-NGF monoclonal antibody (4D4) purified from the hybridoma conditioned media.

FIG. 5 shows anti-NGF CDR1 heavy chain alignment and percent identity for the 14D10 (SEQ ID NO: 98), 6H9 (SEQ ID NO: 104), 7H2 (SEQ ID NO: 110), 4G6 (SEQ ID NO: 116), 14D11 (SEQ ID NO: 92), and 4D4 (SEQ ID NO: 22) antibodies.

FIG. 6 shows anti-NGF CDR2 heavy chain alignment and percent identity for the 14D10 (SEQ ID NO: 99), 6H9 (SEQ ID NO: 105), 7H2 (SEQ ID NO: 111), 4G6 (SEQ ID NO: 117), 14D11 (SEQ ID NO: 93), and 4D4 (SEQ ID NO: 18) antibodies.

FIG. 7 shows anti-NGF CDR3 heavy chain alignment and percent identity for the 14D10 (SEQ ID NO: 100), 6H9 (SEQ ID NO: 106), 7H2 (SEQ ID NO: 112), 4G6 (SEQ ID NO: 118), 14D11 (SEQ ID NO: 94), and 4D4 (SEQ ID NO: 14) antibodies.

FIG. 8 shows anti-NGF CDR1 light chain alignment and percent identity for the 14D10 (SEQ ID NO: 95), 6H9 (SEQ ID NO: 107), 7H2 (SEQ ID NO: 113), 4G6a (SEQ ID NO: 119), 4G6b (SEQ ID NO: 122), 4G6c (SEQ ID NO: 125), 4G6d (SEQ ID NO: 128), 4G6e (SEQ ID NO: 132), 14D11 (SEQ ID NO: 95), and 4D4 (SEQ ID NO: 24) antibodies (4G6a is referred to in various Figures as 20031028340; 4G6b is referred to in various Figures as 20031028351; 4G6c is referred to in various Figures as 20031071526; 4G6d is referred to in various Figures as 20031028344; 4G6e is referred to in various Figures as 20031000528).

FIG. 9 shows anti-NGF CDR2 light chain alignment and percent identity for the 14D10 (SEQ ID NO: 96), 6H9 (SEQ ID NO: 108), 7H2 (SEQ ID NO: 114), 4G6a (SEQ ID NO: 120), 4G6b (SEQ ID NO: 123), 4G6c (SEQ ID NO: 126), 4G6d (SEQ ID NO: 129), 4G6e (SEQ ID NO: 133), 14D11 (SEQ ID NO: 96), and 4D4 (SEQ ID NO: 20) antibodies (4G6a is referred to in various Figures as 20031028340; 4G6b is referred to in various Figures as 20031028351; 4G6c is referred to in various Figures as 20031071526; 4G6d is referred to in various Figures as 20031028344; 4G6e is referred to in various Figures as 20031000528).

FIG. 10 shows anti-NGF CDR3 light chain alignment and percent identity for the 14D10 (SEQ ID NO: 97), 6H9 (SEQ ID NO: 109), 7H2 (SEQ ID NO: 115), 4G6a (SEQ ID NO: 121), 4G6b (SEQ ID NO: 124), 4G6c (SEQ ID NO: 127), 4G6d (SEQ ID NO: 130), 4G6e (SEQ ID NO: 134), 14D11 (SEQ ID NO: 97), and 4D4 (SEQ ID NO: 16) antibodies (4G6a is referred to in various Figures as 20031028340; 4G6b is referred to in various Figures as 20031028351; 4G6c is referred to in various Figures as 20031071526; 4G6d is referred to in various Figures as 20031028344; 4G6e is referred to in various Figures as 20031000528).

FIG. 11 shows anti-NGF light chain alignment and percent identity for the 14D10 (SEQ ID NO: 82), 6H9 (SEQ ID NO: 84), 7H2 (SEQ ID NO: 86), 4G6a (SEQ ID NO: 88), 4G6b (SEQ ID NO: 89), 4G6c (SEQ ID NO: 90), 4G6d (SEQ ID NO: 91), 4G6e (SEQ ID NO: 131), 14D11 (SEQ ID NO: 80), and 4D4 (SEQ ID NO: 12) antibodies (4G6a is referred to in various Figures as 20031028340; 4G6b is referred to in various Figures as 20031028351; 4G6c is referred to in various Figures as 20031071526; 4G6d is referred to in various Figures as 20031028344; 4G6e is referred to in various Figures as 20031000528).

FIG. 12 shows anti-NGF heavy chain alignment and percent identity for the 4D4 (SEQ ID NO: 10), 4G6 (SEQ ID NO: 87), 14D10 (SEQ ID NO: 81), 14D11 (SEQ ID NO: 79), 7H2 (SEQ ID NO: 85), and 6H9 (SEQ ID NO: 83) antibodies.

DETAILED DESCRIPTION OF CERTAIN PREFERRED EMBODIMENTS

Figure 1:
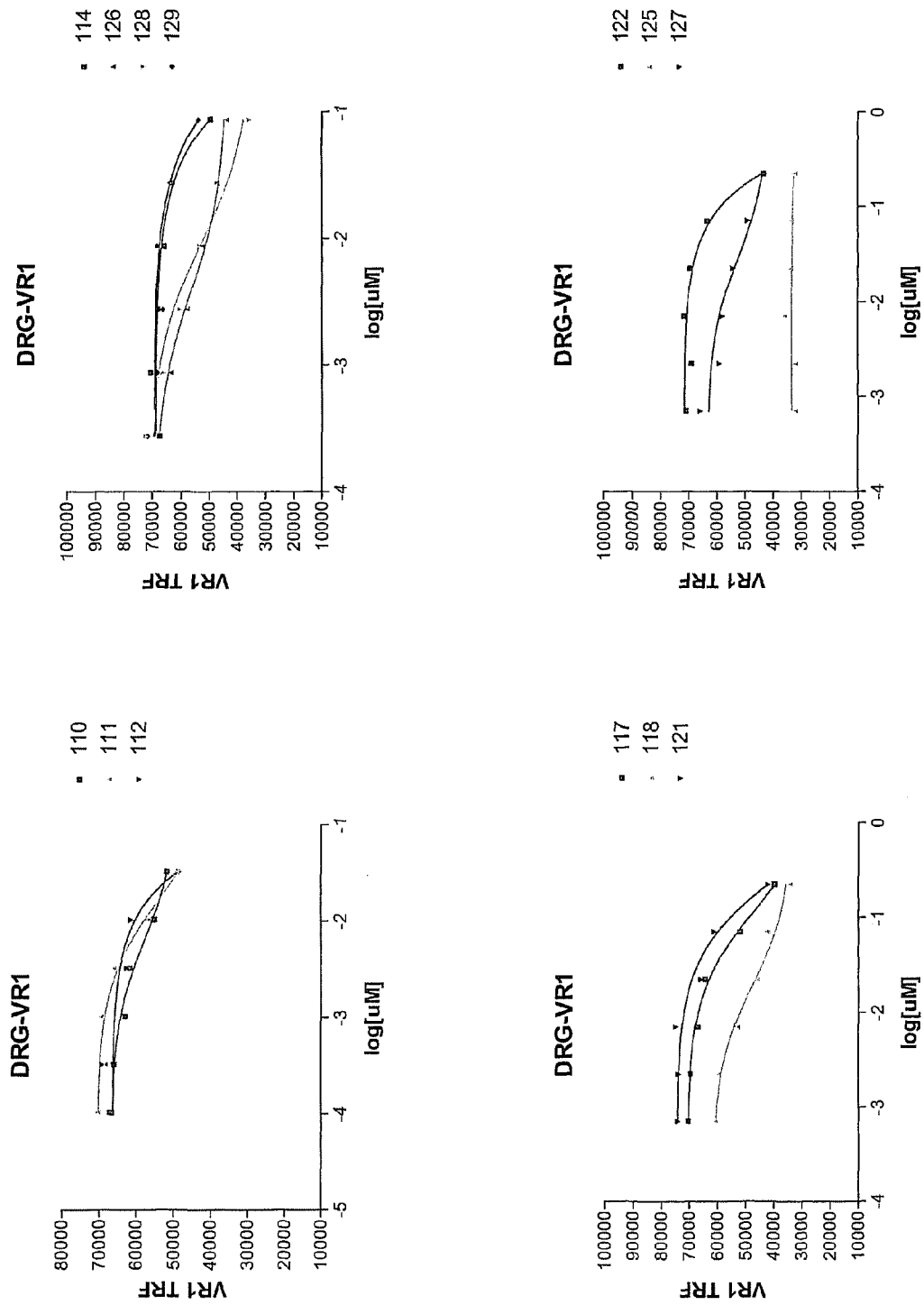
FIGS. 1(a)-(b) depict graphs that demonstrate neutralization of NGF activity in the DRG neuron based neutralization bioassay by 4D4 monoclonal antibodies purified from the hybridoma conditioned media.
Figure 1:
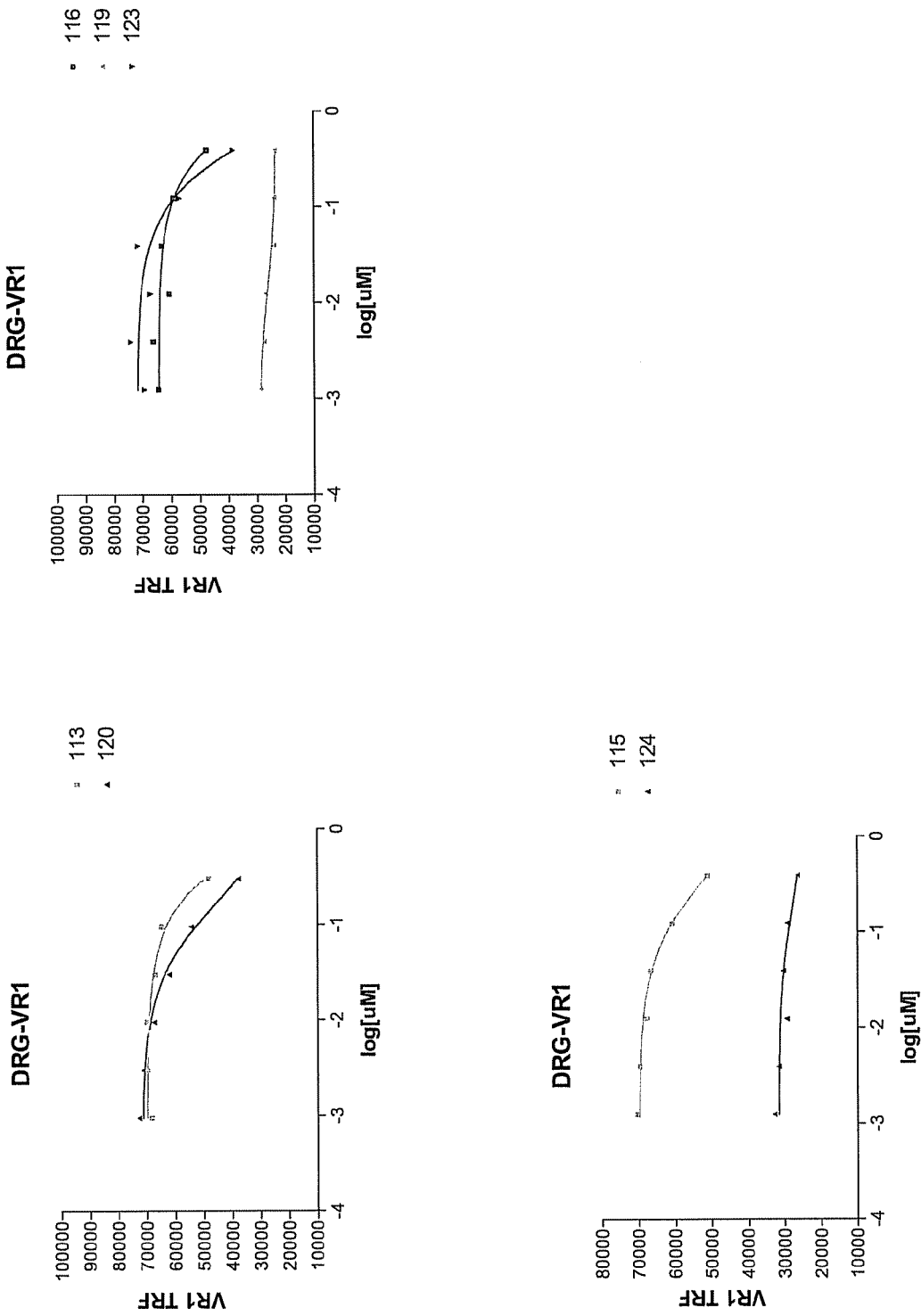

The section headings used herein are for organizational purposes only and are not to be construed as limiting the subject matter described. All references cited in this application are expressly incorporated by reference herein for any purpose.

Definitions

Conventional techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well known and commonly used in the art. Similarly, conventional techniques may be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings: The phrases "biological property", "biological characteristic", and the term "activity" in reference to an antibody of the present invention are used interchangeably herein and include, but are not limited to, epitope affinity and specificity (e.g., anti-human NGF human antibody binding to human NGF), ability to antagonize the activity of the targeted polypeptide (e.g., NGF activity), the in vivo stability of the antibody, and the immunogenic properties of the antibody. Other identifiable biological properties or characteristics of an antibody recognized in the art include, for example, cross-reactivity, (i.e., with non-human homologs of the targeted polypeptide, or with other proteins or tissues, generally), and ability to preserve high expression levels of protein in mammalian cells. The aforementioned properties or characteristics can be observed or measured using art-recognized techniques including, but not limited to ELISA, competitive ELISA, surface plasmon resonance analysis, in vitro and in vivo neutralization assays (e.g., Example 2), and immunohistochemistry with tissue sections from different sources including human, primate, or any other source as the need may be. Particular activities and biological properties of anti-human NGF human antibodies are described in further detail in the Examples below.

The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "isolated protein" referred to herein means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of synthetic origin, or any combination thereof. Preferably, the isolated protein is substantially free from proteins or polypeptides or other contaminants that are found in its natural environment that would interfere with its use (therapeutic, diagnostic, prophylactic, research or otherwise).

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present.

The terms "polypeptide" or "protein" means molecules having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass anti-NGF antibodies, or sequences that have deletions from, additions to, and/or substitutions of one or more amino acid of an anti-NGF antibody.

The term "polypeptide fragment" refers to a polypeptide that has an amino-terminal deletion, a carboxyl-terminal deletion, and/or an internal deletion. In certain embodiments, fragments are at least 5 to about 500 amino acids long. It will be appreciated that in certain embodiments, fragments are at least 5, 6, 8, 10, 14, 20, 50, 70, 100, 110, 150, 200, 250, 300, 350, 400, or 450 amino acids long. Particularly useful polypeptide fragments include functional domains, including binding domains. In the case of an anti-NGF antibody, useful fragments include but are not limited to a CDR region, a variable domain of a heavy or light chain, a portion of an antibody chain or just its variable region including two CDRs, and the like.

The term "specific binding agent" refers to a natural or non-natural molecule that specifically binds to a target. Examples of specific binding agents include, but are not limited to, proteins, peptides, nucleic acids, carbohydrates, and lipids. In certain embodiments, a specific binding agent is an antibody.

The term "specific binding agent to NGF" refers to a specific binding agent that specifically binds any portion of NGF. In certain embodiments, a specific binding agent to NGF is an antibody that binds specifically to NGF.

The term "immunologically functional immunoglobulin fragment" as used herein refers to a polypeptide fragment that contains at least the CDRs of the immunoglobulin heavy and light chains. An immunologically functional immunoglobulin fragment of the invention is capable of binding to an antigen. In preferred embodiments, the antigen is a ligand that specifically binds to a receptor. In these embodiments, binding of an immunologically functional immunoglobulin fragment of the invention prevents binding of the ligand to its receptor, interrupting the biological response resulting from ligand binding to the receptor. Preferably, an immunologically functional immunoglobulin fragment of the invention binds specifically to NGF. Most preferably, the fragment binds specifically to human NGF.

The term "naturally-occurring" as used herein and applied to an object refers to the fact that the object can be found in nature. For example, a polypeptide or polynucleotide sequence that is present in an organism (including viruses) that can be isolated from a source in nature and that has not been intentionally modified by man is naturally-occurring.

The term "operably linked" means that the components to which the term is applied are in a relationship that allows them to carry out their inherent functions under suitable conditions. For example, a control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can effect expression, processing or intracellular localization of coding sequences to which they are ligated. The nature of such control sequences may depend upon the host organism. In particular embodiments, control sequences for prokaryotes may include a promoter, ribosomal binding site, and transcription termination sequence. In other particular embodiments, control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Said modifications include base modifications such as bromuridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "oligonucleotide" referred to herein includes naturally occurring, and modified nucleotides linked together by naturally occurring, and/or non-naturally occurring oligonucleotide linkages. Oligonucleotides are a polynucleotide subset comprising members that are generally single-stranded and have a length of 200 nucleotides or fewer. In certain embodiments, oligonucleotides are 10 to 60 nucleotides in length. In certain embodiments, oligonucleotides are 12, 13, 14, 15, 16, 17, 18, 19, or to 40 nucleotides in length. Oligonucleotides may be single stranded or double stranded, e.g. for use in the construction of a genetic mutant. Oligonucleotides of the invention may be sense or antisense oligonucleotides with reference to a protein-coding sequence.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, *Nucl. Acids Res.*, 14:9081; Stec et al., 1984, *J. Am. Chem. Soc.*, 106:6077; Stein et al., 1988, *Nucl. Acids Res.*, 16:3209; Zon et al., 1991, *Anti-Cancer Drug Design*, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, *Chemical Reviews*, 90:543, the disclosures of which are hereby incorporated by reference for any purpose. An oligonucleotide can include a detectable label to enable detection of the oligonucleotide or hybridization thereof.

The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell. and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The phrase "recombinant host cell" (or simply "host cell") includes a cell into which a recombinant expression vector has been introduced. It will be understood by those of skill in the art that such terms are intended to refer not only to the particular subject cell but to the progeny of such a cell. Because certain modifications may occur in succeeding generations due to either mutation or environmental influences, such progeny may not, in fact, be identical to the parent cell. but are still included within the scope of the term "host cell" as used herein. A wide variety of host expression systems can be used to express the antibodies of the present invention including bacterial, yeast, baculoviral and mammalian expression systems (as well as phage display expression systems). An example of a suitable bacterial expression vector is pUC19. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook et al., 2001, MOLECULAR CLONING, A LABORATORY MANUAL, Cold Spring Harbor Laboratories, Ausubel, F. M. et al. (eds.) Current Protocols in Molecular Biology, Greene Publishing Associates, (1989) and in U.S. Pat. No. 4,816,397 to Boss et al.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "identity," as known in the art, refers to a relationship between the sequences of two or more polypeptide molecules or two or more nucleic acid molecules, as determined by comparing the sequences thereof. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is used in the art with regard to a related concept, but in contrast to "identity," "similarity" refers to a measure of relatedness, which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Identity and similarity of related nucleic acids and polypeptides can be readily calculated by known methods. Such methods include, but are not limited to, those described in COMPUTATIONAL MOLECULAR BIOLOGY, (Lesk, A. M., ed.), 1988, Oxford University Press, New York; BIOCOMPUTING: INFORMATICS AND GENOME PROJECTS, (Smith, D. W., ed.), 1993, Academic Press, New York; COMPUTER ANALYSIS OF SEQUENCE DATA, Part 1, (Griffin, A. M., and Griffin, H. G., eds.), 1994, Humana Press, New Jersey; von Heinje, G., SEQUENCE ANALYSIS IN MOLECULAR BIOLOGY, 1987, Academic Press; SEQUENCE ANALYSIS PRIMER, (Gribskov, M. and Devereux, J., eds.), 1991, M. Stockton Press, New York; Carillo et al., 1988, *SIAM J. Applied Math.*, 48:1073; and Durbin et al., 1998, BIOLOGICAL SEQUENCE ANALYSIS, Cambridge University Press.

Preferred methods to determine identity are designed to give the largest match between the sequences tested. Methods to determine identity are described in publicly available computer programs. Preferred computer program methods to determine identity between two sequences include, but are not limited to, the GCG program package, including GAP (Devereux et al., 1984, *Nucl. Acid. Res.*, 12:387; Genetics Computer Group, University of Wisconsin, Madison, Wis.), BLASTP, BLASTN, and FASTA (Altschul et al., 1990, *J. Mol. Biol.*, 215:403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990, supra). The well-known Smith Waterman algorithm may also be used to determine identity.

Certain alignment schemes for aligning two amino acid sequences may result in matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as three-times the average diagonal; where the "average diagonal" is the average of the diagonal of the comparison matrix being used; the "diagonal" is the score or number assigned to each perfect amino acid match by the particular comparison matrix) and a gap extension penalty (which is usually one-tenth of the gap opening penalty), as well as a comparison matrix such as PAM250 or BLOSUM 62 are used in conjunction with the algorithm. In certain embodiments, a standard comparison matrix (see Dayhoff et al., 1978, *Atlas of Protein Sequence and Structure*, 5:345-352 for the PAM 250 comparison matrix; Henikoff et al., 1992, *Proc. Natl. Acad. Sci. USA*, 89:10915-10919 for the BLOSUM 62 comparison matrix) is also used by the algorithm.

In certain embodiments, the parameters for a polypeptide sequence comparison include the following:

Algorithm: Needleman et al., 1970, *J. Mol. Biol.*, 48:443-453;

Comparison matrix: BLOSUM 62 from Henikoff et al., 1992, supra;

Gap Penalty: 12

Gap Length Penalty: 4

Threshold of Similarity: 0

The GAP program may be useful with the above parameters. In certain embodiments, the aforementioned parameters are the default parameters for polypeptide comparisons (along with no penalty for end gaps) using the GAP algorithm.

The term "homology" refers to the degree of similarity between protein or nucleic acid sequences. Homology information is useful for the understanding the genetic relatedness of certain protein or nucleic acid species. Homology can be determined by aligning and comparing sequences. Typically, to determine amino acid homology, a protein sequence is compared to a database of known protein sequences. Homologous sequences share common functional identities somewhere along their sequences. A high degree of similarity or identity is usually indicative of homology, although a low degree of similarity or identity does not necessarily indicate lack of homology.

Several approaches can be used to compare amino acids from one sequence to amino acids of another sequence to determine homology. Generally, the approaches fall into two categories: (1) comparison of physical characteristics such as polarity, charge, and Van der Waals volume, to generate a similarity matrix; and (2) comparison of likely substitution of an amino acid in a sequence by any other amino acid, which is based on observation of many protein sequences from known homologous proteins and to generate a Point Accepted Mutation Matrix (PAM).

The percentage of identity may also be calculated by using the program needle (EMBOSS package) or stretcher (EMBOSS package) or the program align X, as a module of the vector NTI suite 9.0.0 software package, using the default parameters (for example, GAP penalty 5, GAP opening penalty 15, GAP extension penalty 6.6).

As used herein, the twenty conventional amino acids and their abbreviations follow conventional usage. See IMMUNOLOGY—A SYNTHESIS, 2nd Edition, (E. S. Golub and D. R. Gren, Eds.), Sinauer Associates: Sunderland, Mass., 1991, incorporated herein by reference for any purpose. Stereoisomers (e.g., D-amino acids) of the twenty conventional amino acids; unnatural amino acids such as α-, α-disubstituted amino acids, N-alkyl amino acids, lactic acid, and other unconventional amino acids may also be suitable components for polypeptides of the invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:
1) hydrophobic: norleucine (Nor), Met, Ala, Val, Leu, Ile, Phe, Trp, Tyr, Pro;
2) polar hydrophilic: Arg, Asn, Asp, Gln, Glu, His, Lys, Ser, Thr;
3) aliphatic: Ala, Gly, Ile, Leu, Val, Pro;
4) aliphatic hydrophobic: Ala, Ile, Leu, Val, Pro;
5) neutral hydrophilic: Cys, Ser, Thr, Asn, Gln;
6) acidic: Asp, Glu;
7) basic: His, Lys, Arg;
8) residues that influence chain orientation: Gly, Pro;
9) aromatic: His, Trp, Tyr, Phe; and
10) aromatic hydrophobic: Phe, Trp, Tyr.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutamate (-3.5); glutamine (-3.5); aspartate (-3.5); asparagine (-3.5); lysine (-3.9); and arginine (-4.5).

The importance of the hydropathic amino acid index in conferring interactive biological function on a protein is understood in the art (see, for example, Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (-0.4); proline (-0.5±1); alanine (-0.5); histidine (-0.5); cysteine (-1.0); methionine (-1.3); valine (-1.5); leucine (-1.8); isoleucine (-1.8); tyrosine (-2.3); phenylalanine (-2.5) and tryptophan (-3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Op. in Biotech.* 7:422-427; Chou et al., 1974, *Biochemistry* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See Holm, 1999, supra; and Brenner, 1997, supra).

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

In additional embodiments, antibody variants can include antibodies comprising a modified Fc fragment or a modified heavy chain constant region. An Fc fragment, which stands for "fragment that crystallizes," or a heavy chain constant region can be modified by mutation to confer on an antibody altered binding characteristics. See, for example, Burton and Woof, 1992, *Advances in Immunology* 51: 1-84; Ravetch and Bolland, 2001, *Annu. Rev. Immunol.* 19: 275-90; Shields et al., 2001, *Journal of Biol. Chem.* 276: 6591-6604; Telleman and Junghans, 2000, *Immunology* 100: 245-251; Medesan et al., 1998, *Eur. J. Immunol.* 28: 2092-2100; all of which are incorporated herein by reference). Such mutations can include substitutions, additions, deletions, or any combination thereof, and are typically produced by site-directed mutagenesis using one or more mutagenic oligonucleotide(s) according to methods described herein, as well as according to methods known in the art (see, for example, Sambrook et al., MOLECULAR CLONING: A LABORATORY MANUAL, 3rd Ed., 2001, Cold Spring Harbor, N.Y. and Berger and Kimmel, METHODS IN ENZYMOLOGY, Volume 152, Guide to Molecular Cloning Techniques, 1987, Academic Press, Inc., San Diego, Calif., which are incorporated herein by reference).

According to certain embodiments, amino acid substitutions are those that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides. According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts). In preferred embodiments, a conservative amino acid substitution typically does not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in PROTEINS, STRUCTURES AND MOLECULAR PRINCIPLES, (Creighton, Ed.), 1984, W. H. Freeman and Company, New York; INTRODUCTION TO PROTEIN STRUCTURE (C. Branden and J. Tooze, eds.), 1991, Garland Publishing, New York, N.Y.; and Thornton et al., 1991, *Nature* 354:105, each of which are incorporated herein by reference.

Peptide analogs are commonly used in the pharmaceutical industry as non-peptide drugs with properties analogous to those of the template peptide. These types of non-peptide compound are termed "peptide mimetics" or "peptidomimetics". See Fauchere, 1986, *Adv. Drug Res.* 15:29; Veber & Freidinger, 1985, *TINS* p. 392; and Evans et al., 1987, *J. Med. Chem.* 30:1229, which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —$CH_2$—NH—, —$CH_2$—S—, —$CH_2$—$CH_2$—, —CH=CH-(cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo & Gierasch, 1992, *Ann. Rev. Biochem.* 61:387, incorporated herein by reference for any purpose); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding. In certain embodiments, binding fragments are produced by recombinant DNA techniques. In additional embodiments, binding fragments are produced by enzymatic or chemical cleavage of intact antibodies. Binding fragments include, but are not limited to, F(ab), F(ab'), F(ab')$_2$, Fv, and single-chain antibodies.

The term "heavy chain" includes any immunoglobulin polypeptide having sufficient variable region sequence to confer specificity for NGF. The term "light chain" includes any immunoglobulin polypeptide having sufficient variable region sequence to confer specificity for NGF. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxyl-terminus. The term "heavy chain", as used herein, encompasses a full-length heavy chain and fragments thereof. A full-length light chain includes a variable region domain, $V_L$, and a constant region domain, $C_L$. Like the heavy chain, the variable region domain of the light chain is at the amino-terminus of the polypeptide. The term "light chain", as used herein, encompasses a full-length light chain and fragments thereof. A F(ab) fragment is comprised of one light chain and the $C_H1$ and variable regions of one heavy chain. The heavy chain of a F(ab) molecule cannot form a disulfide bond with another heavy chain molecule. A F(ab') fragment contains one light chain and one heavy chain that contains more of the constant region, between the $C_H1$ and $C_H2$ domains, such that an interchain disulfide bond can be formed between two heavy chains to form a F(ab')$_2$ molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203.

A bivalent antibody other than a "multispecific" or "multifunctional" antibody, in certain embodiments, is understood to comprise binding sites having identical antigenic specificity.

In assessing antibody binding and specificity according to the invention, an antibody substantially inhibits adhesion of a ligand to a receptor when an excess of antibody reduces the quantity of ligand bound to receptor by at least about 20%, 40%, 60%, 80%, 85%, or more (as measured, inter alia, using an in vitro competitive binding assay).

By "neutralizing antibody" is meant an antibody molecule that is able to block or substantially reduce an effector function of a target antigen to which it binds. Accordingly, a "neutralizing" anti-NGF antibody is capable of blocking or substantially reducing an effector function, such as receptor binding and/or elicitation of a cellular response, of NGF. "Substantially reduce" is intended to mean at least about 60%, preferably at least about 70%, more preferably at least about 75%, even more preferably at least about 80%, still more preferably at least about 85%, most preferably at least about 90% reduction of an effector function of the target antigen (e.g., human NGF).

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. In preferred embodiments, an antibody is said to specifically bind an antigen when the equilibrium dissociation constant is $\leq 10^{-8}$ M, more preferably when the equilibrium dissociation constant is $\leq 10^{-9}$ M, and most preferably when the dissociation constant is $\leq 10^{-10}$ M.

An antibody binds "essentially the same epitope" as a reference antibody, when the two antibodies recognize identical or sterically overlapping epitopes. The most widely used and rapid methods for determining whether two antibodies bind to identical or sterically overlapping epitopes are competition assays, which can be configured in all number of different formats, using either labeled antigen or labeled antibody. Usually, the antigen is immobilized on a substrate, and the ability of unlabeled antibodies to block the binding of labeled antibodies is measured using radioactive or enzyme labels.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotin moieties that can be detected by labeled avidin (e.g., streptavidin preferably comprising a detectable marker such as a fluorescent marker, a chemiluminescent marker or an enzymatic activity that can be detected by optical or colorimetric methods). In certain embodiments, the label can also be therapeutic. Various methods of labeling polypeptides and glycoproteins are known in the art and may be used advantageously in the methods disclosed herein. Examples of labels for polypeptides include, but are not limited to, the following: radioisotopes or radionuclides (e.g., $^{3}H$, $^{14}C$, $^{15}N$, $^{35}S$, $^{90}Y$, $^{99m}Tc$, $^{111}In$, $^{125}I$, $^{131}I$), fluorescent labels (e.g., fluorescein isothiocyanate or FITC, rhodamine, or lanthanide phosphors), enzymatic labels (e.g., horseradish peroxidase, β-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, or epitope tags). In certain embodiments, labels are attached by spacer arms (such as $(CH_2)_n$, where n<about 20) of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent or drug" as used herein refers to a chemical compound or composition capable of inducing a desired therapeutic effect when properly administered to a patient. The expression "pharmaceutically effective amount" in reference to a pharmaceutical composition comprising one or a plurality of the antibodies of the invention is understood to mean, according to the invention, an amount of the said pharmaceutical composition which is capable of abolishing, in the patient considered, the decrease in the sensitivity threshold to external stimuli with a return of this sensitivity threshold to a level comparable to that observed in healthy subjects.

A "disorder" is any condition that would benefit from treatment according to the present invention. "Disorder" and "condition" are used interchangeably herein and include chronic and acute NGF-mediated disorders or NGF-mediated diseases, including those pathological conditions which predispose the mammal to the disorder in question.

The terms "NGF-mediated disease" and "NGF-mediated condition" encompass any medical condition or disorder associated with increased levels of NGF or increased sensitivity to NGF including, but not limited to, acute pain, dental pain, pain from trauma, surgical pain, pain resulting from amputation or abscess, causalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, irritable bowel syndrome, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, colitis, gastric ulceration, duodenal ulcers, vasomotor or allergic rhinitis, or bronchial disorders, dysmenorrhoea, dyspepsia, gastroesophageal reflux, pancreatitis, and visceralgia.

As used herein, the terms "effective amount" and "therapeutically effective amount" when used with reference to a vehicle- or a pharmaceutical composition comprising one or more anti-human NGF human antibody refers to an amount or dosage sufficient to produce a desired result (i.e., where for therapy with the vehicle- or anti-human NGF human antibodies of the present invention the desired result is the desired reduction in inflammation and/or pain, for example) or to support an observable decrease in the level of one or more biological activities of NGF. More specifically, a therapeutically effective amount is an amount of the anti-human NGF human antibody(ies) sufficient to inhibit, for some period of time, one or more of the clinically defined pathological processes associated with the condition at issue, e.g., inflammation or pain, in a subject treated in vivo with the agent. In the present invention, an "effective amount" of an anti-NGF antibody may prevent, stop, control, or reduce the perception of pain associated with any painful medical condition. In the methods of the present invention, the term "control" and grammatical variants thereof, are used to refer to the prevention, partial or complete inhibition, reduction, delay or slowing down of an unwanted event, e.g., pain. The effective amount may vary depending on the specific vehicle- or anti-human NGF human antibody(ies) selected, and is also dependent on a variety of factors and conditions related to the subject to be treated and the severity of the disorder. For example, if the vehicle- or anti-human NGF human antibody(ies) is to be administered in vivo, factors such as the age, weight and health of the patient as well as dose response curves and toxicity data obtained in preclinical animal work would be among those considered. If the agent is to be contacted with the cells in vitro, one would also design a variety of pre-clinical in vitro studies to assess such parameters as uptake, half-life, dose, toxicity, etc. The determination of an effective amount or a therapeutically effective amount for a given agent is well within the ability of those skilled in the art.

As used herein, the terms "nerve growth factor" and "NGF" are defined as all mammalian species of native sequence NGF, including recombinant human NGF 1-120, shown as in SEQ ID NO:30.

As used herein, "substantially pure" or "substantially purified" means a compound or species that is the predominant species present (i.e., on a molar basis it is more abundant than any other individual species in the composition). In certain embodiments, a substantially purified fraction is a composition wherein the species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the species is purified to essential homogeneity (contaminant species cannot be detected in the composition by conventional detection methods) wherein the composition consists essentially of a single macromolecular species.

The term "patient" includes human and animal subjects.

"Treatment" or "treat" refers to both therapeutic treatment and prophylactic or preventative measures. Those in need of treatment include those already with the disorder as well as those prone to have the disorder or those in which the disorder is to be prevented.

Unless otherwise required by context, singular terms shall include pluralities and plural terms shall include the singular.

According to certain embodiments of the invention, antibodies directed to NGF may be used to treat neuropathic and inflammatory pain and NGF-mediated diseases, including but not limited to, those mentioned above.

In one aspect of the invention are provided fully human monoclonal antibodies raised against and having biological and immunological specificity for binding to human NGF. In another aspect the invention provides nucleic acids comprising nucleotide sequences encoding amino acid sequences for heavy and light chain immunoglobulin molecules, particularly sequences corresponding to the variable regions thereof. Particular embodiments of this aspect of the invention are sequences corresponding to complementarity determining regions (CDRs), specifically from CDR1 through CDR3, of the heavy and light chains provided by the invention. In yet another aspect the invention provides hybridoma cells and cell lines that express the immunoglobulin molecules and antibodies, preferably monoclonal antibodies of the invention. The invention also provides biologically and immunologically purified preparations of antibodies, preferably monoclonal antibodies raised against and having biological and immunological specificity for binding to human NGF.

The ability to clone and reconstruct megabase-sized human loci in yeast artificial chromosomes (YACs) and to introduce them into the mouse germline provides an advantageous approach to elucidating the functional components of very large or crudely mapped loci as well as generating useful models of human disease. Furthermore, the utilization of such technology for substitution of mouse loci with their human equivalents provides unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study mechanisms underlying programmed expression and assembly of antibodies as well as their role in B-cell development. Furthermore, such a strategy provides a source for production of fully human monoclonal antibodies (MAbs).

The term "human antibody" includes antibodies having variable and constant regions substantially corresponding to human germline immunoglobulin sequences. In certain embodiments, human antibodies are produced in non-human mammals, including, but not limited to, rodents, such as mice and rats, and lagomorphs, such as rabbits. In certain embodiments, human antibodies are produced in hybridoma cells. In certain embodiments, human antibodies are produced recombinantly.

The term "recombinant" in reference to an antibody includes antibodies that are prepared, expressed, created or isolated by recombinant means. Representative examples include antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D., et al., *Nucl. Acids Res.* 20:6287-6295, (1992); or antibodies prepared, expressed, created or isolated by any means that involves splicing of human immunoglobulin gene sequences to other DNA sequences. Such recombinant human antibodies have variable and constant regions derived from human germline immunoglobulin sequences.

Human antibodies have at least three advantages over non-human and chimeric antibodies for use in human therapy:

1) because the effector portion of the antibody is human, it may interact better with the other parts of the human immune system (e.g., destroy the target cells more efficiently by complement-dependent cytotoxicity (CDC) or antibody-dependent cellular cytotoxicity (ADCC));

2) the human immune system should not recognize the human antibody as foreign, and, therefore the antibody response against such an injected antibody should be less than against a totally foreign non-human antibody or a partially foreign chimeric antibody;

3) injected non-human antibodies have been reported to have a half-life in the human circulation much shorter than the half-life of human antibodies. Injected human antibodies will have a half-life essentially identical to naturally occurring human antibodies, allowing smaller and less frequent doses to be given.

Thus, fully human antibodies are expected to minimize the immunogenic and allergic responses intrinsic to mouse or mouse-derivatized MAbs, and to thereby increase the efficacy and safety of the administered antibodies. Fully human antibodies of the invention, therefore, can be used in the treatment of chronic and recurring pain, the treatment thereof requiring repeated antibody administration. Thus, one particular advantage of the anti-NGF antibodies of the invention is that the antibodies are fully human and can be administered to patients in a non-acute manner while minimizing adverse reactions commonly associated with human anti-mouse antibodies or other previously described non-fully human antibodies from non-human species.

One skilled in the art can engineer mouse strains deficient in mouse antibody production with large fragments of the human Ig loci so that such mice produce human antibodies in the absence of mouse antibodies. Large human Ig fragments may preserve the large variable gene diversity as well as the proper regulation of antibody production and expression. By exploiting the mouse cellular machinery for antibody diversification and selection and the lack of immunological tolerance to human proteins, the reproduced human antibody repertoire in these mouse strains yields high affinity antibodies against any antigen of interest, including human antigens. Using the hybridoma technology, antigen-specific human MAbs with the desired specificity may be produced and selected.

Transgenic animals (e.g., mice) that are capable, upon immunization, of producing a full repertoire of human antibodies in the absence of endogenous immunoglobulin production can be employed. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-2555, (1993); Jakobovits et al., Nature, 362:255-258, (1993; Bruggemann et al., Year in Immun., 7:33 (1993); Nature 148:1547-1553 (1994), Nature Biotechnology 14:826 (1996); Gross, J. A., et al., Nature, 404:995-999 (2000); and U.S. Pat. Nos. 5,877,397, 5,874,299, 5,814,318, 5,789,650, 5,770,429, 5,661,016, 5,633,425, 5,625,126, 5,569,825, and 5,545,806 (each of which is incorporated herein by reference in its entirety for all purposes)). Human antibodies can also be produced in phage display libraries (Hoogenboom and Winter, J. Mol. Biol., 227:381 (1992); Marks et al., J. Mol. Biol., 222:581 (1991)). The techniques of Cole et al. and Boerner et al. are also available for the preparation of human monoclonal antibodies (Cole et al., Monoclonal Antibodies and Cancer Therap, Alan R. Liss, p. 77 (1985) and Boerner et al., J. Immunol., 147(1):86-95 (1991)).

Recombinant human antibodies may also be subjected to in vitro mutagenesis (or, when an animal transgenic for human Ig sequences is used, in vivo somatic mutagenesis) and, thus, the amino acid sequences of the VH and VL regions of the recombinant antibodies are sequences that, while derived from those related to human germline VH and VL sequences, may not naturally exist within the human antibody germline repertoire in vivo.

In certain embodiments, the skilled artisan can use constant regions from species other than human along with the human variable region(s) in such mice to produce chimeric antibodies.

Naturally Occurring Antibody Structure

Naturally occurring antibody structural units typically comprise a tetramer. Each such tetramer typically is composed of two identical pairs of polypeptide chains, each pair having one full-length "light" chain (typically having a molecular weight of about 25 kDa) and one full-length "heavy" chain (typically having a molecular weight of about 50-70 kDa). The amino-terminal portion of each light and heavy chain typically includes a variable region of about 100 to 110 or more amino acids that typically is responsible for antigen recognition. The carboxy-terminal portion of each chain typically defines a constant region responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM I and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., FUNDAMENTAL IMMUNOLOGY, Ch. 7, $2^{nd}$ ed., (Paul, W., ed.), 1989, Raven Press, N.Y. (incorporated by reference in its entirety for all purposes). The variable regions of each light/heavy chain pair typically form the antigen-binding site.

The variable regions typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (1987 and 1991, National Institutes of Health, Bethesda, Md.), or Chothia & Lesk, 1987, *J. Mol. Biol.* 196:901-917; Chothia et al., 1989, Nature 342:878-883.

Bispecific or Bifunctional Antibodies

A bispecific or bifunctional antibody typically is an artificial hybrid antibody having two different heavy chain/light chain pairs and two different binding sites. Bispecific antibodies may be produced by a variety of methods including, but not limited to, fusion of hybridomas or linking of F(ab') fragments. See, e.g., Songsivilai & Lachmann, 1990, *Clin. Exp. Immunol.* 79: 315-321; Kostelny et al., 1992, *J. Immunol.* 148:1547-1553.

Preparation of Antibodies

The invention provides antibodies that bind to human NGF. These antibodies can be produced by immunization with full-length NGF or fragments thereof. The antibodies of the invention can be polyclonal or monoclonal, and/or may be recombinant antibodies. In preferred embodiments, antibodies of the invention are human antibodies prepared, for example, by immunization of transgenic animals capable of producing human antibodies (see, for example, International Patent Application, Publication WO 93/12227).

The complementarity determining regions (CDRs) of the light chain and heavy chain variable regions of anti-NGF antibodies of the invention can be grafted to framework regions (FRs) from the same, or another, species. In certain embodiments, the CDRs of the light chain and heavy chain variable regions of anti-NGF antibody may be grafted to consensus human FRs. To create consensus human FRs, FRs from several human heavy chain or light chain amino acid sequences are aligned to identify a consensus amino acid sequence. The FRs of the anti-NGF antibody heavy chain or light chain can be replaced with the FRs from a different heavy chain or light chain. Rare amino acids in the FRs of the heavy and light chains of anti-NGF antibody typically are not replaced, while the rest of the FR amino acids can be replaced. Rare amino acids are specific amino acids that are in positions in which they are not usually found in FRs. The grafted variable regions from anti-NGF antibodies of the invention can be used with a constant region that is different from the constant region of anti-NGF antibody. Alternatively, the grafted variable regions are part of a single chain Fv antibody. CDR grafting is described, e.g., in U.S. Pat. Nos. 6,180,370, 5,693,762, 5,693,761, 5,585,089, and 5,530,101, which are hereby incorporated by reference for any purpose.

Antibodies of the invention are preferably prepared using transgenic mice that have a substantial portion of the human antibody producing locus inserted in antibody-producing cells of the mice, and that are further engineered to be deficient in producing endogenous, murine, antibodies. Such mice are capable of producing human immunoglobulin molecules and antibodies and do not produce or produce substantially reduced amounts of murine immunoglobulin molecules and antibodies. Technologies utilized for achieving this result are disclosed in the patents, applications, and references disclosed in the specification herein. In preferred embodiments, the skilled worker may employ methods as disclosed in International Patent Application Publication No. WO 98/24893, which is hereby incorporated by reference for any purpose. See also Mendez et al., 1997, *Nature Genetics* 15:146-156, which is hereby incorporated by reference for any purpose.

The monoclonal antibodies (mAbs) of the invention can be produced by a variety of techniques, including conventional monoclonal antibody methodology, e.g., the standard somatic cell hybridization technique of Kohler and Milstein (1975, *Nature* 256:495). Although somatic cell hybridization procedures are preferred, in principle, other techniques for producing monoclonal antibodies can be employed, e.g., viral or oncogenic transformation of B-lymphocytes.

The preferred animal system for preparing hybridomas is the mouse. Hybridoma production in the mouse is very well established, and immunization protocols and techniques for isolation of immunized splenocytes for fusion are well known in the art. Fusion partners (e.g., murine myeloma cells) and fusion procedures are also known.

In a preferred embodiment, human monoclonal antibodies directed against NGF can be generated using transgenic mice carrying parts of the human immune system rather than the mouse system. These transgenic mice, referred to herein as "HuMab" mice, contain a human immunoglobulin gene minilocus that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg et al., 1994, *Nature* 368:856-859). Accordingly, the mice exhibit reduced expression of mouse IgM or $\kappa$ and in response to immunization, the introduced human heavy chain and light chain transgenes undergo class switching and somatic mutation to generate high affinity human IgG κ monoclonal antibodies (Lonberg et al, supra.; Lonberg and Huszar, 1995, *Intern. Rev. Immunol.* 13:65-93; Harding and Lonberg, 1995, *Ann. N.Y. Acad. Sci.* 764:536-546). The preparation of HuMab mice is described in detail in Taylor et al., 1992, *Nucleic Acids Res.* 20:6287-6295; Chen et al., 1993, *International Immunology* 5:647-656; Tuaillon et al., 1994, *J. Immunol.* 152:2912-2920; Lonberg et al., 1994, *Nature* 368:856-859; Lonberg, 1994, *Handbook of Exp. Pharmacology* 113:49-101; Taylor et al., 1994, *International Immunology* 6:579-591; Lonberg & Huszar, 1995, *Intern. Rev. Immunol.* 13:65-93; Harding & Lonberg, 1995, *Ann. N.Y. Acad. Sci.* 764:536-546; Fishwild et al., 1996, *Nature Biotechnology* 14:845-851, the contents of all of which are hereby incorporated by reference in their entirety. See further U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, as well as U.S. Pat. No. 5,545,807 to Surani et al.; International Patent Application Publication Nos. WO 93/1227, published Jun. 24, 1993; WO 92/22646, published Dec. 23, 1992; and WO 92/03918, published Mar. 19, 1992, the disclosures of all of which are hereby incorporated by reference in their entirety. Alternatively, the HCo7, HCo12, and KM transgenic mice strains described in the Examples below can be used to generate human anti-NGF antibodies.

The present invention provides human monoclonal antibodies that are specific for and neutralize bioactive human NGF polypeptides. Also provided are antibody heavy and light chain amino acid sequences which are highly specific for and neutralize NGF polypeptides when they are bound to them. This high specificity enables the anti-human NGF human antibodies, and human monoclonal antibodies with like specificity, to be effective immunotherapy for NGF associated diseases.

In one aspect, the invention provides isolated human antibodies that bind the same or essentially the same epitope as the 4D4 antibody provided herein.

In one aspect, the invention provides isolated human antibodies comprising at least one of the amino acid sequences shown in SEQ ID NOS: 10, 12, 14, 16, 18, 20, 22, 24, and 79-130 that binds a NGF polypeptide epitope with high affinity and has the capacity to antagonize NGF polypeptide activity. Preferably, these antibodies binds the same or essentially the same epitope as the 4D4 antibody provided herein.

In preferred embodiments, the isolated human antibodies bind to NGF polypeptide with a dissociation constant ($K_D$) of $1 \times 10^{-9}$ M or less and inhibits NGF induced survival in an in vitro neutralization assay with an $IC_{50}$ of $1 \times 10^{-7}$ M or less. In more preferred embodiments, the isolated human antibodies bind to NGF polypeptide with a dissociation constant ($K_D$) of $1 \times 10^{-10}$ M or less and inhibits NGF induced survival in an in vitro neutralization assay with an $IC_{50}$ of $1 \times 10^{-8}$ M or less. In an even more preferred embodiment, the isolated anti-NGF human antibodies bind to human NGF polypeptide with a dissociation constant ($K_D$) of $1 \times 10^{-11}$ M or less and inhibits NGF induced survival in an in vitro assay with an $IC_{50}$ of $1 \times 10^{-9}$ M or less. Examples of anti-human NGF human antibodies that meet the aforementioned binding and neutralization criteria are provided herein.

The most preferred anti-human NGF human antibody of the present invention is referred to herein as 4D4 and has VL and VH polypeptide sequences as shown in SEQ ID NO: 12 and SEQ ID NO: 10, respectively. The polynucleotide sequence encoding the VL and VH of 4D4 is shown in SEQ ID NO: 11 and SEQ ID NO: 9, respectively. The properties of the anti-human NGF human antibodies of the present invention are specifically disclosed in the Examples. Particularly notable is the high affinity for NGF polypeptide and high capacity to antagonize NGF polypeptide activity demonstrated herein.

The dissociation constant ($K_D$) of an anti-human NGF human antibody can be determined by surface plasmon resonance as generally described in Example 9. Generally, surface plasmon resonance analysis measures real-time binding interactions between ligand (recombinant NGF polypeptide immobilized on a biosensor matrix) and analyte (antibodies in solution) by surface plasmon resonance (SPR) using the BIAcore system (Pharmacia Biosensor, Piscataway, N.J.). Surface plasmon analysis can also be performed by immobilizing the analyte (antibodies on a biosensor matrix) and presenting the ligand (recombinant V in solution). The dissociation constant ($K_D$) of an anti-human NGF human antibody can also be determined by using KinExA methodology. In certain embodiments of the invention, the antibodies bind to NGF with a $K_D$ of between approximately $10^{-8}$ M and $10^{-12}$ M. The term "$K_D$", as used herein, is intended to refer to the dissociation constant of a particular antibody-antigen interaction. For purposes of the present invention $K_D$ was determined as shown in Example 9.

In preferred embodiments, the antibodies of the invention are of the IgG1, IgG2, IgG3, or IgG4 isotype. Preferably, the antibodies are of the IgG3 isotype. More preferably, the antibodies are of the IgG1 isotype. Most preferably, the antibodies are of the IgG2 isotype. In other embodiments, the antibodies of the invention are of the IgM, IgA, IgE, or IgD isotype. In preferred embodiments of the invention, the antibodies comprise a human kappa light chain and a human IgG1, IgG2, IgG3, or IgG4 heavy chain. Expression of antibodies of the invention comprising an IgG1 or an IgG2 heavy chain constant region is described in the Examples below. In particular embodiments, the variable regions of the antibodies are ligated to a constant region other than the constant region for the IgG1, IgG2, IgG3, or IgG4 isotype. In certain embodiments, the antibodies of the invention have been cloned for expression in mammalian cells.

In certain embodiments, conservative modifications to the heavy chains and light chains of anti-NGF antibodies (and corresponding modifications to the encoding nucleotides) will produce anti-NGF antibodies having functional and chemical characteristics similar to those of the anti-NGF antibodies disclosed herein. In contrast, substantial modifications in the functional and/or chemical characteristics of anti-NGF antibodies may be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of anti-NGF antibody, or to increase or decrease the affinity of the anti-NGF antibodies described herein.

As it is well known, minor changes in an amino acid sequence such as deletion, addition or substitution of one, a few or even several amino acids may lead to an allelic form of the original protein which has substantially identical properties. Therefore, in addition to the antibodies specifically described herein, other "substantially homologous" antibodies can be readily designed and manufactured utilizing various recombinant DNA techniques well known to those skilled in the art. In general, modifications of the genes may be readily accomplished by a variety of well-known techniques, such as site-directed mutagenesis. Therefore, the present invention contemplates "variant" or "mutant" anti-NGF human antibodies having substantially similar characteristics to the anti-NGF human antibodies disclosed herein (See, for example, WO 00/56772, all of which is hereby incorporated herein by reference). Thus, by the term "variant" or "mutant" in reference to an anti-NGF human antibody is meant any binding molecule (molecule X) (i) in which the hypervariable regions CDR1, CDR2, and CDR3 of the heavy chain or the hypervariable regions CDR1, CDR2, and CDR3 of the light chain taken as a whole are at least 80% homologous, preferably at least 90% homologous, more preferably at least 95% homologous to the hypervariable regions as shown in SEQ ID NOS: 14, 18, and 22 or SEQ ID NOS: 16, 20, and 24, respectively, and (ii) wherein the variant or mutant is capable of inhibiting the activity of human NGF to the same extent as a reference anti-NGF human antibody having framework regions identical to those of molecule X.

Ordinarily, an anti-NGF human antibody variant will have light and/or heavy chain CDRs, when taken as a whole, that are at least about 80% amino acid sequence identity, preferably at least about 85% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity, yet more preferably at least about 99% amino acid sequence identity to the amino acid sequence as shown in SEQ ID NOS: 14, 18, and 22 and/or SEQ ID NOS: 16, 20, and 24, respectively.

More preferably, an anti-NGF human antibody variant will have a light chain variable region, when taken as a whole, that has at least about 80% amino acid sequence identity, yet more preferably at least about 81% sequence identity yet, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity, yet more preferably at least about 99% amino acid sequence identity to the amino acid sequence as shown in SEQ ID NOS: 12, 80, 82, 84, 86, 88, 89, 90, or 91 and/or a heavy chain variable region, when taken as a whole, that has at least about 70% amino acid sequence identity, preferably at least about 75% sequence identity, yet more preferably at least about 80% sequence identity, yet more preferably at least about 81% sequence identity yet, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity, yet more preferably at least about 99% amino acid sequence identity to the amino acid sequence as shown in SEQ ID NOS: 10, 81, 83, 85, or 87.

A "variant" in reference to a polynucleotide is intended to refer to an nucleic acid molecule having at least about 75% nucleic acid sequence identity with a polynucleotide sequence of the present invention. Ordinarily, a polynucleotide variant will have at least about 75% nucleic acid sequence identity, more preferably at least about 80% nucleic acid sequence identity, yet more preferably at least about 81% nucleic acid sequence identity, yet more preferably at least about 82% nucleic acid sequence identity, yet more preferably at least about 83% nucleic acid sequence identity, yet more preferably at least about 84% nucleic acid sequence identity, yet more preferably at least about 85% nucleic acid sequence identity, yet more preferably at least about 86% nucleic acid sequence identity, yet more preferably at least about 87% nucleic acid sequence identity, yet more preferably at least about 88% nucleic acid sequence identity, yet more preferably at least about 89% nucleic acid sequence identity, yet more preferably at least about 90% nucleic acid sequence identity, yet more preferably at least about 91% nucleic acid sequence identity, yet more preferably at least about 92% nucleic acid sequence identity, yet more preferably at least about 93% nucleic acid sequence identity, yet more preferably at least about 94% nucleic acid sequence identity, yet more preferably at least about 95% nucleic acid sequence identity, yet more preferably at least about 96% nucleic acid sequence identity, yet more preferably at least about 97% nucleic acid sequence identity, yet more preferably at least about 98% nucleic acid sequence identity, yet more preferably at least about 99% nucleic acid sequence identity with a novel nucleic acid sequence disclosed herein.

In particular embodiments, the invention provides antibodies that have a percentage of identity to an antibody of the invention, or an antibody that comprises a heavy chain variable region, a light chain variable region, a CDR1, CDR2, or CDR3 region that has a percentage of identity to a heavy chain variable region, a light chain variable region, a CDR1, CDR2, or CDR3 region of the invention, as shown in Example 10 herein and FIGS. 5-10.

In certain embodiments, the invention provides an isolated human antibody that specifically binds nerve growth factor and comprises a heavy chain and a light chain, wherein the heavy chain comprises a heavy chain variable region comprising an amino acid sequence that is: at least 70% or 75% identical to the amino acid sequence as set forth in SEQ ID NO: 10, or an antigen-binding or an immunologically functional immunoglobulin fragment thereof, at least 70%, 80%, 85%, or 95% homologous to the amino acid sequence as set forth in SEQ ID NO: 81, or an antigen-binding or an immunologically functional immunoglobulin fragment thereof, at least 70%, 80%, 85%, or 95% identical to the amino acid sequence as set forth in SEQ ID NO: 83, or an antigen-binding or an immunologically functional immunoglobulin fragment thereof, at least 75%, 80%, or 85% identical to the amino acid sequence as set forth in SEQ ID NO: 85, or an antigen-binding or an immunologically functional immunoglobulin fragment thereof, at least, 70%, 75%, or 80% identical to the amino acid sequence as set forth in SEQ ID NO: 87, or an antigen-binding or an immunologically functional immunoglobulin fragment thereof, at least 56% identical to the amino acid sequence as set forth in SEQ ID NO: 79, or an antigen-binding or an immunologically functional immunoglobulin fragment thereof.

In certain embodiments, the invention provides an isolated human antibody that specifically binds nerve growth factor and comprises a heavy chain and a light chain, wherein the light chain comprises a light chain variable region comprising an amino acid sequence that is: at least 70%, 75%, 80%, or 90% identical to the amino acid sequence as set forth in SEQ ID NO: 12 or an antigen-binding or an immunologically functional immunoglobulin fragment thereof, at least 70%, 85%, or 90% identical to the amino acid sequence as set forth in SEQ ID NO: 80, or an antigen-binding or an immunologically functional immunoglobulin fragment thereof, at least 70%, 74%, 90%, or 94% identical to the amino acid sequence as set forth in SEQ ID NO: 88, or an antigen-binding or an immunologically functional immunoglobulin fragment thereof, at least 70%, 80%, 85%, or 87% identical to the amino acid sequence as set forth in SEQ ID NO: 89, or an antigen-binding or an immunologically functional immunoglobulin fragment thereof, at least 70%, 85%, 90%, or 94% identical to the amino acid sequence as set forth in SEQ ID NO: 90, or an antigen-binding or an immunologically functional immunoglobulin fragment thereof, at least 70%, 85%, 90%, 95%, or 99% identical to the amino acid sequence as set forth in SEQ ID NO: 91, or an antigen-binding or an immunologically functional immunoglobulin fragment thereof, at least 70%, 80%, 90%, 95%, or 96% identical to the amino acid sequence as set forth in SEQ ID NO: 82, or an antigen-binding or an immunologically functional immunoglobulin fragment thereof, at least 70%, 85%, 90%, 95%, 98%, or 99% identical to the amino acid sequence as set forth in SEQ ID NO: 84, or an antigen-binding or an immunologically functional immunoglobulin fragment thereof; or at least 70%, 85%, 90%, 95%, 98%, or 99% identical to the amino acid sequence as set forth in SEQ ID NO: 86, or an antigen-binding or an immunologically functional immunoglobulin fragment thereof.

In certain other embodiments, the invention provides an isolated human antibody that specifically binds nerve growth factor and comprises a human heavy chain CDR1, wherein the heavy chain CDR1 is an amino acid sequence that is at least 40% or 60% identical to the amino acid sequence as set forth in SEQ ID NO: 98, SEQ ID NO: 105, SEQ ID NO: 110, or SEQ ID NO: 22, or an antigen-binding or an immunologically functional immunoglobulin fragment thereof.

In other embodiments, the invention provides an isolated human antibody that specifically binds nerve growth factor and comprises a human heavy chain CDR2, wherein the heavy chain CDR2 is an amino acid sequence that is: at least 70%, 82%, or 94% identical to the amino acid sequence as set forth in SEQ ID NO: 99, or an antigen-binding or an immunologically functional immunoglobulin fragment thereof, at least 70% or 76% identical to the amino acid sequence as set forth in SEQ ID NO: 106, or an antigen-binding or an immunologically functional immunoglobulin fragment thereof, at least 59% identical to the amino acid sequence as set forth in SEQ ID NO: 18, or an antigen-binding or an immunologically functional immunoglobulin fragment thereof, at least 70% identical to the amino acid sequence as set forth in SEQ ID NO: 117, or an antigen-binding or an immunologically functional immunoglobulin fragment thereof, or at least 70%, 75% or 80% identical to the amino acid sequence as set forth in SEQ ID NO: 111, or an antigen-binding or an immunologically functional immunoglobulin fragment thereof.

In yet other embodiments, the invention provides an isolated human antibody that specifically binds nerve growth factor and comprises a human light chain CDR1, wherein the CDR1 is an amino acid sequence that is: at least 70% or 80% identical to the amino acid sequence as set forth in SEQ ID NO: 101, or an antigen-binding or an immunologically functional immunoglobulin fragment thereof, at least 70%, 75%, 80% or 90% identical to the amino acid sequence as set forth in SEQ ID NO: 95, or an antigen-binding or an immunologically functional immunoglobulin fragment thereof, at least 75%, 80%, or 90% identical to the amino acid sequence as set forth in SEQ ID NO: 119, or an antigen-binding or an immunologically functional immunoglobulin fragment thereof, at least 75%, 80%, or 90% identical to the amino acid sequence as set forth in SEQ ID NO: 122, or an antigen-binding or an immunologically functional immunoglobulin fragment thereof, at least 80% identical to the amino acid sequence as set forth in SEQ ID NO: 125, or an antigen-binding or an immunologically functional immunoglobulin fragment thereof, at least 75%, 80%, or 90% identical to the amino acid sequence as set forth in SEQ ID NO: 24, or an antigen-binding or an immunologically functional immunoglobulin fragment thereof, at least 70% or 80% identical to the amino acid sequence as set forth in SEQ ID NO: 107, or an antigen-binding or an immunologically functional immunoglobulin fragment thereof, or at least 70% or 80% identical to the amino acid sequence as set forth in SEQ ID NO: 113, or an antigen-binding or an immunologically functional immunoglobulin fragment thereof.

In additional embodiments, the invention provides an isolated human antibody that specifically binds nerve growth factor and comprises a human light chain CDR2, wherein the CDR2 is an amino acid sequence that is: at least 70% or 85% identical to the amino acid sequence as set forth in SEQ ID NO: 102, or an antigen-binding or an immunologically functional immunoglobulin fragment thereof, at least 70% identical to the amino acid sequence as set forth in SEQ ID NO: 96, or an antigen-binding or an immunologically functional immunoglobulin fragment thereof, at least 70% identical to the amino acid sequence as set forth in SEQ ID NO: 120, or an antigen-binding or an immunologically functional immunoglobulin fragment thereof, at least 70% identical to the amino acid sequence as set forth in SEQ ID NO: 123, or an antigen-binding or an immunologically functional immunoglobulin fragment thereof, at least 70% or 85% identical to the amino acid sequence as set forth in SEQ ID NO: 126, or an antigen-binding or an immunologically functional immunoglobulin fragment thereof, at least 70% or 85% identical to the amino acid sequence as set forth in SEQ ID NO: 129, or an antigen-binding or an immunologically functional immunoglobulin fragment thereof, at least 70% identical to the amino acid sequence as set forth in SEQ ID NO: 20, or an antigen-binding or an immunologically functional immunoglobulin fragment thereof, at least 70% or 85% identical to the amino acid sequence as set forth in SEQ ID NO: 108, or an antigen-binding or an immunologically functional immunoglobulin fragment thereof, at least 70% identical to the amino acid sequence as set forth in SEQ ID NO: 133, or an antigen-binding or an immunologically functional immunoglobulin fragment thereof, or at least 70% or 85% identical to the amino acid sequence as set forth in SEQ ID NO: 114, or an antigen-binding or an immunologically functional immunoglobulin fragment thereof.

In other embodiments, the invention provides an isolated human antibody that specifically binds nerve growth factor and comprises a human light chain CDR3, wherein the CDR3 is an amino acid sequence that is: at least 70% or 85% identical to the amino acid sequence as set forth in SEQ ID NO: 103, or an antigen-binding or an immunologically functional immunoglobulin fragment thereof, at least 70% or 85% identical to the amino acid sequence as set forth in SEQ ID NO: 97, or an antigen-binding or an immunologically functional immunoglobulin fragment thereof, at least 70% or 78% identical to the amino acid sequence as set forth in SEQ ID NO: 121, or an antigen-binding or an immunologically functional immunoglobulin fragment thereof, at least 70% or 78% identical to the amino acid sequence as set forth in SEQ ID NO: 127, or an antigen-binding or an immunologically functional immunoglobulin fragment thereof, at least 70% or 78% identical to the amino acid sequence as set forth in SEQ ID NO: 130, or an antigen-binding or an immunologically functional immunoglobulin fragment thereof, at least 70% or 78% identical to the amino acid sequence as set forth in SEQ ID NO: 16, or an antigen-binding or an immunologically functional immunoglobulin fragment thereof, at least 70% or 85% identical to the amino acid sequence as set forth in SEQ ID NO: 109, or an antigen-binding or an immunologically functional immunoglobulin fragment thereof, at least 78% identical to the amino acid sequence as set forth in SEQ ID NO: 134, or an antigen-binding or an immunologically functional immunoglobulin fragment thereof, or at least 85% identical to the amino acid sequence as set forth in SEQ ID NO: 115, or an antigen-binding or an immunologically functional immunoglobulin fragment thereof.

The sequences of the 4D4 antibody heavy chain and light chain variable regions are shown in SEQ ID NOS: 10 and 12, respectively. However, many of the potential CDR-contact residues are amenable to substitution by other amino acids and still allow the antibody to retain substantial affinity for the antigen. Likewise, many of the framework residues not in contact with the CDRs in the heavy and light chains can accommodate substitutions of amino acids from the corresponding positions from other human antibodies, by human consensus amino acids, or from other mouse antibodies, without significant loss of the affinity or non-immunogenicity of the human antibody. Selection of various alternative amino acids may be used to produce versions of the disclosed anti-NGF antibodies and fragments thereof that have varying combinations of affinity, specificity, non-immunogenicity, ease of manufacture, and other desirable properties.

In alternative embodiments, antibodies of the invention can be expressed in cell lines other than hybridoma cell lines. In these embodiments, sequences encoding particular antibodies can be used for transformation of a suitable mammalian host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (all of which are hereby incorporated herein by reference for any purpose). Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

A nucleic acid molecule encoding the amino acid sequence of a heavy chain constant region, a heavy chain variable region, a light chain constant region, or a light chain variable region of an NGF antibody of the invention is inserted into an appropriate expression vector using standard ligation techniques. In a preferred embodiment, the anti-NGF antibody heavy chain or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see METH. ENZ. 185 (Goeddel, ed.), 1990, Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the anti-NGF antibody polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification or detection of the NGF antibody from the host cell. Affinity purification can be accomplished, for example, by column chromatography using antibodies against the tag as an affinity matrix. Optionally, the tag can subsequently be removed from the purified anti-NGF antibody polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Preferred selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody that binds to NGF polypeptide. As a result, increased quantities of a polypeptide such as an anti-NGF antibody are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the anti-NGF antibody. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding heavy chain or light chain comprising an anti-NGF antibody of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Bernoist and Chambon, 1981, *Nature* 290:304-10); CMV promoter (Thomsen et al., 1984, *Proc. Natl. Acad. USA* 81:659-663); the promoter contained in the 3' long terminal repeat of Rous sarcoma virus (Yamamoto, et al., 1980, *Cell* 22:787-97); herpes thymidine kinase promoter (Wagner et al., 1981, *Proc. Natl. Acad. Sci. U.S.A.* 78:1444-45); promoter and regulatory sequences from the metallothionine gene (Brinster et al., 1982, *Nature* 296: 39-42); and prokaryotic promoters such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region that is active in pancreatic beta cells (Hanahan, 1985, *Nature* 315:115-22); the immunoglobulin gene control region that is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region that is active in testicular, breast, lymphoid and mast cells (Leder et al., 1986, *Cell* 45:485-95); the albumin gene control region that is active in liver (Pinkert et al., 1987, *Genes and Devel.* 1:268-76); the alpha-feto-protein gene control region that is active in liver (Krumlauf et al., 1985, *Mol. Cell. Biol.*, 5:1639-48; Hammer et al., 1987, *Science* 235:53-58); the alpha 1-antitrypsin gene control region that is active in liver (Kelsey et al., 1987, *Genes and Devel.* 1:161-71); the beta-globin gene control region that is active in myeloid cells (Mogram et al., 1985, *Nature* 315:338-40; Kollias et al., 1986, *Cell* 46:89-94); the myelin basic protein gene control region that is active in oligodendrocyte cells in the brain (Readhead et al., 1987, *Cell* 48:703-12); the myosin light chain-2 gene control region that is active in skeletal muscle (Sani, 1985, *Nature* 314:283-86); and the gonadotropic releasing hormone gene control region that is active in the hypothalamus (Mason et al., 1986, *Science* 234:1372-78).

An enhancer sequence may be inserted into the vector to increase transcription of DNA encoding light chain or heavy chain comprising an anti-NGF antibody of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an anti-NGF antibody has been inserted into the proper site of the vector, the completed vector may be inserted into a suitable host cell for amplification and/or polypeptide expression. The transformation of an expression vector for an anti-NGF antibody into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., supra.

A host cell, when cultured under appropriate conditions, synthesizes an anti-NGF antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antibodies with NGF binding properties. In another embodiment, a cell line from the B cell lineage that does not make its own antibody but has a capacity to make and secrete a heterologous antibody can be selected.

Antibodies of the invention are useful for detecting NGF in biological samples and identification of cells or tissues that produce NGF protein. Antibodies of the invention that specifically bind to NGF may be useful in treatment of NGF mediated diseases. Said antibodies can be used in binding assays to detect NGF and to inhibit NGF from forming a complex with NGF receptors. Said antibodies that bind to NGF and block interaction with other binding compounds may have therapeutic use in modulating NGF mediated diseases. In preferred embodiments, antibodies to NGF may block NGF binding to its receptor, which may result in disruption of the NGF induced signal transduction cascade.

The present invention also relates to the use of one or more of the antibodies of the present invention in the manufacture of a medicament for the treatment of a painful disorder or condition caused by increased expression of NGF or increased sensitivity to NGF in a patient such as any one of disorders or conditions disclosed herein.

In preferred embodiments, the invention provides pharmaceutical compositions comprising a therapeutically effective amount of one or a plurality of the antibodies of the invention together with a pharmaceutically acceptable diluent, carrier, solubilizer, emulsifier, preservative and/or adjuvant. Preferably, acceptable formulation materials are nontoxic to recipients at the dosages and concentrations employed. In preferred embodiments, pharmaceutical compositions comprising a therapeutically effective amount of anti-NGF antibodies are provided.

In certain embodiments, acceptable formulation materials preferably are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See REMINGTON'S PHARMACEUTICAL SCIENCES, 18$^{th}$ Edition, (A. R. Gennaro, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibodies of the invention.

In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions of the present invention comprise Tris buffer of about pH 7.0-8.5, or acetate buffer of about pH 4.0-5.5, and may further include sorbitol, sucrose, Tween-20 and/or a suitable substitute therefor. In certain embodiments of the invention, anti-NGF antibody compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the anti-NGF antibody product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired anti-NGF antibody in a pharmaceutically acceptable vehicle. A particularly suitable vehicle for parenteral injection is sterile distilled water in which the anti-NGF antibody is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody molecule.

Pharmaceutical compositions of the invention can be formulated for inhalation. In these embodiments, anti-NGF antibodies are advantageously formulated as a dry, inhalable powder. In preferred embodiments, anti-NGF antibody inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. Anti-NGF antibodies that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the anti-NGF antibody. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of anti-NGF antibodies in a mixture with nontoxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving anti-NGF antibodies in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al, 1983, *Biopolymers* 22:547-556), poly (2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(–)-3-hydroxybutyric acid (European Patent Application Publication No. EP 133,988). Sustained release compositions may also include liposomes that can be prepared by any of several methods known in the art. See e.g., Eppstein et al., 1985, *Proc. Natl. Acad. Sci. USA* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The effective amount of an anti-NGF antibody-containing pharmaceutical composition to be employed therapeutically will depend, for example, upon the therapeutic context and objectives. One skilled in the art will appreciate that the appropriate dosage levels for treatment will vary depending, in part, upon the molecule delivered, the indication for which the anti-NGF antibody is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In preferred embodiments, the dosage may range from 0.1 µg/kg up to about 30 mg/kg; more preferably from 1 µg/kg up to about 30 mg/kg; or even more preferably from 5 µg/kg up to about 30 mg/kg.

Dosing frequency will depend upon the pharmacokinetic parameters of the particular anti-NGF antibody in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In certain embodiments, the antibodies of the invention can be administered to patients throughout an extended time period. Chronic administration of an antibody of the invention minimizes the adverse immune or allergic response commonly associated with antibodies that are raised against a human antigen in a non-human animal, for example, a non-fully human antibody produced in a non-human species.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use anti-NGF antibody pharmaceutical compositions according to the invention ex vivo. In such instances, cells, tissues or organs that have been removed from the patient are exposed to anti-NGF antibody pharmaceutical compositions after which the cells, tissues and/or organs are subsequently implanted back into the patient.

In particular, anti-NGF antibodies can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

EXAMPLES

The following examples, including the experiments conducted and results achieved are provided for illustrative purposes only and are not to be construed as limiting the invention.

Example 1

Generation of Human NGF Protein from *E. coli* Cells

Cloning of rHu-NGF (1-120)

The nucleotide sequence encoding human NGF was amplified from cDNA using the oligonucleotide primers with sequences as shown in SEQ ID NO:27 and SEQ ID NO:28 and standard PCR technology. The 5' primer creates an NdeI restriction site and methionine initiation codon immediately preceding codon 1 (serine) of the mature sequence. The 3' primer creates a BamHI restriction site immediately following the termination codon. The resulting PCR product was gel purified, digested with restriction endonucleases NdeI and BamHI, and then ligated into the vector pCFM1656, also digested with NdeI and BamHI. Ligated DNA was transformed into competent host cells of *E. coli* strain 657. Clones were screened for the ability to produce the recombinant protein product and to possess a plasmid having the correct nucleotide sequence (i.e., SEQ ID NO:29). The amino acid sequence of the recombinant human NGF 1-120 is shown as SEQ ID NO:30:

The expression vector pCFM1656 (ATCC #69576) was derived from the expression vector system described in U.S. Pat. No. 4,710,473. The pCFM1656 plasmid can be derived from the described pCFM836 plasmid (U.S. Pat. No. 4,710,473) by: (a) destroying the two endogenous NdeI restriction sites by end filling with T4 polymerase enzyme followed by blunt end ligation; (b) replacing the DNA sequence between the unique AatII and ClaI restriction sites containing the synthetic $P_L$ promoter with a similar fragment obtained from pCFM636 (U.S. Pat. No. 4,710,473) containing the PL promoter and then (c) substituting the small DNA sequence between the unique ClaI and KpnI restriction sites with oligonucleotide resulting from annealling two probes have nucleotide sequences as shown in SEQ ID NO: 31 and SEQ ID NO:32.

The *E. coli* $K_{12}$ host strain (Amgen strain 657) is a derivative of *E. coli* W1485 (a K12 strain), obtained from the *E. coli* Genetic Stock Center, Yale University, New Haven, Conn. (CGSC strain 6159).

Expression of rHu-NGF(1-120)

*E. coli* cells containing the NGF expression construct (as described above) were fermented in rich medium in fed-batch mode. Cells were grown at 30° C. to an OD at 600 nm of 49, and then induced by temperature shift to 42° C. Cells were harvested by centrifugation at four hours post induction. Final OD was 75. Expression yield was determined to be approximately 0.15 g/L.

Refolding and Purification of rHu-NGF(1-120)

Cell paste was lysed in a Microfluidizer, centrifuged at 10,000×g for 30 minutes, the pellet was washed with 1% deoxycholic acid, centrifuged as above, and the resulting pellet was then washed with cold water and re-centrifuged. The resulting pellet (WIBs—washed inclusion bodies) was resuspended in denaturant, 8M guanidine HCl, 50 mM Tris pH 8.5, containing 10 mM DTT, and solubilized at room temperature for 1 hour, centrifuged at 10,000×g for 30 minutes, and the supernatant was carefully decanted and then diluted 25-fold into an aqueous buffer containing a redox couple at 4° C., for 5 days. The resulting refold was then titrated to pH 3.0, filtered through a 0.45 uM filter. The refold was purified using a Sp-Sepharose fast flow column using a standard NaCl gradient. The pool from the cation exchange column was subsequently concentrated and aliquots were frozen −80° C. The purity of the protein was assessed by SDS-polyacrylamide gel electrophoresis (SDS-PAGE) and analyzed by Coomassie blue stain. The purified protein was greater than 90% main band by this method.

Example 2

Production of Human Monoclonal Antibodies Against Nerve Growth Factor (NGF)

Transgenic HuMab and KM Mice

Fully human monoclonal antibodies to NGF were prepared using HCo7, HCo12, HCo7+HCo12, and KM strains of transgenic mice, each of which expresses human antibody genes. In each of these mouse strains, the endogenous mouse kappa light chain gene has been homozygously disrupted as described in Chen et al. (1993, *EMBO J.* 12:811-820), and the endogenous mouse heavy chain gene has been homozygously disrupted as described in Example 1 of International Patent Application Publication No. WO 01/09187 (incorporated by reference). Each of these mouse strains carries a human kappa light chain transgene, KCo5, as described in Fishwild et al. (1996, *Nature Biotechnology* 14:845-851). The HCo7 strain carries the HCo7 human heavy chain transgene as described in U.S. Pat. Nos. 5,545,806, 5,625,825, and 5,545,807 (incorporated by reference). The HCo12 strain carries the HCo12 human heavy chain transgene as described in Example 2 of International Patent Application Publication No. WO 01/09187 (incorporated by reference). The HCo7+HCo12 strain carries both the HCo7 and the HCo12 heavy chain transgenes and is hemizygous for each transgene. The KM mice comprises the SC20 heavy chain transgene as described in Tomizuka et al. (1997, *Nature Genet.* 16, 133-143 and 2000, *Proc. Natl. Acad. Sci,* 97, 722-727). This transgene is not integrated into a mouse chromosome, but is instead propagated as an independent chromosome fragment. The fragment includes approximately 15 MB of human chromosome 14. It contains the entire human heavy chain locus including all VH, D and JH gene segments and all heavy chain constant region isotypes. All of these strains are referred to herein as HuMab mice.

HuMab Immunizations:

To generate fully human monoclonal antibodies to NGF, HuMab mice were immunized with purified recombinant NGF derived from *E. coli* cells as antigen (Example 1). General immunization schemes for HuMab mice are described in Lonberg et al. (1994, *Nature* 368:856-859; Fishwild et al., supra., and International Patent Application Publication No. WO 98/24884, the teachings of each of which are incorporated by reference). Mice were 6-16 weeks of age upon the first infusion of antigen. A purified recombinant preparation (25-100 μg) of NGF antigen was used to immunize the HuMab mice intraperitoneally (IP) or subcutaneously (SC).

Immunizations of HuMab transgenic mice were achieved using antigen in complete Freund's adjuvant and two injections, followed by 2-4 weeks IP immunization (up to a total of 9 immunizations) with the antigen in incomplete Freund's adjuvant. Several dozen mice were immunized for each antigen. A total of 118 mice of the HCo7, HCo12, HCo7+HCo12, and KM strains were immunized with NGF antigen. The immune response was monitored by retroorbital bleeds.

To select HuMab mice producing antibodies that bound human NGF, sera from immunized mice was tested by ELISA as described by Fishwild et al supra. Briefly, microtiter plates were coated with purified recombinant NGF from *E. coli* (Example 1) at 1-2 μg/mL in PBS and 50 μL/well incubated at 4° C. overnight, then blocked with 200 μL/well of 5% chicken serum in PBS/Tween (0.05%). Dilutions of plasma from NGF-immunized mice were added to each well and incubated for 1-2 hours at ambient temperature. The plates were washed with PBS/Tween and then incubated with a goat-anti-human IgG Fc-specific polyclonal reagent conjugated to horseradish peroxidase (HRP) for 1 hour at room temperature. Plates were washed with PBS/Tween and incubated with a goat anti-human IgG Fc-specific polyclonal reagent conjugated to horseradish peroxidase (HRP) for 1 hour at room temperature. After washing, the plates were developed with ABTS substrate (Sigma Chemical Co., St. Louis, Mo., Catalog No. A-1888, 0.22 mg/mL) and analyzed spectrophotometrically by determining optical density (OD) at wavelengths from 415-495 nm. Mice with sufficient titers of anti-NGF human immunoglobulin were used to produce monoclonal antibodies as described below.

Generation of Hybridomas Producing Human Monoclonal Antibodies to NGF

Mice were prepared for monoclonal antibody production by boosting with antigen intravenously 2 days before sacrifice, and spleens were removed thereafter. The mouse splenocytes were isolated from the HuMab mice and fused with PEG to a mouse myeloma cell line using standard protocols. Typically, 10-20 fusions for each antigen were performed.

Briefly, single cell suspensions of splenic lymphocytes from immunized mice were fused to one-fourth the number of P3X63-Ag8.653 nonsecreting mouse myeloma cells (ATCC, Accession No. CRL 1580) with 50% PEG (Sigma). Cells were plated at approximately $1 \times 10^5$/well in flat bottom microtiter plates, followed by about a two week incubation in selective medium containing 10% fetal bovine serum, 10% P388D1-(ATCC, Accession No. CRL TIB-63) conditioned medium, 3-5% origen (IGEN) in DMEM (Mediatech, Catalog No. CRL 10013, with high glucose, L-glutamine and sodium pyruvate) plus 5 mM HEPES, 0.055 mM 2-mercaptoethanol, 50 mg/mL gentamycin and 1×HAT (Sigma, Catalog No. CRL P-7185). After 1-2 weeks, cells were cultured in medium in which the HAT was replaced with HT.

The resulting hybridomas were screened for the production of antigen-specific antibodies. Individual wells were screened by ELISA (described above) for human anti-NGF monoclonal IgG antibodies. Once extensive hybridoma growth occurred, medium was monitored usually after 10-14 days. Antibody secreting hybridomas were replated, screened again and, if still positive for human IgG, anti-NGF monoclonal antibodies were subcloned at least twice by limiting dilution. The stable subclones were then cultured in vitro to generate small amounts of antibody in tissue culture medium for characterization.

Selection of Human Monoclonal Antibodies that Bind to NGF

An ELISA assay as described above was used to screen for hybridomas that showed positive reactivity with NGF immunogen. Hybridomas secreting a monoclonal antibody that bound with high avidity to NGF were subcloned and further characterized. One clone from each hybridoma, which retained the reactivity of parent cells (as determined by ELISA), was chosen for making a 5-10 vial cell bank stored in liquid nitrogen.

An isotype-specific ELISA was performed to determine the isotype of the monoclonal antibodies produced as disclosed herein. In these experiments, microtiter plate wells were coated with 50 µL/well of a solution of 1 µg/mL of mouse anti-human kappa light chain in PBS and incubated at 4° C. overnight. After blocking with 5% chicken serum, the plates were reacted with supernatant from each tested monoclonal antibody and a purified isotype control. Plates were incubated at ambient temperature for 1-2 hours. The wells were then reacted with various human IgG-specific horseradish peroxidase-conjugated goat anti-human polyclonal antisera and plates were developed and analyzed as described above.

Monoclonal antibodies purified from the hybridoma supernatants that showed significant binding to NGF as detected by ELISA were further tested for biological activity using a variety of bioassays as described below.

Example 3

Selecting and Cloning Anti-NGF Antibodies with Potent NGF Neutralizing Activity

The effectiveness of the antibodies initially identified in Example 2 as inhibitors of NGF activity (i.e., NGF "neutralization") was evaluated by measuring the ability of each modified peptide to block NGF induction of vanilloid receptor-1 (VR1) expression.

Dorsal Root Ganglion Neuronal Cultures

Dorsal root ganglia (DRG) were dissected one by one under aseptic conditions from all spinal segments of embryonic 19-day old (E19) rats that were surgically removed from the uterus of timed-pregnant, terminally anesthetized Sprague-Dawley rats (Charles River, Wilmington, Mass.). DRG were collected in ice-cold L-15 media (GibcoBRL, Grand Island, N.Y.) containing 5% heat inactivated horse serum (GibcoBRL), and any loose connective tissue and blood vessels were removed. The DRG were rinsed twice in $Ca^{2+}$- and $Mg^{2+}$-free Dulbecco's phosphate buffered saline (DPBS), pH 7.4 (GibcoBRL). The DRG were then dissociated into single cell suspension using a papain dissociation system (Worthington Biochemical Corp., Freehold, N.J.). Briefly, DRG were incubated in a digestion solution containing 20 U/ml of papain in Earle's Balanced Salt Solution (EBSS) at 37° C. for fifty minutes. Cells were dissociated by trituration through fire-polished Pasteur pipettes in a dissociation medium consisting of MEM/Ham's F12, 1:1, 1 mg/ml ovomucoid inhibitor and 1 mg/ml ovalbumin, and 0.005% deoxyribonuclease I (DNase).

The dissociated cells were pelleted at 200×g for five minutes and re-suspended in EBSS containing 1 mg/ml ovomucoid inhibitor, 1 mg/ml ovalbumin and 0.005% DNase. Cell suspension was centrifuged through a gradient solution containing 10 mg/ml ovomucoid inhibitor, 10 mg/ml ovalbumin at 200×g for six minutes to remove cell debris, and then filtered through a 88-µm nylon mesh (Fisher Scientific, Pittsburgh, Pa.) to remove any clumps. Cell number was determined with a hemocytometer, and cells were seeded into poly-ornithine 100 µg/ml (Sigma, St. Louis, Mo.) and mouse laminin 1 µg/ml (GibcoBRL)-coated 96-well plates at $10 \times 10^3$ cells/well in complete medium. The complete medium consisted of minimal essential medium (MEM) and Ham's F12, 1:1, penicillin (100 U/ml), streptomycin (100 µg/ml), and 10% heat inactivated horse serum (GibcoBRL). The cultures were kept at 37° C., 5% $CO_2$ and 100% humidity. For controlling the growth of non-neuronal cells, 5-fluoro-2'-deoxyuridine (75 µM) and uridine (180 µM) were included in the medium.

Treatment with NGF and Anti-NGF

Two hours after plating, cells were treated with recombinant human β-NGF (Amgen) or recombinant rat β-NGF (R&D Systems, Minneapolis, Minn.) at a concentration of 10 ng/ml (0.38 nM). Positive controls comprising serial-diluted anti-NGF antibody (R&D Systems) were applied to each culture plate. Test antibodies were added at ten concentrations using 3.16-fold serial dilutions. All of the samples were diluted in complete medium before being added to the cultures. Incubation time was 40 hours prior to measurement of VR1 expression.

Measurement of VR1 Expression in DRG Neurons

Cultures were fixed with 4% paraformaldehyde in Hanks' balanced salt solution for fifteen minutes, blocked with Superblock (Pierce, Rockford, Ill.), and permeabilized with 0.25% Nonidet P-40 (Sigma) in Tris-HCl (Sigma)-buffered saline (TBS) for one hour at room temperature. Cultures were rinsed once with TBS containing 0.1% Tween 20 (Sigma) and incubated with rabbit anti-VR1 IgG for one and one-half hours at room temperature, followed by incubation of Eu-labeled anti-rabbit second antibody (Wallac Oy, Turku, Finland) for one hour at room temperature. Washes with TBS (3× five minutes with slow shaking) were applied after each antibody incubation. Enhance solution (150 µl/well, Wallac Oy)

was added to the cultures. The fluorescence signal was then measured in a time-resolved fluorometer (Wallac Oy). VR1 expression in samples treated with the modified peptides was determined by comparing to a standard curve of NGF titration from 0-1000 ng/ml. Percent inhibition (compared to maximum possible inhibition) of NGF effect on VR1 expression in DRG neurons was determined by comparing to controls that were not NGF-treated. Results are given in Tables 2 and 5.

The cell lines were labeled #110-#129. Antibodies from cell lines #119, #124, and #125 demonstrated extremely potent NGF neutralization activity (FIG. 1). The #124 cell line was a parental cell line, also referred to as 4D4. The #119 and #125 cell lines were subclones of the 4D4 parent. An additional sample from the original vial comprising hybridoma #124 (4D4) was grown and labeled #167 (4D4).

Antibodies generated by hybridoma #167 (4D4) were subjected to the same DRG neuron based NGF neutralization assay as the previous samples. Antibody #167 (4D4) demonstrated strong anti-NGF activity with an $IC_{50}$ of 0.50 nM (FIG. 2), which was consistent with the activity of samples #119, #124, and #125. The activities of the 4 samples are shown in Table 2.

TABLE 2

| Anti-hNGF activity in DRG cells using 0.38 nM hNGF | |
|---|---|
| Code # | IC50 |
| 119 (from 124) | <1.2 nM |
| 124 (parent) | <0.57 nM |
| 125 (from 124) | <0.3 nM |
| 167 (from same sample as 124)* | 0.50 nM |

N-Terminal Sequencing and Mass Spectrometry

Purified anti-NGF hybridoma antibodies samples were prepared for protein sequencing and LC/MS analysis. Antibodies were purified from conditioned media by concentrating the media using Amicon centriprep-30 until the volume was less than 15 ml. A batch of rProA (Pharmacia) resin was washed 4× with PBS and a 50% slurry made in PBS following the last wash. An appropriate amount of rProA resin (approximately 5 ug antibody/ul resin but use no less than 50 ul resin) was added to the antibody sample and incubated overnight at 4° C. The Ab-resin mixture was centrifuged and the unbound fraction was collected. After addition of 0.5 ml PBS and transfer to a 0.45 um Spin-X (CoStar) tube the sample was centrifuged at 10000 rpm for 3 min. The resin was next washed at least 3 times with 0.5 ml PBS and then of 0.1M glycine (pH 2.7) was added at 1.5× volume of resin and incubated for 10 minutes at room temperature followed by another centrifugation for 3 minutes at 10000 rpm, collecting the supernatant. This elution step was repeated two more times and then the combined supernatant was neutralized with $\frac{1}{25}^{th}$ volume of 1.0 M tris (pH 9.2).

After a final filtering step through a new Spin-x tube (0.2 um) the antibody was quantified using a standard Bradford assay using human IgG as the standard or alternately absorbance at 280 for larger samples. A gel was also run using with 2 ug of each sample alongside 2 ug of human IgG1,k (Sigma). For mass spectrometry, four micrograms of the samples were deglycosylated, reduced, and loaded onto an HPLC (HP1090) on-line linked to a Finingan LCQ mass spectrometer. The light chain was separated from the heavy chain by reversed phase HPLC. The light chains and heavy chains were also collected for N-terminal protein sequencing analysis.

Both N-terminal sequences of the light chain and heavy chain of the sample of anti-NGF #167 (4D4) antibody matched both N-terminal sequences of the sample of anti-NGF #119 (4D4) antibody. In addition, the measured mass of the antibodies indicated that the isolated antibodies from the #167 and #119 hybridomas were the same. The measured, deconvoluted mass (23096) of the light chain of anti-NGF #167 matched the measured mass (23096) of the light chain of anti NGF Ab #119.

Cloning the Anti-NGF Antibody Heavy and Light Chains

The hybridoma expressing the most potent NGF binding monoclonal antibody, 4D4.D7, was used as sources to isolate total RNA using TRIzol® reagent (Invitrogen). First strand cDNA was synthesized using a random primer with an extension adapter (5'-GGC CGG ATA GGC CTC CAN NNN NNT-3') (SEQ ID NO: 33) and a 5' RACE (rapid amplification of cDNA ends) preparative assay was performed using the GeneRacer™ Kit (Invitrogen) according to instructions from the manufacturer. For preparing complete light chain encoding cDNA, the forward primer was the GeneRacer™ nested primer, and the reverse primer was 5'-GGG GTC AGG CTG GAA CTG AGG-3' (SEQ ID NO: 34). For preparing cDNA encoding the variable region of the heavy chain, the forward primer was the GeneRacer™ nested primer and the reverse primer was 5'-TGA GGA CGC TGA CCA CAC G-3' (SEQ ID NO 35). RACE products were cloned into pCR4-TOPO (Invitrogen) and the sequences determined. Consensus sequences were used to design primers for full-length anti-body chain PCR amplification.

For preparing cDNA encoding anti-NGF 4D4.D7 kappa light chain, the 5' PCR primer encoded the amino terminus of the signal sequence, an XbaI restriction enzyme site, and an optimized Kozak sequence (5'-CAG CAG AAG CTT CTA GAC CAC CAT GGA CAT GAG GGT GCC CGC TCA GCT CCT GGG-3'; SEQ ID NO: 36). The 3' primer encoded the carboxyl terminus and termination codon, as well as a SalI restriction site (5'-CTT GTC GAC TCA ACA CTC TCC CCT GTT GAA GCT C-3'; SEQ ID NO: 37). The resulting PCR product fragment was purified, digested with XbaI and SalI, and then gel isolated and ligated into the mammalian expression vector pDSRα20 (see International Application, Publication No. WO 90/14363, which is herein incorporated by reference for any purpose. pDSRα20 was produced by changing nucleotide 2563 in pDSRa19 from a "Guanosine" to an "Adenosine" by site directed mutagenesis.).

For preparing cDNA encoding anti-NGF 4D4.D7 heavy chain the 5' PCR primer encoded the amino terminus of the signal sequence, an XbaI restriction enzyme site, and an optimized Kozak sequence (5'-CAG CAG AAG CTT CTA GAC CAC CAT GGA GTT GGG GCT GTG CTG GGT TTT CCT TGT T-3'; SEQ ID NO: 38). The 3' primer encoded the carboxyl terminus and termination codon, as well as a SalI restriction site (5'-GCA TGT CGA CTC ATT TAC CCG GAG ACA GGG AGA G-3'; SEQ ID NO: 39). The resulting product was purified, digested with XbaI and SalI, gel isolated and ligated into the pDSRa20 vector.

The calculated mass (23099), as determined by translating the nucleotide sequence to predicted amino acids and adding together the molecular weights of the amino acids, of the DNA sequence of the light chain of anti-NGF Ab 4D4 clone matched the measured mass as determined by mass spectrometry. The measured, deconvoluted mass (49479) of the heavy chain of anti-NGF Ab #167 matched the measured mass (49484) of the heavy chain of anti NGF Ab #119 and also matched the theoretical mass (49484) of the DNA sequence of the heavy chain of anti-NGF Ab 4D4 clone (Table 3) within instrumental deviation.

The data of N-terminal protein sequence and LC/MS confirmed that hybridoma #119 expressed the same antibody as hybridoma #167. In addition, the calculated mass of the antibodies based on sequence further confirmed the observation.

TABLE 3

Summary of Mass Spectrometry Findings

| anti NGF Ab | Measured mass of Ab #167 | Measured mass of Ab #119 | Theoretical mass derived from DNA sequence of Ab 4D4 |
|---|---|---|---|
| light chain | 23096 | 23096 | 23099 |
| heavy chain | 49479 | 49484 | 49484 |

Example 4

Expression of Anti-NGF Antibodies in Chinese Hamster Ovary (CHO) Cells

Stable expression of the 4D4 anti-NGF mAb was achieved by co-transfection of 4D4-heavy chain/pDSRα19 IgG2 or 4D4-heavy chain/pDSRα19 IgG1 and NGF-kappa/pDSRα19 plasmids into dihydrofolate reductase deficient (DHFR⁻) serum-free adapted Chinese hamster ovary (CHO) cells using a calcium phosphate method. Transfected cells were selected in medium containing dialyzed serum but not containing hypoxanthine-thymidine to ensure the growth of cells expressing the DHFR enzyme. Transfected clones were screened using assays such as ELISA in order to detect the expression of 4D4 anti-NGF mAb in the conditioned medium. The highest expressing clones were subjected to increasing concentrations of methotrexate (MTX) for DHFR amplification. MTX amplified clones were screened using assays such as ELISA in order to detect higher expression of 4D4 anti-NGF mAb in the conditioned medium. The highest expressing clones were subjected to subcloning to obtain a homogeneous population and creation of cell banks.

Recombinant anti-NGF antibodies of the invention can be generated in Chinese hamster ovary cells deficient in DHFR using the same protocol as described above for the anti-NGF monoclonal antibody. The DNA sequences encoding the complete heavy chain or light chain of each anti-NGF antibody of the invention are cloned into expression vectors. CHOd-cells are co-transfected with an expression vector capable of expressing a complete heavy chain and an expression vector expressing the complete light chain of the appropriate anti-NGF antibody. For example, to generate the anti-NGF antibody, cells are co-transfected with a vector capable of expressing a complete heavy chain comprising the amino acid sequence as set forth in SEQ ID NO: 40 and a vector capable of expressing a complete light chain comprising the amino acid sequence set forth in SEQ ID NO: 44. Table 4 summarizes complete heavy and complete light chains for the 4D4 antibodies having various IgG heavy chain constant regions.

TABLE 4

| Antibody | Heavy Chain Variable Region + Heavy Chain Constant Region | Complete Heavy Chain |
|---|---|---|
| 4D4(IgG2) | SEQ ID NO: 10 + SEQ ID NO: 4 | SEQ ID NO: 40 |
| 4D4(IgG1) | SEQ ID NO: 10 + SEQ ID NO: 2 | SEQ ID NO: 41 |
| 4D4(IgG4) | SEQ ID NO: 10 + SEQ ID NO: 6 | SEQ ID NO: 42 |
| 4D4(IgG3) | SEQ ID NO: 10 + SEQ ID NO: 26 | SEQ ID NO: 43 |

| Antibody | Light Chain Variable Region + Light Chain Constant Region | Complete Light Chain |
|---|---|---|
| 4D4 | SEQ ID NO: 12 + SEQ ID NO: 8 | SEQ ID NO: 44 |

Example 5

Characterizing the Activity of Anti-NGF 4D4 Antibodies

Transiently expressed anti-NGF 4D4 antibodies, generated in cells grown under spinner (S) or roller (R) conditions were tested to confirm their ability to neutralize NGF in a DRG neuron based NGF neutralization bioassay, performed as described above (Example 3).

The NGF antibodies were expressed transiently in serum-free suspension adapted 293T cells. Transfections were performed as either 500 mL or IL cultures. Briefly, the cell inoculum ($5.0 \times 10^5$ cells/mL×culture volume) was centrifuged at 2,500 RPM for 10 minutes at 4° C. to remove the conditioned medium. The cells were resuspended in serum-free DMEM and centrifuged again at 2,500 RPM for 10 minutes at 4° C. After aspirating the wash solution, the cells were resuspended in growth medium [DMEM/F12 (3:1)+1× Insulin-Transferrin-Selenium Supplement+1× Pen Strep Glut+2 mM L-Glutamine+20 mM HEPES+0.01% Pluronic F68] in a 1 L or 3 L spinner flask culture. The spinner flask culture was maintained on magnetic stir plate at 125 RPM which was placed in a humidified incubator maintained at 37° C. and 5% $CO_2$. The plasmid DNA was complexed to the transfection reagent in a 50 mL conical tube. The DNA-transfection reagent complex was prepared in 5% of the final culture volume in serum-free DMEM. 1 µg plasmid DNA/mL culture was first added to serum-free DMEM, followed by 1 µl X-TremeGene RO-1539/mL culture. The complexes were incubated at room temperature for approximately 30 minutes and then added to the cells in the spinner flask. The transfection/expression was performed for 7 days, after which the conditioned medium was harvested by centrifugation at 4,000 RPM for 60 minutes at 4° C.

For roller bottle transient transfections, we used 293T adherent cells grown and maintained in DMEM supplemented with 5% FBS+1× Non-Essential Amino Acids+1× Pen Strep Glut+1× Sodium Pyruvate. Approximately, 4-5× $10^7$ 293T cells were seeded in a 850 cm² roller bottles overnight. The previously seeded cells were then transfected the following day using FuGene6 transfection reagent. The DNA—transfection reagent mixture was prepared in approximately in 6.75 mL serum-free DMEM. 675 µl FuGene6 transfection reagent was first added, followed by 112.5 µg plasmid DNA. The complex was incubated at room temperature for 30 minutes. The entire mixture was then added to a roller bottle. The roller bottle was gassed with a 5% $CO_2$ gas mixture, capped tightly and placed in a 37° C. incubator on a roller rack rotating at 0.35 RPM. The transfection was performed for 24 hours after which the medium was replaced with 100 mL DMEM+1× Insulin-Transferrin-Selenium Supplement+1× Pen Strep Glu+1× Non-Essential Amino Acids+1× Sodium Pyruvate. Typically, two 100 ml 48 hour harvests were obtained from each roller bottle. The harvested serum-free conditioned medium was pooled together and centrifuged at 4,000 RPM for 30 minutes at 4° C.

Figure 3:
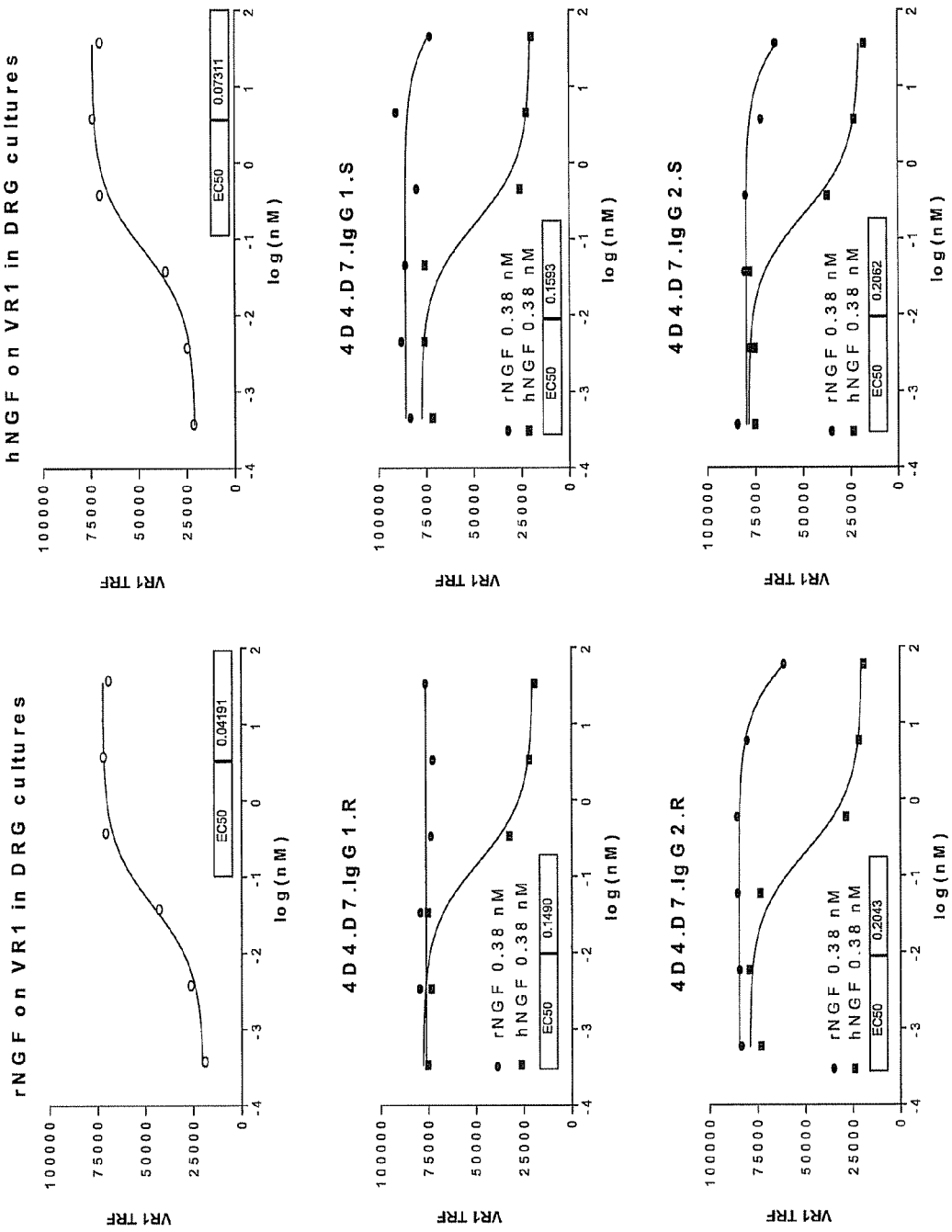
FIG. 3 depicts graphs that demonstrate neutralization of NGF activity in DRG neuron based neutralization bioassays by transiently expressed recombinant anti-NGF 4D4 monoclonal antibodies when expressed as either an IgG1 or IgG2 and in cells grown either in a roller bottle culture (R) or in spinner flasks (S).
Figure 4:
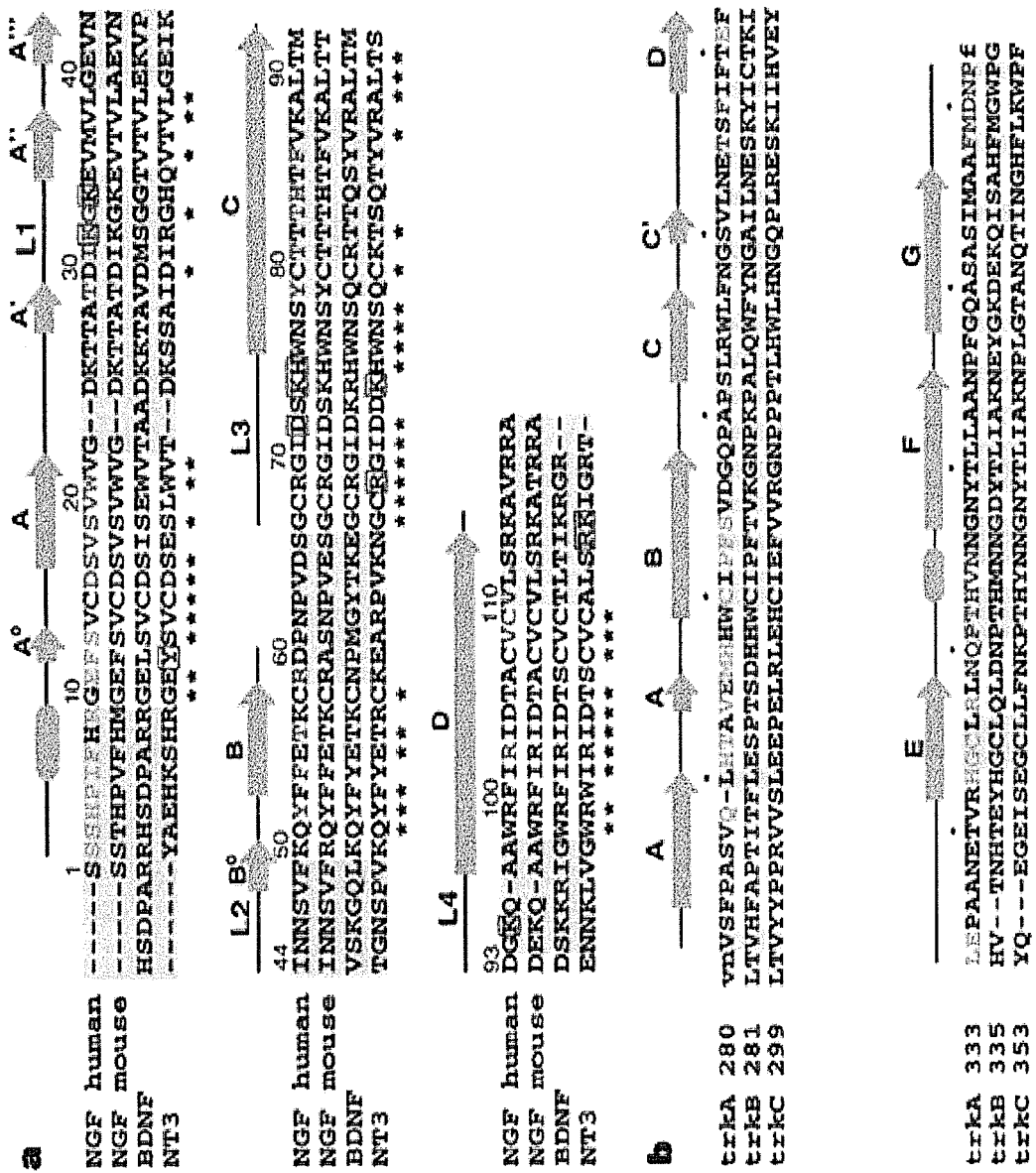
FIGS. 4(a) and 4(b) depict sequence alignments of neurotrophins. The numbering and secondary structure elements above the sequence refer to mature human NGF. Conserved residues are marked with a star, and regions with low sequence homology are shaded. NGF human is SEQ ID NO: 135; NGF mouse is SEQ ID NO: 136; BDNF is SEQ ID NO: 137; NT3 is SEQ ID NO: 138; trkA receptor is SEQ ID NO: 139; trkB receptor is SEQ ID NO: 140; trkC receptor is SEQ ID NO: 141.

Both 4D4.IgG1 and 4D4.IgG2 showed potent activity with $IC_{50}$ values of about 0.14 nM to about 0.2 nM against human NGF (FIG. 2). The results of the activity assay are summarized in Table 5. The antibodies showed little activity against rat NGF (FIG. 3). The results resemble the activity of the antibodies tested directly from hybridomas described above.

TABLE 5

| Ab | IC50 @ hNGF (nM) | IC50 @ rNGF (nM) |
|---|---|---|
| 4D4.IgG1.R | 0.1488 | >34 nM |
| 4D4.IgG1.S | 0.1587 | >45 nM |
| 4D4.IgG2.R | 0.2047 | >59 nM |
| 4D4.IgG2.S | 0.2063 | >37 nM | hNGF = human NGF,
rNGF = rat NGF,
R = Roller culture,
S = Spinner culture

Example 6

Production of Anti-NGF Antibody

Anti-NGF antibody is produced by expression in a clonal line of CHO cells. For each production run, cells from a single vial are thawed into serum-free cell culture media. The cells are grown initially in a T-flask followed by spinner flasks and then grown in stainless steel reactors of increasing scale up to a 2000 L bioreactor. Production is carried out in a 2000 L bioreactor using a fed batch culture, in which a nutrient feed containing concentrated media components is added to maintain cell growth and culture viability. Production lasts for approximately two weeks during which time anti-NGF antibody is constitutively produced by the cells and secreted into the cell culture medium.

The production reactor is controlled at a predetermined pH, temperature, and dissolved oxygen level: pH is controlled by carbon dioxide gas and sodium carbonate addition; dissolved oxygen is controlled by air, nitrogen, and oxygen gas flows.

At the end of production, the cell broth is fed into a disk stack centrifuge and the culture supernatant is separated from the cells. The concentrate is further clarified through a depth filter followed by a 0.2 µm filter. The clarified conditioned media is then concentrated by tangential flow ultrafiltration. The conditioned media is concentrated 15- to 30-fold. The resulting concentrated conditioned medium is then either processed through purification or frozen for purification at a later date.

Example 7

Cross-Reactivity with Other Neurotrophins

The 4D4 antibodies were tested for their cross-reactivity against human NT3 or human BDNF in different bioassays, including the DRG neuron survival assay for human NT3 and the assay of DA uptake in cultured DA neurons for human BDNF.

Treatment of DRG Cultures with NT3, Anti-NT3 and Anti-NGF Antibodies

Two hours after plating, DRG cells (isolation procedure described above in Example 3) were treated with recombinant hNT-3 100 ng/ml (3.8 nM). Serial-diluted anti-hNT3 antibody (R&D) was used as a positive control. Unknowns (anti-NGF Ab samples) were added at various concentrations with 10 point, 3.16 fold serial dilutions. All the samples were diluted in complete medium before being added to the cultures.

Measurement of MAP2 Expression in DRG Neurons

Cultures were fixed with 4% paraformaldehyde in Hanks' balanced salt solution for 15 min, blocked with Superblock (Pierce) for 1 hour and permeabilized with 0.25% Nonidet P-40 (Sigma) in Tris-HCl (Sigma)-buffered saline (TBS) for 1 hour in room temperature (RT). Cultures were rinsed once with TBS containing 0.1% Tween20 (Sigma) and incubated with mouse anti-MAP2 IgG (Chemicon, Temecula, Calif.) for 1.5 hour at room temperature, followed by incubation of Eu-labeled anti-mouse secondary antibody (Wallac Oy, Turku, Finland) for 1 hour at room temperature. Washes with TBS (3×5 min with gentle shaking) were applied after each antibody incubation. Enhance solution (150 ml/well, Wallac Oy) was added to the cultures and fluorescence signal was then measured in a time-resolved fluorometer (Wallac Oy).

Embryonic Mesencephalic Culture

Embryonic 19 day old (E19) Sprague-Dawley rats (Jackson Labs) were used. Ventral midbrain tissue enriched for dopaminergic neurons was removed and transferred to cold, Dulbecco's phosphate buffered saline (DPBS), pH 7.4, without $Ca^{++}$ and $Mg^{++}$ (Gibco). The tissue fragments were dissociated into single cell suspension using a papain dissociation system (Worthington Biochemical Corp., Freehold, N.J.). Briefly, tissue fragments were incubated in a digestion solution containing 20 unit/ml papain in Earle's Balanced Salt Solution (EBSS) at 37° C. for 50 min. Cells were dissociated by trituration through fire-polished Pasteur pipettes in a dissociation medium consisting MEM/Ham's F12 1:1, 1 mg/ml ovomucoid inhibitor and 1 mg/ml ovalbumin and 0.005% deoxyribonuclease I (DNase). The dissociated cells were pelleted at 200×g for 5 min and resuspended in EBSS containing 1 mg/ml ovomucoid inhibitor, 1 mg/ml ovalbumin and 0.005% DNase. Cell suspension was centrifuged through a gradient solution containing 10 mg/ml ovomucoid inhibitor, 10 mg/ml ovalbumin at 200×g for 6 min to remove the cell debris; and filtered through a 25 µg Nitex nylon mesh (Tetko, Inc.) to remove the clumps. The dissociated cells were plated in tissue culture plates at a density of $100,000/cm^2$. The plates were pre-coated with poly-ornithine 100 µg/ml (Sigma) and mouse laminin 1 µg/ml (Gibco BRL) as previously described (Louis J C et al., *J. Pharmacol. Exp. Ther.* 1992; 262:1274-1283.). The culture medium consisted of minimal essential medium (MEM)/Ham's F12, 1:1, 12% horse serum (Gibco), 100 µg/ml transferrin and 2.5 µg/ml insulin (Sigma). The cultures were kept at 37° C., 5% CO2 and 100% humidity for 6 days.

Treatment of Mesencephalic Cultures with BDNF and Anti-BDNF or Anti-NGF

BDNF at 10 ng/ml was added to the cells 2 hours after plating, followed by serial concentrations of anti-NGF Ab samples. Anti-BDNF antibody (generated at Amgen) was used as a positive control.

DA Uptake in Mesencephalic Neurons

Dopamine uptake assay were carried out as described previously (Friedman, L. and Mytilineou, C., *Neuroscience Letters* 1987; 79:65-72). At day 6, cultures were washed once with pre-warmed Krebs-Ringer's phosphate buffer (pH 7.4) containing 5.6 mM glucose, 1.3 mM EDTA and 0.5 mM pargylin, a monoamine oxidase inhibitor. The cultures were incubated in uptake buffer containing 50 nM [$^3$H]DA (NEN) for 60 minutes at 37° C. Uptake was stopped by removing the uptake buffer, and the cultures were washed three times with Krebs-Ringer's phosphate buffer. Cells were lysed to release [$^3$H]DA by adding a liquid scintillation cocktail, opticphase supermix (Wallac), directly to the cultures. The cell lysates were then counted for radioactivity in a microbeta-plus liquid scintillation counter (Wallac, Inc.). Low affinity DA uptake was assessed by adding 0.5 mM GBR12909, a specific inhibitor of the high affinity DA uptake sites (Heikkila R E and Mazino L, *European Journal of Pharmacology* 1984; 103: 241-8), to the uptake buffer, and subtracted from the total uptake amount to obtained the high affinity DA uptake value.

TABLE 6

| Antibody | IC50 @ hNT-3 (nM) | IC50 @ hBDNF (nM) |
|---|---|---|
| 4D4 (IgG2) | >13.75 | >13.75 |

Example 8

Identification of an Epitope for Anti-NGF Antibodies

Epitope Mapping by Limited Proteolysis

Five micrograms (μg) of NGF were incubated with 4D4 (11 μg) for 30 minutes at 4° C. in 0.1M Tris buffer, pH 7.5. The complex was then digested with protease (subtilisin) 1 μg at 37° C. for 1 and 2 hours. HPLC peptide maps were compared to each other to find the peptides that were protected by the 4D4 antibodies. Limited proteolysis of NGF indicated that several major peptides were initially released from NGF. Of particular interest, peptides S18.3, S18.5, and S34.4 were generated and protected with antibody from the proteolysis. Other peaks were not significantly formed or protected. The protected peptides from two experiments (1 hour and 2 hour digestion) are shown in Table 7.

TABLE 7

| | | | % protection | |
|---|---|---|---|---|
| | | | 1 hour digestion | 2 hour digestion |
| S16.1 | QAA (96-98) | C-terminal | — | 57 |
| S18.3 | FFETK (53-57) (SEQ ID NO: 45) | Loop region | 40 | 45 |
| S18.5 | SSSHPIFHR (1-9) (SEQ ID NO: 46) (HWNSY)* (SEQ ID NO: 47) | N-terminal | 40 | 50 |
| S34.4 | NSVEKQYFFETK (46-57) (SEQ ID NO: 48) | Loop region | 69 | 38 |

The percentage of protection was calculated from the peptide peak height. S18.5 contained two peptides, but only one peptide (SSSHPIFHR; SEQ ID NO: 46) was 5 protected with the 4D4 antibody, since the other peptide peak (HWNSY; SEQ ID NO: 47) was unchanged by the addition of 4D4 antibodies, as detected at 280 nm absorbance. Peptide S18.3 was a C-terminal part of S34.4, both from the same loop region. N-terminal and central loop regions were also possible epitopes.

Microcon Separation of Digested Peptides

The subtilisin-digested material (3 μg each) was incubated with active 4D4 antibodies and an inactive monoclonal antibody (#162) (8 μg) for 30 minutes at 4° C. in 0.1 M Tris buffer, pH 7.5. The bound/unbound peptides were separated by Microcon 10 (Millipore Corp., Bedford, Mass.) and both fractions (bound and unbound) were analyzed by HPLC to find peptides bound to antibodies. Two depleted peaks identified by HPLC comparison of the unbound fractions after treatment with 4D4 antibodies and #162 and Microcon separation were recovered, indicating antibody bound peptides.

The 4D4 bound peptides were:
S1 (4.4)----SRKAVRR (113-119) (SEQ ID NO: 49), C-terminal; and
S2 (28.3)----EVMVL (35-39) (SEQ ID NO: 50), Loop region.

An NGF sample was alternatively digested with Lys-C (K) for 24 hours. Cysteine residues were reduced and carboxymethylated without denaturant. The sample was incubated with monoclonal antibodies 4D4 and AMG162, followed by Microcon 100 separation. Bound and unbound fractions were analyzed by reversed phase HPLC. Only two peptides were identified as antibody binding K-peptides as indicated below. The calculated mass for the peptides determined by sequence analysis and the mass spectrometry of the peptides were consistent. The peptides, as indicated below, mapped to the N-terminal and C-terminal region.

(SEQ ID NO: 51)
K1(37.6) ----SSSHPIFHRGEFSVCDSVSVWVGDK

Calculated mass=2821; Observed mass=2828.2; N-terminal

K2(39.5) ----QAAWRFIRIDTACVCVLSRK (SEQ ID NO: 52)

Calculated mass=2452; Observed mass=2459.5; C-terminal

The preceding epitope mapping experiments indicated that at least three regions were possible epitopes for the 4D4 antibodies, including N-terminus (1-9), internal (46-57), and C-terminal (96-98) regions. In addition, an AspN digestion revealed that a peptide fragment consisting of ---SSHPIF-HRGEFSVC--- (SEQ ID NO: 53) was protected by the 4D4 antibody, whereas a trypsin digestion showed that a peptide fragment consisting of ---SSHPIFHR---- (SEQ ID NO: 54) was not protected by the 4D4 antibody. Thus, in the N-terminus, the sequence of GEFSVC (SEQ ID NO: 55) is most important for binding to 4D4 antibodies.

In order to more clearly define the epitope for the anti-NGF antibody 4D4.IgG1, a total of 23 peptides were generated synthetically using standard techniques based on the entire human mature NGF (hNGF) sequence (Table 8). The peptides were 15 amino acids long, overlapping by 10 amino acids, and cysteine-tailed at the C-termini to allow for conjugation to a matrix. The human anti-hNGF Ab 4D4.IgG1 described above was used for the mapping experiment.

TABLE 8

| Peptide # | Sequence | SEQ ID NO |
|---|---|---|
| 33582-27-01 | SSSHPIFHRGEFSVC (1-15) | 56 |
| 33582-27-02 | IFHRGEFSVADSVSVC (6-20) | 57 |
| 33582-27-03 | EFSVADSVSVWVGDKC (11-25) | 58 |
| 33582-27-04 | DSVSVWVGDKTTATDC (16-30) | 59 |
| 33582-27-05 | WVGDKTTATDIKGKEC (21-35) | 60 |
| 33582-27-06 | TTATDIKGKEVMVLGC (26-40) | 61 |
| 33582-27-07 | IKGKEVMVLGEVNIN (31-45) | 62 |
| 33582-27-08 | VMVLGEVNINNSVFKC (36-50) | 63 |
| 33582-27-09 | EVNINNSVFKQYFFEC (41-55) | 64 |
| 33582-27-10 | NSVFKQYFFETKARDC (46-60) | 65 |
| 33582-27-11 | QYFFETKARDPNPVDC (51-65) | 66 |
| 33582-27-12 | TKARDPNPVDSGARDC (56-70) | 67 |
| 33582-27-13 | PNPVDSGARDIDSKHC (61-75) | 68 |

TABLE 8-continued

| Peptide # | Sequence | SEQ ID NO |
|---|---|---|
| 33582-27-14 | SGARDIDSKHWNSYC (66-80) | 69 |
| 33582-27-15 | IDSKHWNSYATTTHTC (71-85) | 70 |
| 33582-27-16 | WNSYATTTHTFVKALC (76-90) | 71 |
| 33582-27-17 | TTTHTFVKALTMDGKC (81-95) | 72 |
| 33582-27-18 | FVKALTMDGKQAAWRC (86-100) | 73 |
| 33582-27-19 | TMDGKQAAWRFIRIDC (91-105) | 74 |
| 33582-27-20 | QAAWRFIRIDTAAVC (96-110) | 75 |
| 33582-27-21 | FIRIDTAAVAVLSRKC (101-115) | 76 |
| 33582-27-22 | TAAVAVLSRKAVRRAC (106-120) | 77 |
| 33582-27-23 | CAAVAVLSRKAVRRA (107-120) | 78 |

The human NGF peptide fragments were diluted in PBS with 5% DMSO, 1 mM EDTA, pH 6.23. The final peptide concentration was normalized to the same molar concentration at 55 µM (about 100 µg/ml). Peptides were incubated in Reacti-Bind Maleimide activated 96 well microtiter plates (Pierce Cat #15150), 100 µl/well, at room temperature for 2 hours and then at 4° C. overnight with agitation. Human NGF (100 µg/ml) was used as positive control. The plates were washed with wash buffer (KPL) and blocked with 0.2% non-fat dry milk (in PBS-EDTA buffer, pH 6.23) for 2 hours at room temperature and then further blocked with 5% BSA for 1 hour. Plates were then incubated with the human anti-NGF antibody at various concentrations (0, 3, 10, 30 µg/ml), followed by goat anti-hFc Ab-HRP (KPL) for 2 hours. Signal was developed with TMB substrate and read at 450 nm after addition of stop solution (KPL).

Across the 23 human NGF peptides, at least 4 major peaks were observed, indicating 4D4 binding. These peaks corresponded to the following peptides: Peptide #1 (SEQ ID NO: 56), SSSHPIFHRGEFSVC (1-15); Peptide #10 (SEQ ID NO: 65), NSVFKQYFFETKARD (46-60); Peptides #16-17 (SEQ ID NO: 71-SEQ ID NO: 72), WNSYATTTHTFVKAL--- (76-95); and Peptides #18-21 (SEQ ID NO: 73-SEQ ID NO: 76), TTTHT---LSRKC (100-115).

The four binding peaks of 4D4 mapped to the N-terminus, C-terminus, internal domains, as well as loops L2 and L4 in NGF as described in Weismann et al. (1999, Nature 401:184-8). These results are summarized in Table 9.

TABLE 9

| hNGF epitopes | N-terminus | L2 | Internal | L4 | Internal | C-terminus |
|---|---|---|---|---|---|---|
| Peptide # | peptide # 1 (SEQ ID NO: 56), SSSHPI---, 1-15 | peptide # 10 (SEQ ID NO: 65), NSVFKQ---, 46-60 | peptide # 16 (SEQ ID NO: 71), WNSYA---, 76-90 | peptide # 17 (SEQ ID NO: 72), TMDGKQ---, 81-95 | peptide # 19 (SEQ ID NO: 74), TMDGK---, 91-105 | peptides # 20-21 (SEQ ID NO: 75-SEQ ID NO: 76), QAAWR---, 96-115 |
| Ab binding signal | +++ | + | ++ | ++ | +++ | ++ |

Wiesmann et al. solved the crystal structure of hNGF bound to the trkA receptor, showing that the N-terminus (residues 2-9) was important for receptor binding (Wiesmann et al., 1999, Nature 401:184-8). The residues of this segment in NGF are also important for specificity for trkA over trkB or trkC receptors. Antibody 4D4 is selective for human NGF over mouse/rat NGF, as well as BDNF and NT-3 most likely because N-terminal differences between human NGF and other neurotrophins.

Antibody 4D4 binds to peptide #10 (SEQ ID NO: 65) (NSVFK---, 46-60) and peptide #17 (SEQ ID NO: 72) (TTTHTFVKALTMDGKC, 81-95), corresponding respectively to loops L2 and L4, which represent two of seven distinct regions with higher than average sequence diversity among the neurotrophins. Swapping experiments between NGF and BDNF of these seven regions showed that L2 and L4 were important for the biological activity of NGF. Furthermore, substitution of five NT3 residues in loops L2 and L4 with those of NGF introduced NGF-like activity while maintaining NT3 activity. Thus, L2 and L4 are likely regions where antibody 4D4 bind selectively to NGF rather than to BDNF or NT-3.

Antibody 4D4 also binds to peptide #16 (SEQ ID NO: 71) (WNSYATTTHTFVKAL, 76-90), matching an internal domain of the NGF crystal structure. This region is 100% homologous between human NGF and mouse NGF, but distinct from other neurotrophins. 4D4 showed much weaker activity against rat/mouse NGF when compared to its activity against human NGF. Thus, binding to this part of NGF is most likely not critical for species specificity but is important for selectivity amongst neurotrophins.

Antibody 4D4 also binds to the C-terminal region of NGF (peptides #19-21 (SEQ ID NO: 74-SEQ ID NO: 76) TMDGK---LSRKC, 91-115), which is one of the regions of human NGF that distinguishes NGF from other neurotrophins (BDNF and NT3). Binding to this region helps to explain why 4D4 is not active against other neurotrophins. Furthermore, there is a single amino acid difference between human NGF and mouse NGF in the C-terminus, suggesting that this single amino acid may be one of the reasons 4D4 is selective for human NGF over rat/mouse NGF, similar to the N-terminus where species differences are observed.

Lastly, 4D4 also interacts with an internal domain described by peptide #10 (SEQ ID NO: 65) (---KARDC, 50-60) of human NGF, which is an important region for NGF binding preferentially to trkA, rather than trkB or trkC, further explaining its selective neutralization activity against human NGF.

Example 9

Affinity Measurement of Monoclonal Antibodies by KinExA

Binding of Ab 4D4 (38859-80) to huNGF (29714-91) was tested on KinExA. Briefly, Reacti-Gel 6x (Pierce) were pre-coated with huNGF and blocked with BSA. 10 pM and 30 pM of Ab 4D4 samples were incubated with various concentrations of huNGF (Amgen) at room temperature for 8 hours before run through the huNGF-coated beads. The amount of the bead-bound antibody was quantified by fluorescent (Cy5) labeled goat anti-human-IgG antibody (Jackson Immuno Research). The binding signal was proportional to the concentration of free antibody at equilibrium. Dissociation equilibrium constant ($K_D$) was obtained from nonlinear regression of the competition curves using a dual-curve one-site homogeneous binding model (KinEX™ software). The $K_D$ was about 4 pM for Ab 4D4 binding to huNGF.

Example 10

Identification of Additional Anti-NGF Antibodies

Additional anti-NGF antibodies (designated 14D10, 6G9, 7H2, 14F11, and 4G6), generated and identified as described in Examples 2 and 3 above, were selected for further study. Briefly, conditioned media was tested for binding activity. Antibodies from the media were purified and sequenced. The predicted mass was compared with mass spectrometry data of antibodies from the conditioned media. The antibodies were cloned. Two of the clones were expressed in CHO cells and tested for activity as described above. The results are shown in Table 10.

TABLE 10

| clone | IC50 @ hNGF (nM) | IC50 @ rNGF (nM) | Notes | Molecular Clone | IC50 @ hNGF (nM) | IC50 @ rNGF (nM) |
|---|---|---|---|---|---|---|
| 7H2 | 3.294 | 1.748 | cloned | 7H2-rFc | 0.963 | 0.792 |
| 6H9 | 3.172 | 1.699 | cloned | 6H9-rFc | 13.93 | 0.653 |
| 14D10 | 0.3918 | >13 | cloned | | | |
| 14D11 | 0.2803 | >20 | cloned | | | |
| 4G6 | 0.414 | >10 | cloned | | | |

The sequences of the light and heavy chain variable regions of these antibodies were then compared to the 4D4 antibody sequence, as well as to each other (FIGS. 5 and 6). The percent homologies of the heavy chain variable regions as identified from these comparisons are shown in Table 11. The percent homologies of the light chain variable regions are shown in Table 12. In addition, the percent homologies of the CDR regions of the various antibodies are shown in FIGS. 5-10.

TABLE 11

| | 4D4 VH | 14D10 VH | 6H9 VH | 7H2 VH | 14D11 VH | 4G6 VH |
|---|---|---|---|---|---|---|
| 4D4 VH | 100% | 70.9% | 70.1% | 75.6% | 47.2% | 73.4% |
| 14D10 VH | | 100% | 95.3% | 85% | 54.3% | 81.1% |
| 6H9 VH | | | 100% | 86.6% | 54.3% | 81.1% |
| 7H2 VH | | | | 100% | 51.2% | 79.8% |
| 14D11 VH | | | | | 100% | 56.8% |
| 4G6 VH | | | | | | 100% |

TABLE 12

| | V4D4 VK | 14D11 LC | 4G6a LC | 4G6b LC | 4G6c LC | 14D10 LC | 6H9 LC | 4G6d LC | 7H2 LC | 4G6e |
|---|---|---|---|---|---|---|---|---|---|---|
| V4D4 VK | 100% | 89% | 91% | 72% | 74% | 69% | 71% | 71% | 70% | 73% |
| 14D11 LC | | 100% | 94% | 68% | 71% | 67% | 68% | 68% | 68% | 70% |
| 4G6a LC | | | 100% | 69% | 74% | 68% | 70% | 70% | 69% | 71% |
| 4G6b LC | | | | 100% | 87% | 83% | 86% | 86% | 86% | 96% |
| 4G6c LC | | | | | 100% | 91% | 94% | 94% | 94% | 91% |
| 14D10 LC | | | | | | 100% | 91% | 94% | 94% | 86% |
| 6H9 LC | | | | | | | 100% | 99% | 98% | 89% |

TABLE 12-continued

|   | V4D4 VK | 14D11 LC | 4G6a LC | 4G6b LC | 4G6c LC | 14D10 LC | 6H9 LC | 4G6d LC | 7H2 LC | 4G6e |
|---|---|---|---|---|---|---|---|---|---|---|
| 4G6d LC |  |  |  |  |  |  |  | 100% | 99% | 89% |
| 7H2 LC |  |  |  |  |  |  |  |  | 100% |  |
| 4G6e |  |  |  |  |  |  |  |  |  | 100% |

It should be understood that the foregoing disclosure emphasizes certain specific embodiments of the invention and that all modifications or alternatives equivalent thereto are within the spirit and scope of the invention as set forth in the appended claims.

We claim:

1. A pharmaceutical composition comprising a pharmaceutically acceptable carrier and an isolated antibody comprising a light chain comprising SEQ ID NO: 44 and a heavy chain comprising SEQ ID NO: 40 or an antibody fragment thereof, wherein the antibody or fragment thereof binds nerve growth factor (NGF).

2. A pharmaceutical composition comprising a pharmaceutically acceptable carrier and a single-chain antibody, wherein the single-chain antibody comprises SEQ ID NO: 10 and SEQ D NO: 12, wherein said single-chain antibody binds nerve growth factor (NGF).

3. The pharmaceutical composition of claim 1, wherein the antibody fragment is a single chain Fv.

4. The pharmaceutical composition of claim 1, wherein the antibody fragment is a Fab'.

5. The pharmaceutical composition of claim 1, wherein the antibody fragment is a (Fab')2.

6. The pharmaceutical composition of claim 1, wherein the antibody is fully human.

7. The pharmaceutical composition of claim 1, wherein the antibody inhibits NGF signaling.

8. The pharmaceutical composition of claim 2, wherein the amino acid sequences of SEQ ID NO: 10 and SEQ ID NO: 12 are fully human.

9. The pharmaceutical composition of claim 2, wherein the single-chain antibody inhibits NGF signaling.

10. The pharmaceutical composition of either of claim 1 or 2 wherein the antibody or single-chain antibody dissociates from a human NGF polypeptide with a KD of about $1\times10^{-9}$ M or less and neutralizes human NGF bioactivity in a standard in vitro assay with an $IC_{50}$ of about $1\times10^{-8}$ M or less.

11. The pharmaceutical composition of claim 10 wherein the antibody or single-chain antibody dissociates from a human NGF polypeptide with a KD of about $1\times10^{-10}$ M or less and neutralizes human NGF bioactivity in a standard in vitro assay with an $IC_{50}$ of about $1\times10^{-9}$ M or less.

12. The pharmaceutical composition of claim 11 wherein the antibody or single-chain antibody dissociates from a human NGF polypeptide with a KD of about $1\times10^{-11}$ M or less and neutralizes human NGF bioactivity in a standard in vitro assay with an $IC_{50}$ of about $0.2\times10^{-9}$ M or less.

* * * * *